(12) United States Patent
Molloy et al.

(10) Patent No.: US 7,871,819 B2
(45) Date of Patent: *Jan. 18, 2011

(54) REGULATORY CONSTRUCTS COMPRISING INTRON 3 OF PROSTATE SPECIFIC MEMBRANE ANTIGEN GENE

(75) Inventors: Peter L. Molloy, New South Wales (AU); Fujiko Watt, Rozelle (AU); Gerry Both, New South Wales (AU)

(73) Assignee: Commonwealth Scientific and Industrial Research Organisation, Australian Capital Territory (AU)

( * ) Notice: Subject to any disclaimer, the term of this patent is extended or adjusted under 35 U.S.C. 154(b) by 651 days.

This patent is subject to a terminal disclaimer.

(21) Appl. No.: 11/311,637

(22) Filed: Dec. 20, 2005

(65) Prior Publication Data

US 2006/0183229 A1    Aug. 17, 2006

Related U.S. Application Data

(63) Continuation-in-part of application No. 09/914,651, filed as application No. PCT/AU00/00143 on Mar. 1, 2000, now Pat. No. 7,074,400.

(30) Foreign Application Priority Data

Mar. 1, 1999 (AU) .................................... PP8956
Jan. 25, 2000 (AU) .................................... PQ5268

(51) Int. Cl.
*C12P 21/00* (2006.01)
*A61K 48/00* (2006.01)
*C12N 15/00* (2006.01)
*C12N 15/86* (2006.01)
*C12N 15/861* (2006.01)
*C07H 21/04* (2006.01)

(52) U.S. Cl. ...................... 435/456; 435/69.1; 435/70.1; 435/70.3; 435/455; 435/320.1; 514/44 R; 536/23.1; 536/24.1

(58) Field of Classification Search ........................ None
See application file for complete search history.

(56) References Cited

U.S. PATENT DOCUMENTS

| 5,538,866 A | 7/1996 | Israeli et al. |
| 6,020,172 A * | 2/2000 | Both ...................... 435/91.41 |
| 7,074,400 B1 * | 7/2006 | Molloy et al. .............. 424/93.2 |

FOREIGN PATENT DOCUMENTS

| AU | 51725/96 | 9/1996 |
| WO | WO 9603508 A1 * | 2/1996 |
| WO | WO 9706826 A1 * | 2/1997 |
| WO | WO 98 33903 A | 8/1998 |

OTHER PUBLICATIONS

Xu et al., Virology, 1997, vol. 230, pp. 62-71.*
Loser et al., Gene Therapy, 2000, vol. 7, pp. 1491-1498.*
Wang et al., Gene Therapy, Sep. 2004, vol. 11, pp. 1559-1567.*
"Prostate-Specific Membrane Antigen", W. R. Fair et al., Prostate, Wiley-Liss, New York, NY, US, vol. 32, No. 2, 1997, pp. 140-148, XP000870112, ISSN: 0270-4137.
"Mapping, genomic organization and promoter analysis of the human prostate-specific membrane antigen gene", O'Keefe et al., Biochemica et Biophysica Acta 1443, (1998), pp. 113-127.
Genbank Accession No. AF007544, printed Apr. 6, 2000 as p. 1-29.
"Detailed genetic mapping around a putative prostate-specific membrane antigen locus on human chromosome 11p11.2", Maraj et al., Cytogenetics and Cell Genetics, Vo. 81 (1998), pp. 3-9.
"Cloning and Characterization of the Prostate-Specific Membrane Antigen Promoter", Good, D. et al., Journal of Cellular Biochemistry 74(3), pp. 395-405, Sep. 1999.
Orkin, et al. Report and recommendations of the Panel to Assess the NIH Investment in Research on Gene Therapy, The National Institutes of Health, Dec. 7, 1995.
Verma, et al. Nature, Sep. 1997, vol. 389, pp. 239-242.
Anderson, French W. Nature, Apr. 1998, vol. 392, pp. 25-30.
Palu et al. J. Biotechnol, 1999, vol. 68, pp. 1-13.
Luo et al. Nature Biotechnology, 2000, vol. 18, pp. 33-37.
Check, Erica. Nature, Feb. 2003, vol. 421, p. 678.

* cited by examiner

*Primary Examiner*—Jennifer Dunston
(74) *Attorney, Agent, or Firm*—McDermott Will & Emery LLP

(57) ABSTRACT

The invention provides a recombinant vector comprising an ovine adenovirus genome and a sequence encoding a heterologous polypeptide, wherein the sequence encoding the heterologous polypeptide is inserted between E4 and E3 transcription units of the ovine adenovirus genome.

14 Claims, 16 Drawing Sheets

Sequence of 331 base pair core region of the PSME

14760
AATTATTTTTTCCTTTAACCTTTCAAACTCAAGGAAAACCAGTTGGCCTTGACTCTGTTT
14820
GTGGAAAATTTTAAACTACTGGTTTAATTTCTTTATTGGTTGTAATATGACTATTTTACG
14880
TCATATAACAATTTTTATTGTTTGTTAAATGACTTTATTGTTTGT<u>CATATGA</u>TAATTTTA
14940
TGTCATAGAACAATTTTTATTGCTTGATATATGACTTTATTGTTATATGGCTATACAACT
15000
AGATTTTTTTGTTGTTTTTGACCGAGTCTTACTCTGTCACCCAGGCTGGAGTGTAATGGC
15060
ATGGTCTCAGCTCACTGCAACCTCCGCCTCCCGGG

The NdeI site 168 base pairs from the start of the core enhancer is underlined

Figure 11

REGULATORY CONSTRUCTS COMPRISING INTRON 3 OF PROSTATE SPECIFIC MEMBRANE ANTIGEN GENE

This application is a continuation-in-part of U.S. patent application Ser. No. 09/914,651, filed on Dec. 27, 2001, now U.S. Pat. No. 7,074,400, the entire contents of which is incorporated herein. U.S. patent application Ser. No. 09/914,651 is a national stage entry under 35 U.S.C. 371 of PCT/AU00/00143, filed on Mar. 1, 2000.

FIELD OF THE INVENTION

The present invention relates to a recombinant vector comprising an ovine adenovirus genome and a sequence encoding a heterologous polypeptide. The invention also provides ovine adenovirus recombinant vectors comprising a novel regulatory element derived from a prostate specific gene. The present invention also relates to diagnostic and therapeutic methods involving the use of these vectors.

BACKGROUND OF THE INVENTION

The isolation and characterisation of DNA regions which control tissue specific and/or hormonally-regulated gene expression has been an important to the understanding of the developmental processes by which expression of particular genes is limited to specific cell types. Promoter regions are found immediately upstream and often overlapping the start site(s) of transcription and are critical for initiation and basal levels of transcription. Enhancers are regulatory regions which may lie some distance from the transcription start site, either upstream or downstream of a gene or within introns and which often confer high level tissue specific or hormonally-regulated expression; in some cases their action is specific to particular promoters. The function of both promoters and enhancers is mediated by specific proteins, transcription factors, that bind to specific DNA sequences. Alone or in combination with other transcription factors they recruit the core transcription machinery including RNA polymerase to the transcription initiation site and act to stimulate their activity. Isolated promoters and enhancer sequences can be used, in gene therapy for example, to direct expression of other genes in a cell or tissue specific manner and also provide targets for the development of agents that can specifically modulate gene expression.

The promoters and regulatory regions of a number of genes that are expressed in the prostate have been studied either using transfection techniques or by following gene expression in transgenic mice. We have previously compared the cell-type specificity of expression directed by promoters of the prostate-expressed genes, probasin (Pb) and relaxin genes and the promoter and enhancer of the prostate specific antigen (PSA) gene (1). Most of the genes identified as prostate-specific are androgen-inducible and this aspect of their function has been studied in some detail. Thus the importance of androgen response elements for induced expression and/or binding of androgen receptor have been characterised in the PSA (2,3), human glandular kallikrein (KLK2) (4), rat prostatic steroid binding proteins (PSBP) (5,6), probasin Pb (7,8) and prostatic acid phosphatase genes (9) and in regulatory elements in the introns of the rat PSBP C3(1) gene (10) and the rat 20-KDa androgen regulated protein (11).

Among the core promoter regions analysed only that of the probasin gene confers substantial prostate specificity of expression (1,15). Elements involved in conferring prostate-specificity of expression per se, as distinct from androgen responsiveness, have not been well characterised, though tissue-specific factors binding to regions of the PSBP C3 gene promoter and 1st intron have been identified (9,12). The gene for rat PSBP C(3) with 4 kb upstream and 2 kb downstream flanking sequences is expressed tissue-specifically and with appropriate hormonal control in transgenic mice (13). The use of a 5 kb upstream region from the rat PSBP C3(1) gene to express the SV40 T-antigen could elicit prostate tumours, but expression was not highly restricted and other abnormalities were common (14). Studies with transgenic mice have established that regions of the probasin and PSBP C(3) genes can confer prostate specificity.

The PSA and probasin regulatory regions are the two most studied among prostate-expressed genes. It has been established that a 430 bp region upstream of the rat probasin gene is able to confer prostate specificity of expression on reporter genes in transfection experiments (1) and in transgenic animals (15,16); when used to target expression of the SV40 T-antigen, prostate tumours develop specifically (17,18). This expression is not totally specific but specificity is significantly improved by the inclusion of MAR (matrix attachment regions) from the chick lysozyme gene (15). The 430 bp promoter region is strongly responsive to androgen induction and androgen response elements which bind the androgen receptor (AR) have been characterised (4,6,7,16).

The PSA upstream region (to-630 bp) also acts as a strongly androgen responsive promoter and androgen response elements have also been characterised (2,3). However, this region is not sufficient to direct cell type specific expression in culture (1) or tissue specific expression in transgenic mice (19). Use of the 630 bp human PSA promoter region to express an activated Ha-ras oncogene in transgenic mice led to the development of salivary gland and not prostate tumours (19). Pang et al. have reported that the equivalent promoter region isolated from a prostate cancer patient contained 7 mutations compared to the published sequence and was highly active in the prostate cancer cell line LNCaP (20,21). More recently, an enhancer region has been identified in the region 4 to 5 kb upstream of the transcription start site of the PSA gene (20,21). This PSA enhancer has been shown to act as an androgen-inducible enhancer and in combination with the PSA promoter to display significant cell-type specificity (1,20,21).

Prostate-Specific Membrane Antigen

Prostate specific membrane antigen (PSMA) is one of the few prostate-specific proteins identified whose expression is not induced by androgens.

PSMA was first identified as the antigen bound to by the monoclonal antibody 7E11-C5 (25). The antibody was raised against a membrane fraction of the prostate cancer cell line LNCaP and was shown to bind specifically to normal prostate tissue as well as primary and metastatic prostate cancer tissue. This antibody was later found to bind to an internal epitope of this membrane-bound protein (26,27). Subsequently, other monoclonal antibodies targeted to the extracellular domain of the protein have been isolated (28,29).

The cDNA encoding PSMA has been cloned and its sequence determined (30). PSMA is a Type II integral membrane protein and is associated with the plasma membrane of expressing cells such as LNCaP (30). A splice variant of PSMA (Psm') that lacks the membrane anchor domain and has been shown to be cytoplasmically located has also been identified (31). The ratio of PSMA to Psm has been reported to be increased in prostate cancer as compared with normal prostate or benign hyperplasia (31). PSMA has been shown to possess two related enzymatic activities, it acts as a carboxypeptidase (folate hydrolase) on poly γ-glutamated folates (32) and as a peptidase on the acidic neuropeptide N-acetylaspartyl glutamate (33). This latter activity is consistent with the expression of PSMA or a related protein in the brain.

The specificity of PSMA expression has been studied at both the protein and RNA level. In addition to its major site of expression in the prostate immunohistochemical studies have identified PSMA expression in the duodenum brush border/small intestine, in a subset of proximal tubules in the kidney and in rare cells in the colon (34,35). All other normal issues studies have been negative for expression, except for striated muscle which stains with the 7E11-C5 antibody, but not with antibodies to the external domain of PSMA (28).

Both the 7E11-C5 and external domain antibodies have been found to react with tumour vasculature of a wide range of human tumour types (28,36), indicating specific induction of PSMA expression. PSMA expression has not been identified in any normal vasculature.

RNA expression has been found to largely parallel the protein expression data. RNAse protection analysis identified PSMA mRNA in the prostate, salivary gland and brain and sometimes in the small intestine (37). The identification of PSMA RNA in the brain is consistent with the cloning of a closely related cDNA from rat brain (33). Immunohistochemical analyses have failed, however, to identify antigenically reactive PSMA in human brain tissue.

PSMA expression has been shown to be down regulated in the presence of androgens and expression is generally elevated in late stage prostate cancer and in patients undergoing androgen deprivation or ablation therapies (37,38). Expression of PSMA has also been found to be regulated by a number of growth factors; bFGF, TGF-α and EGF upregulate expression while TNF-α decreases it (39).

The restricted high level expression of PSMA in prostate cells and the induction of its expression in the vasculature of a wide range of tumours make it ideal for the targeting of prostate and other tumour types. Genomic clones encompassing the PSMA gene have been isolated and its sequence and exon/intron structure determined (40). Regulatory regions controlling its expression may find use in gene therapeutic cancer treatments, enabling the restricted or high level expression in the target cell types. Such regulatory regions also provide a target for the development of agents that may interfere with gene expression in the target cell types.

SUMMARY OF THE INVENTION

The present invention provides a recombinant vector comprising an ovine adenovirus genome and a sequence encoding a heterologous polypeptide, wherein the sequence encoding the heterologous polypeptide is inserted between E4 and E3 transcription units of the ovine adenovirus genome.

When used herein, the PSM gene refers to the PSM genomic sequence described in O'Keefe et al, 1998 (40) (GENBANK (database of nucleotide sequences maintained by the US National Center for Biology Information) accession number AF007544) (SEQ ID NO: 2), the entire contents of which are incorporated herein by reference.

By "heterologous polypeptide" we mean a polypeptide other than the prostate specific membrane antigen (PSMA) polypeptide.

The present invention also provides a recombinant vector as hereinbefore described wherein the sequence encoding the heterologous polypeptide is inserted between nucleotides 26,682 and the 5' end of the E4 promoter of the ovine adenovirus genome. The present invention also provides that the heterologous polypeptide is inserted between nucleotides 26,682 and 26,555 of the ovine adenovirus.

The present invention also provides a recombinant vector as hereinbefore described wherein the sequence encoding the heterologous polypeptide is inserted between an ARP1 and Not1 site between the E4 and E3 transcription units of the ovine adenovirus genome.

In a preferred embodiment, the recombinant DNA molecule further comprises a promoter. Preferably, the promoter is located upstream from and is operably linked to the sequence encoding the polypeptide.

In a preferred aspect of the present invention there is provided a recombinant vector as hereinbefore described wherein the promoter is located upstream from and is operably linked to the sequence encoding the heterologous polypeptide. Preferably, the vector comprises at least one regulatory element derived from intron 3 of the PSM gene.

In a second aspect, the present invention provides a method for directing expression of a coding sequence in a cell, the method comprising introducing into the cell a recombinant vector as hereinbefore described.

In a third aspect of the present invention there is provided a method of delivering a sequence encoding a heterologous polypeptide to a target cell, the method comprising transducing the cell with a recombinant vector as hereinbefore described.

In a fourth aspect of the present invention there is provided a method of delivering a sequence encoding a heterologous polypeptide to an animal cell, the method comprising administering to an animal or animal cell a recombinant vector as hereinbefore described.

In a fifth aspect of the present invention there is provided a method of gene transfer to human cells, the method comprising administering to the cells a recombinant vector as hereinbefore described such that the vector infects at least one cell and the infected cell expresses the heterologous polypeptide.

DETAILED DESCRIPTION OF THE INVENTION

The present inventors have now found that recombinant ovine adenovirus vectors which comprise foreign genes inserted at site E3 transcription site (III), i.e. between the 3' end of the transcription unit for the Right Hand End and the promoters for the E4 region (see FIG. 13) are surprisingly more stable than ovine adenovirus vectors which comprise foreign genes inserted at other sites.

As site III is located between transcription units, it is believed that the insertion of a discrete transcription cassette at this site is unlikely to interfere with other viral functions. Based on these results it is envisaged that the insertion of expression cassettes into the ovine adenovirus genome between coding regions of transcription units which are adjacent in ovine adenovirus genome, such as between the Left Hand End and IVa$_2$ transcription units, will also give rise to stable recombinant constructs.

It is preferred that the heterologous nucleic acid sequence is inserted between the Right Hand End transcription unit (i.e. E3 transcription unit) and the E4 transcription unit or between the Left Hand End transcription unit and the IVa$_2$ transcription unit.

In a further preferred embodiment of the first aspect, the ovine adenovirus genome is the genome of ovine adenovirus OAV287 (as described in GENBANK Accession No. U40839) or a functionally equivalent sequence.

The phrase "functionally equivalent sequence" is intended to cover minor variations in the OAV287 genome which, due to degeneracy in the genetic code, does not result in the genome encoding different viral polypeptides. Further, this term is intended to cover alterations in the genomic sequence which lead to changes in the encoded polypeptides, but in which such changes do not substantially affect the biological activities of these viral polypeptides.

In the context of the present invention, the heterologous nucleic acid molecule (ie sequence encoding a heterologous polypeptide) may be any nucleic acid molecule of interest. For example, the nucleic acid of interest may comprise a therapeutic gene or may encode an antigenic peptide.

The therapeutic gene may be, for example, an oncogene or a tumour suppressor gene. Alternatively, the therapeutic gene may encode a product such as an enzyme, a blood derivative, a hormone, a lymphokine, an interleukin, an interferon, a TNF, a growth factor, neurotransmitter, a trophic factor, etc.

The therapeutic gene may also encode a macromolecule which complements a genetic defect in a somatic cell, or a macromolecule which catalyses one or more processes leading to cell death. Cell death may occur directly as a result of gene expression or indirectly as a result of an immune response to an expressed foreign antigen. Preferably, the gene encodes an enzyme such as herpesvirus thymidine kinase or non-mammalian cytosine deaminase which metabolizes a prodrug. More preferably the gene encodes prokaryotic purine nucleoside phosphorylase. In the presence of the appropriate prodrug, expression of the gene by the transfected cell preferably leads to metabolism of the prodrug giving rise to a toxic product which leads to cell death.

In a further preferred embodiment, the heterologous nucleic acid comprises a cell-specific promoter linked to the therapeutic gene, such that the gene is only expressed in a desired target cell. Such promoters are well known in the art. For example, for specific expression in prostate cells, the promoter may be selected from the probasin, prostate specific antigen (PSA) or prostate specific membrane antigen (PSMA) promoters. For specific expression in breast cells, the erbB-2 promoter may be used. For specific expression in lung cells, the carcinoembryonic antigen (CEA) promoter may be used.

All publications mentioned in this specification are incorporated herein by reference.

The regulatory element(s) in the vectors of the present invention may be located in either orientation anywhere within the recombinant DNA molecule or expression cassette of the present invention. For example, the regulatory element may be located downstream of the coding sequence (e.g. downstream of the 3' termination or polyadenylation signals) or within an intron located in the coding sequence. In a preferred embodiment, the regulatory element is located adjacent to the promoter. More preferably, the regulatory element is upstream of the promoter.

As the vectors of the present invention are useful for expression of proteins in vascular endothelial cells, a range of cancer types may be treated within the context of the sixth aspect of the present invention. Examples of suitable cancer types include renal cell carcinoma, transitional cell carcinoma, colonic adenocarcinoma, neuroendocrine carcinoma, malignant melanoma, pancreatic duct carcinoma, breast carcinoma, soft tissue carcinoma, non-small cell lung carcinoma, testicular embryonal carcinoma and glioblastoma multiforme. In a preferred embodiment of the sixth aspect, however, the cancer is selected from prostate, bladder or breast cancer.

As will be appreciated by those skilled in the field, the present invention provides novel regulatory elements from a gene expressed specifically in prostate, which are active both in the presence and absence of androgens.

These regulatory elements may therefore be used for high level gene expression in prostate cells. Combinations of one or more of the regulatory elements with the probasin and PSA promoters are examples of constructs that provide for high level expression with strong prostate specificity.

The regulatory elements of the present invention may also be useful for directing expression in a limited range of other cell types, including tumour neovasculature and kidney cells.

The regulatory elements of the present invention may be used to target specific expression of genes to prostate cells or tumour neovasculature or kidney cells in gene therapy.

The regulatory elements of the present invention may also be used to target specific expression of genes in the development of transgenic animal models of prostate disease.

The regulatory elements of the present invention may also be used to identify other genetic elements which are involved in the regulation of gene expression in prostate cells.

The regulatory elements of the present invention may also be used in assays to identify reagents that interfere with prostate gene expression, or to identify proteins and other factors involved in regulation of prostate gene expression.

When used herein, "high stringency" refers to conditions that (i) employ low ionic strength and high temperature for washing after hybridisation, for example, 0.1×SSC and 0.1% (w/v) SDS at 50° C.;

(ii) employ during hybridisation conditions such that the hybridisation temperature is ≦25° C. lower than the duplex melting temperature of the hybridising polynucleotides, for example 1.5×SSPE, 10% (w/v) polyethylene glycol 6000, 7% (w/v) SDS, 0.25 mg/ml fragmented herring sperm DNA at 65° C.; or (iii) for example, 0.5M sodium phosphate, pH 7.2, 5 mM EDTA, 7% (w/v) SDS and 0.5% (w/v) BLOTTO at 70° C.; or (iv) employ during hybridisation a denaturing agent such as formamide, for example, 50% (v/v) formamide with 5×SSC, 50 mM sodium phosphate (pH 6.5) and 5×Denhardt's solution at 42° C.; or (v) employ, for example, 50% (v/v) formamide, 5×SSC, 50 mM sodium phosphate (pH 6.8), 0.1% (w/v) sodium pyrophosphate, 5×Denhardt's solution, sonicated salmon sperm DNA (50, μg/ml) and 10% dextran sulphate at 42° C.

Throughout this specification, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the nature of the present invention may be more clearly understood preferred forms thereof will now be described with reference to the following non-limiting Examples and Figures.

pPSMentrap Vector. Key features of the vector are shown: the multicloning site (MCS) unique restriction sites upstream of the PSM1k promoter region (PSM1k), leader sequence and intron (intron) derived from the pCI vector (Promega), the green fluorescent protein gene (GFP) and 3' sequences derived from the bovine growth hormone gene (bGHpA). A selection of useful restriction enzyme sites are shown; unique restriction enzyme sites are shown in bold.

FIG. 2.

Location of cloned PSM enhancer fragments: the map shows the location of the cloned enhancer fragments within intron 3 of the PSM gene.

Base numbers (GENBANK Accession No. AF007544) are indicated for the boundaries of intron 3 and for the ends of the cloned segments. The locations of the restriction sites SmaI (Sm), HinDIII (H) and SpeI (Sp) within the intron are shown. The arrows indicate the orientation of the cloned sequences within the pPSMentrap vector (see FIG. 3). The right hand end of the enhancer clone #1 is shown as a stippled box since this end of the clone has undergone rearrangement. The SmaI, HinDIII and SpeI sites are present in all three cloned regions.

Figure 2:
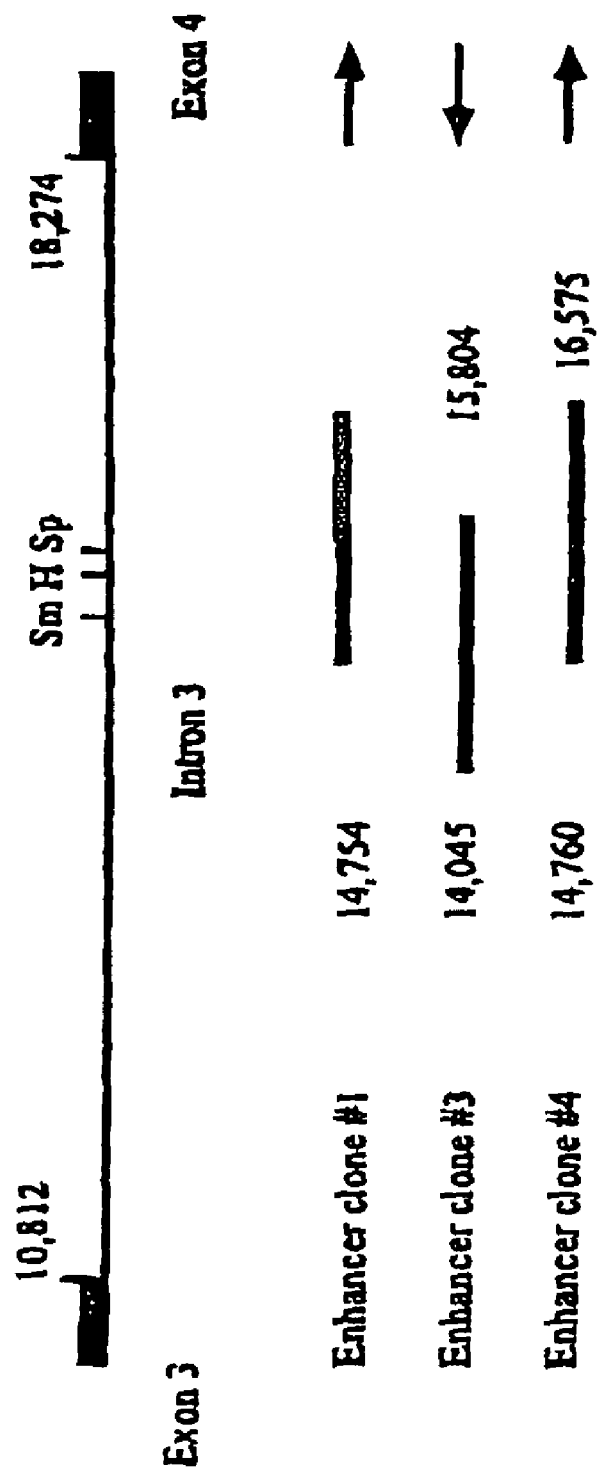

GL3 and pEn3PSmlk-GL3 contain sequences of enhancer clones #4 and #3 respectively as shown in FIG. 2. pEn3+4PSMlk-GL3 contains PSM enhancer sequences encompassing bases 14,045 to 16,575 (see FIG. 2). POverlap3, 4aPSMlk-GL3 and pOverlap3, 4bPSMlk-GL3 contain enhancer sequences from bases 14,760 to 15,804, the a and b constructs containing the enhancer sequences in opposite orientations as indicated by the position of the HinDIII and SpeI sites.

Restriction enzyme sites are abbreviated as follows:

| A | ApoI | B2 | BglII | Bz | BstZI | E | EcoRI | Eo | EcoO1091 | H | HinDIII |
|---|---|---|---|---|---|---|---|---|---|---|---|
| K | KpnI | M | MfeI | Ml | MluI | N | NsiI | Nh | NheI | Nt | NotI |
| P | PstI | RV | EcoRV | S | SalI | Sc | SacI | Sc2 | SacII | Sm | SmaI |
| Sp | SpeI | X | XbaI | Xh | XhoI | | | | | | |

FIG. 3.

Promoter and enhancer inserts in pPSMentrap: The positions of the PSM 1 kb promoter region and flanking restrictions sites in pPSMentrap are shown on the top line. To the right of the promoter sequences are the leader sequence and chimeric intron and GFP reporter gene. Below are shown maps of clones containing the En3 and En4 inserts. The sequences are in opposite orientation (note order of HinDIII and SpeI sites). Restriction sites are abbreviated as follows:

| B2 | BglII | E | EcoRI | H | HinDIII | K | KpnI | M | MfeI | N | NsiI |
|---|---|---|---|---|---|---|---|---|---|---|---|
| Nh | NheI | P | PstI | S | SalI | Sp | SpeI | X | XbaI | | |

FIG. 4.

Promoter and enhancer inserts in pCAT3SAT. Maps show the positions of the PSM 1 kb promoter, PSM En4 and the RSV promoter and their flanking restriction enzyme sites. To the right of the promoters is the leader sequence and chimeric intron and CAT reporter gene as present in the Promega pCAT3 Basic vector. Restriction enzyme sites are abbreviated as follows:

| B2 | BglII | Bz | BstZI | E | EcoRI | H | HinDIII | K | KpnI | M | MfeI |
|---|---|---|---|---|---|---|---|---|---|---|---|
| Ml | MluI | N | NsiI | Nh | NheI | P | PstI | S | SalI | Sc | SacI |
| Sm | SmaI | Sp | SpeI | X | XbaI | Xh | XhoI | | | | |

FIG. 5.

Relative CAT expression directed by the PSM Enhancer4/PSMlk promoter. Following transfection of pPSMLK-C3S or pEn4PSM1K-C3S into the cell lines indicated normalized expression levels were determined for each construct and are expressed relative to that determined from transfection of the pRSV-C3S plasmid.

FIG. 6.

Promoter and enhancer inserts in pGL3. Maps show the position and flanking restriction enzyme sites of the PSM 1 kb promoter (shaded boxes), PSM enhancer fragments (solid boxes) and the RSV promoter (diagonal shading) in the different constructs prepared in the pGL3 vector. To the right of the region shown is the leader and chimeric intron and luciferase reporter gene of the pGL3 vector. PEN4PSMlk-

FIG. 7.

Relative luciferase expression of PSM enhancer/promoter constructs in the pGL3 vector. Mixtures of luciferase reporter plasmids (1.5 µg) and the normalizing plasmid pRSV-CAT (1 µg) were transfected into different cell lines as shown. Normalized luciferase expression was determined and activity of the different plasmids expressed relative to the normalized expression from pRSV-GL3. Numbers above the columns indicate the relative enhancement of activity compared with expression from the PSM promoter alone construct, pPSMlk-GL3.

FIG. 8.

PSM enhancer constructs with other promoters. Maps show the positions and flanking restriction enzyme sites of the PSM enhancer sequences (En4, solid boxes), and promoters from the PSA (diagonal pattern), probasin (vertical pattern) and thymidine kinase (horizontal pattern) genes. To the right of the promoters is the CAT reporter gene of the pCATSAT vector. Restriction enzyme sites are abbreviated as follows:

| B | BamHI | B2 | BglII | E | EcoRI | H | HinDIII | N | NsiI | P | PstI |
|---|---|---|---|---|---|---|---|---|---|---|---|
| S | SalI | | Sm | SmaI | Sp | SpeI | | X | XbaI | | |

FIG. 9.

Relative enhancement of heterologous promoters by PSM En4.

a. Prostate cell lines b. Non-prostate cell lines

The different promoter and enhancer constructs were transfected into cell lines as shown and CAT reporter gene expression normalized against SAT expression determined. Activities are expressed as a percentage of the normalized expression of pRSV-CAT. Numbers above the columns indicate the relative enhancement of activity compared with expression from the respective promoter alone constructs. An * indicates that expression levels were too low to determine a ratio.

FIG. 10.

Effect of androgen on enhancement of heterologous promoters by PSM En4. Plasmids containing the different enhancer/promoter combinations as indicated below the graph were transfected into LNCaP cells that were maintained in medium that had been charcoal stripped to remove androgens or in equivalent medium to which the non-metabolizable androgen analogue R1881 had been added to 0.28 nM.

The presence or absence of androgen is also indicated (− or +) below the graph. Activities were determined and expressed as described in FIG. 9.

FIG. 11.

Sequence of 331 base pair core region of the PSME (SEQ ID NO: 1).

FIG. 12.

Specificity of purine nucleoside phosphorylase (PNP) gene expression in viral constructs OAV223 and OAV623 (PSME and probasin promoter), OAV220 (PSME and RSV promoter) and OAV222 (PSME and CMV promoter).

FIG. 13

Structure of the OAdV genome showing the sites for insertion of foreign gene cassettes.

FIG. 14

Structure of a series of constructs prepared in which the probasin promoter, with or without PSM enhancer fragments was subcloned in front of the luciferase reporter gene in the pGL3 vector.

FIG. 15

Map of a construct in which the pGEM11 plasmid in which the PNP gene was placed under the control of the 1 kb PSME region (bases 14760 to 15804 in reverse orientation) adjacent to the 430 bp probasin promoter.

EXPERIMENTAL DETAILS

Example 1

Isolation of PSMA Gene Enhancer Sequences

Analyses of the region upstream and encompassing the transcription start site of the PSMA gene (40) has shown that a 1 KB region directs expression of reporter genes in the prostate cell line LNCaP. This expression shows specificity for prostate cells when compared to that directed by the SV40 enhancer/promoter. Expression in LNCaP cells was about 75% of that directed by the SV40 enhancer/promoter. Comparison with another widely expressed promoter, that of the Rous sarcoma virus (RSV) has indicated that the SV40 enhancer/promoter is only very weakly active, <1% of RSV activity, in LNCaP cells (unpublished data). We have cloned regions encompassing up to 11 kb of sequences 5' to the PSMA transcription start site and tested their ability to provide increased reporter gene expression; no increased activity was seen relative to the 1 kb promoter region.

Figure 1:
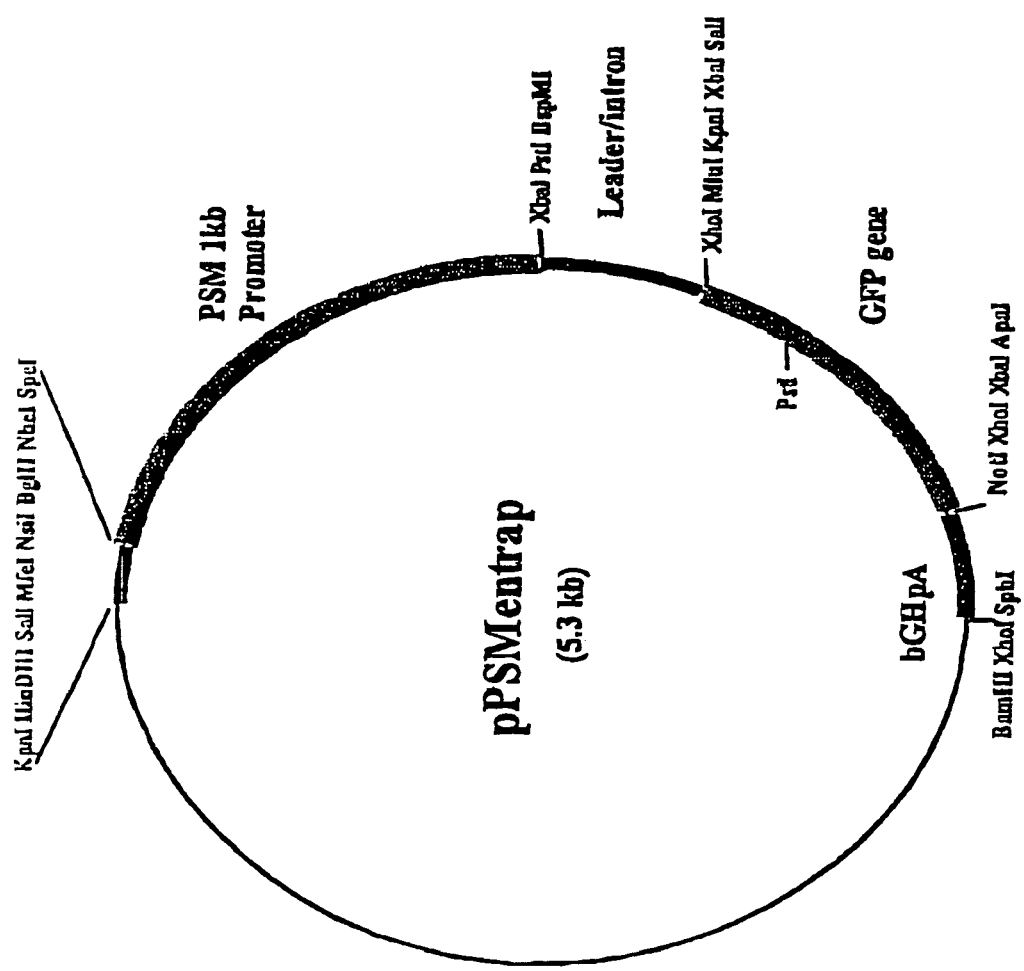
FIG. 1.

A strategy was developed to allow screening of DNA fragments for their ability to enhance transcription directed by the 1 kb proximal promoter region of the PSMA gene. The 1 kb promoter was cloned in front of the Green Fluorescent Protein (GFP) gene in the plasmid vector pPSMentrap shown in FIG. 1. Upstream of the promoter was inserted a polylinker region containing sites for cloning candidate fragments.

pPSMentrap contains the following elements: a polylinker containing restriction sites for the enzymes KpnL, HinDIII, SalI, MfeI, NsiI, BglI, NheI and SpeI, the PSMA promoter region stretching from base 1386 base 2560 (XbaI site) of the PSMA sequence (GENBANK Accession No. AF007544), a chimeric intron as contained in the pC1 vector (Promega), the GFP gene, the 3' end polyadenylation signal from the bovine growth hormone gene and the plasmid backbone (including ampicillin resistance gene and origin of replication) from the pC1 vector.

A library of DNA sequences was prepared by digesting the bacteriophage P1 cosmid P1-683 which contains the 5' half and upstream flanking sequence of the PSMA gene (40). Cosmid DNA was digested for various of times with the enzyme Tsp509I which cuts at AATT sites generating a range of partial digestion products. These were separated by agarose gel electrophoresis and fragments in the size range 1 to 2 kb recovered and cloned into the MfeI site of the pPSMentrap vector. A library of about 600 individual clones was picked.

Clones were grouped into 12 pools of 49 and DNA prepared from each pool using Qiagen columns and protocols. DNA (2.5 mg) from each pool was transfected into LNCaP cells in 3.5 cm dishes as previously described (1). After 48 to 72 hours, cell cultures were examined under a UV fluorescence microscope to identify any fluorescing cells. Positive pools were split into 7 by 7 matrices and DNA preparations made from the 7 clones in each row and each column. The transfections were repeated to identify positive sub-pools. Clones at the intersections of positive rows and columns were further screened individually to verify the expression of GFP. The three clones giving the strongest signals, #1, #3 and #4 were taken for further analysis.

Example 2

Location and Sequence Analysis of Enhancing Fragments

Figure 3:
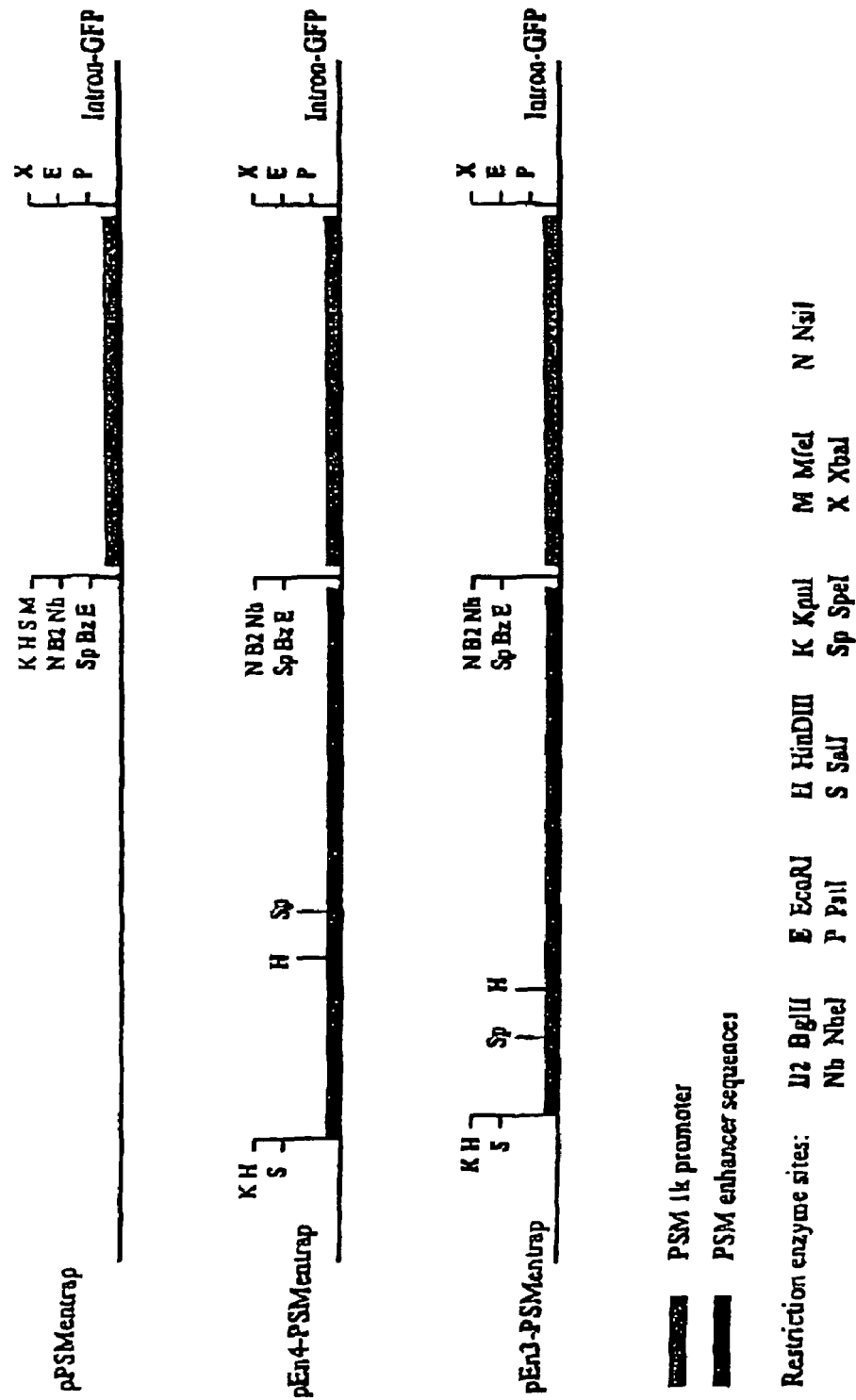

The inserts from the clones were re-cloned into PBLUESCRIPT SK+ (pBKSEn3 and pBKSEn4) cloning vectors and the sequences of their ends determined. All clones were found to originate from the third intron of the PSMA gene as shown in FIG. 2. The positions of both ends of clones #3 and #4 were identified as shown. The inserts in clones #3 and #4 were aligned in opposite orientations relative to the PSM promoter in the pPSMentrap vector as shown in FIG. 3. The clones share a common overlapping sequence of 1044 bp and extend in total over 2,530 bp. The third clone, #1, derived from the same region, one end being 6 bp upstream of the end of clone #4 and it also contained the SpeI and HinDIII sites contained in the region common to clones #3 and #4. It had, however, undergone some rearrangement on cloning and has not been further studied.

Example 3

Function of PSMA Enhancer Region

The activity of the PSMA enhancer region was first identified by visual inspection of fluorescence intensity of cells transfected with clones carrying PSMA gene inserts upstream of the PSM promoter. In these preliminary experiments it was also noted that the enhancer (clone #4) did not appear to function in the bladder cell line BL13 (not shown). In order to provide for quantitative determination of promoter and enhancer function, enhancers #3 and #4 (hereafter designated En3 and En4) in combination with the PSM 1 kb promoter were re-cloned into two different gene expression reporter systems.

Example 4

Expression Assayed in the pCAT3SAT System

Figure 4:
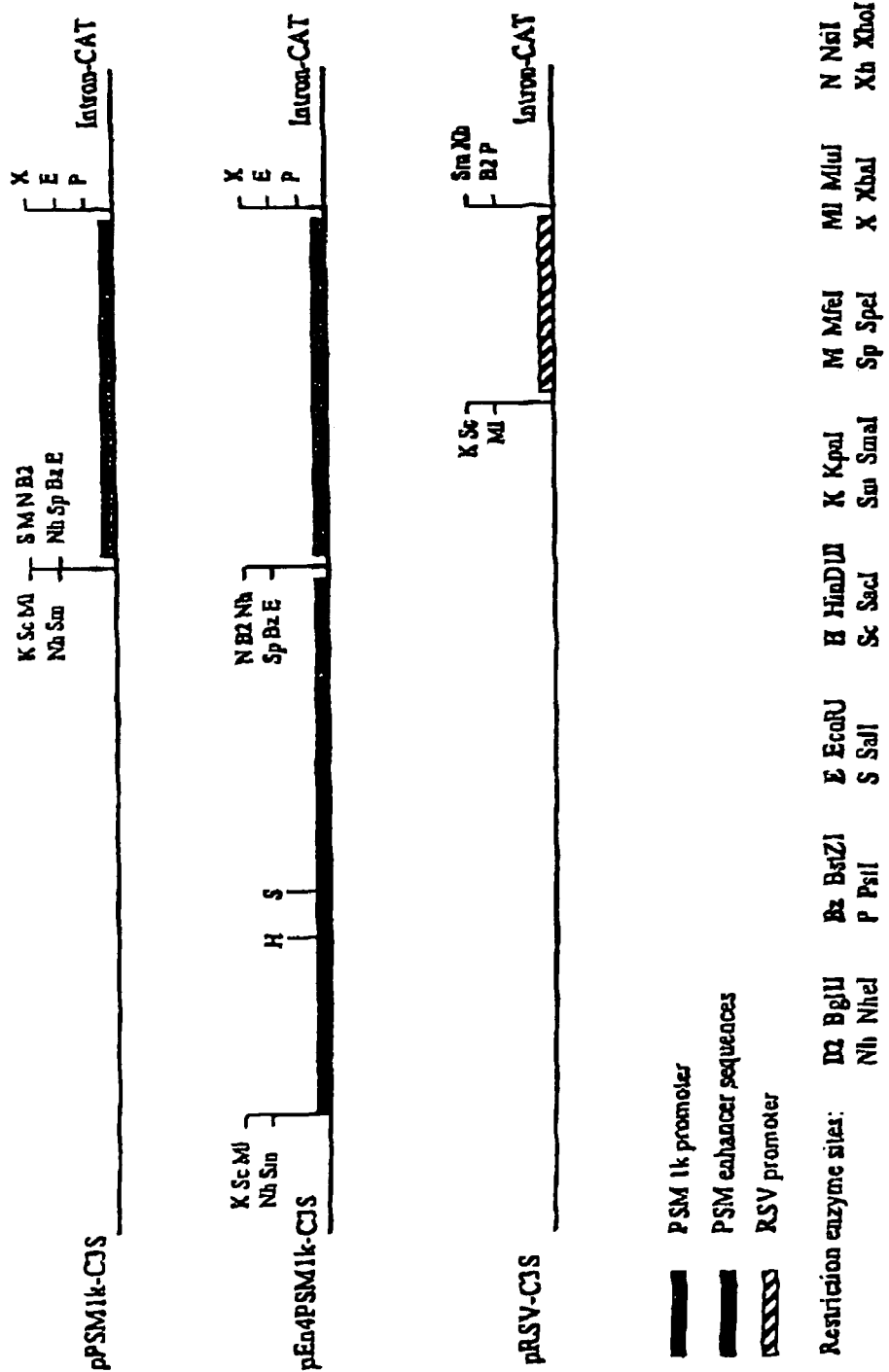
Figure 5:
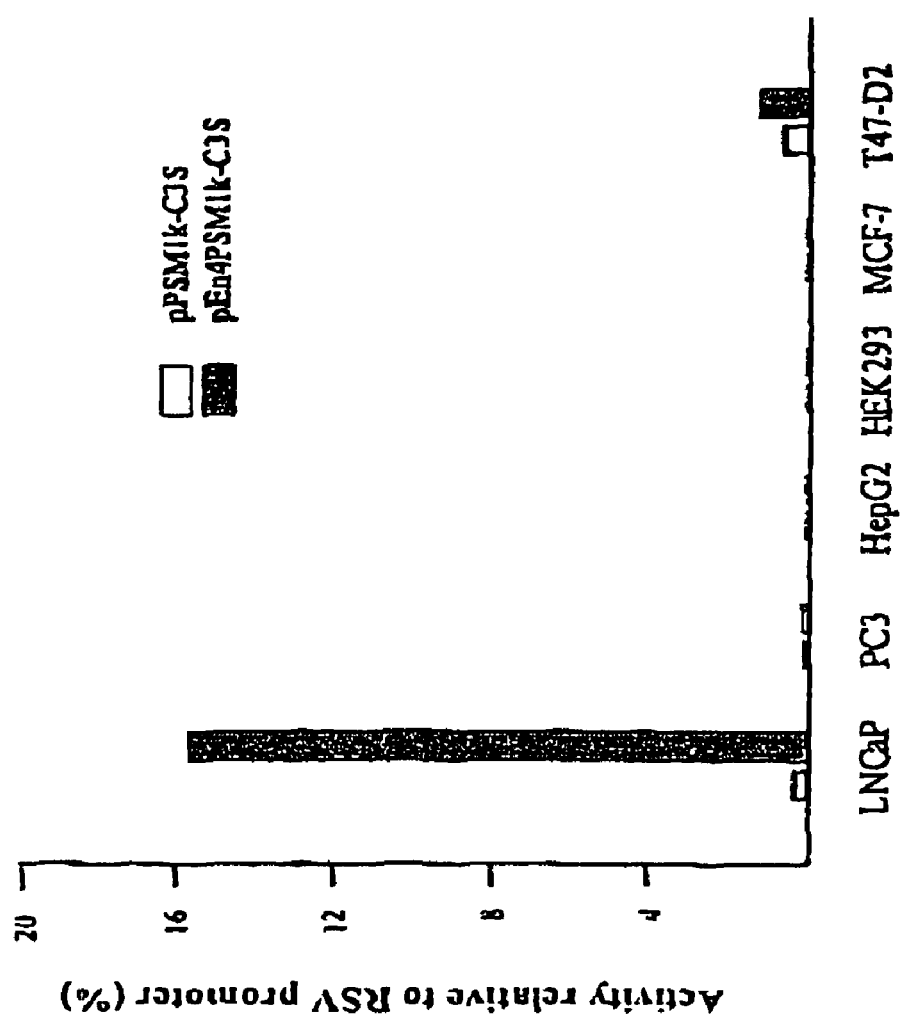

The pCAT3SAT vector contains a modified bacterial chloramphenicol acetyl transferase reporter gene for determining promoter activity and a reference reporter gene, serine acetyl transferase, under the control of the RSV promoter in order to standardise CAT expression for transfection efficiency. It was prepared by cloning the serine acetyl transferase reporter gene from the pCATSAT plasmid (1) as a SalI/BamHI fragment into BamHI, SalI cut pCAT3 vector (Promega). Constructs, pPSMlk-C3S and pEn4PSMlk-C3S, containing the PSM promoter with or without the PSM enhancer fragment 4 (En4) were prepared by cloning the PSM enhancer/promoter fragments as SalI/PstI fragments from the pPSMentrap vector into pCAT3SAT cut at the XhoI and PstI sites in the polylinker upstream of the CAT gene (FIG. 4). A control construct containing the RSV promoter, pRSV-C3S, was also prepared by blunt end ligation of a NaeI to SacI fragment from pCATSAT (1) into the NheI site of pCAT3SAT (FIG. 4). Cell lines were transfected with the different constructs and CAT and SAT activities determined after 48 h as described (1). The normalized expression data are shown in FIG. 5.

In LNCaP cells an enhancement of expression of approximately 50 fold (from 0.33% to 15.7% of the activity of the RSV promoter) was seen when the En4 fragment was present upstream of the 1 kb PSM promoter. This expression showed a high level of specificity for LNCaP cells that express PSMA. Another prostate cell line, PC3, showed very low levels of expression from the PSM promoter either in the presence or absence of the enhancer. No expression above background was seen for three non-prostate cell lines (MCF-7, a breast cancer line, human embryonic kidney cells (HEK293) and the liver line HepG2). Low and variable expression was seen in a second breast cancer cell line T47-D2, with the enhancer/promoter construct showing about 10% of the activity seen in LNCaP cells.

Example 5

Expression Assayed in the Luciferase pGL3 System

Figure 6:
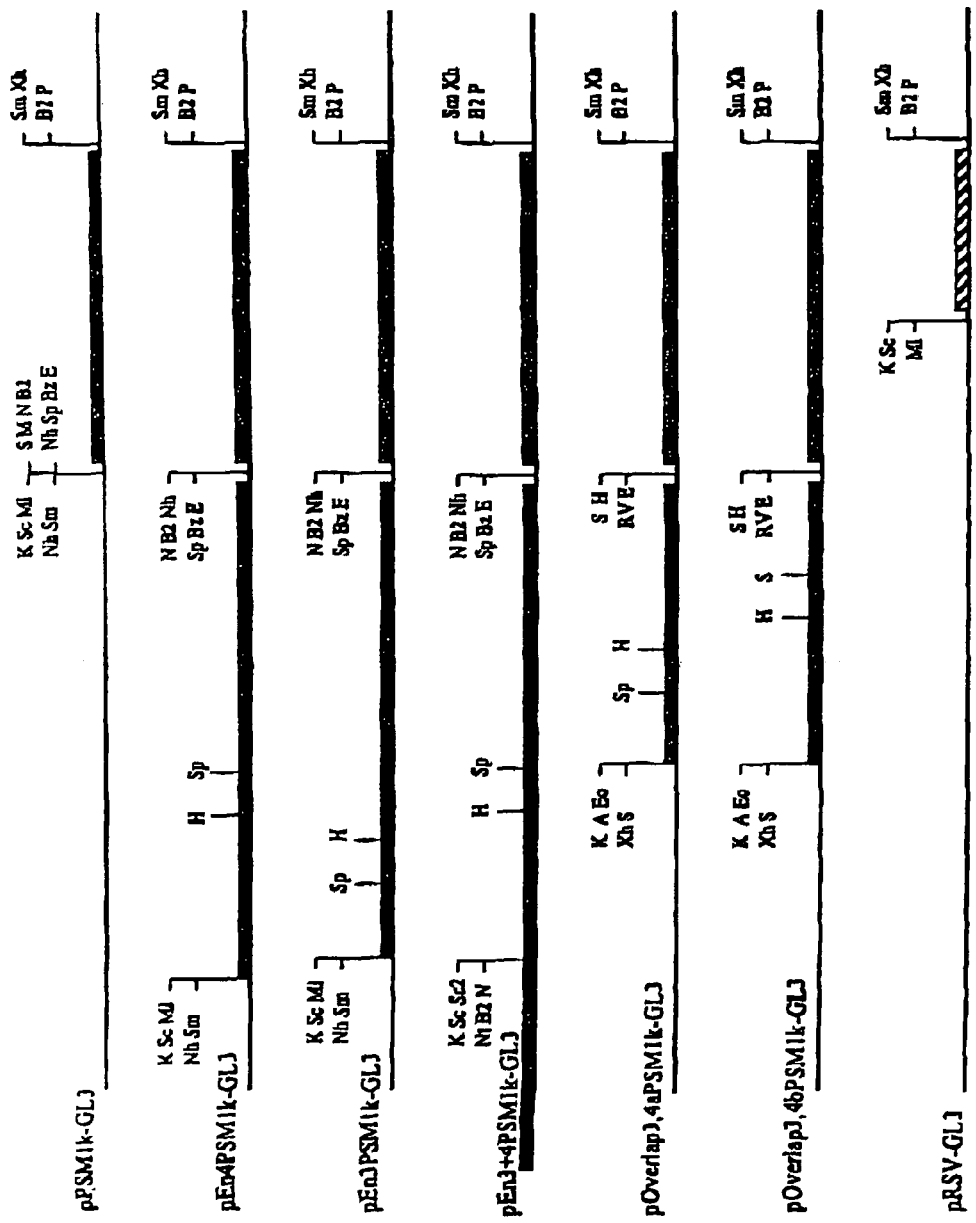

Because of the low activity of the PSM 1 KB promoter in the CAT assay system, promoter and enhancer sequences were cloned into the pGL3 vector (Promega) which contains the luciferase reporter gene. The structure of the clones is shown in FIG. 6. pPSMlk-GL3 and pEn4PSMlk-GL3 were prepared by cloning KpnI to XbaI fragments from pPSMlk-C3S and pEn4PSMlk-C3S respectively into pGL3 cut with KpnI and NheI. pEn3PSMlk-GL3 was prepared by cloning the KpnI to NheI enhancer fragment of pEn3PSMentrap into pEn4PSMlk-GL3 cut with KpnI and NheI. To assay activity, mixtures of each pGL3 construct and the reference plasmid pRSVCAT (1) were transfected into a variety of cell lines by standard procedures as described previously (1). DNA concentrations were determined by image analysis of ethidium bromide stained gels and master mixes prepared in the ratio of 1.5 μg of pGL3 construct to 1 μg of pRSVCAT. The same master mixes were used for transfections into all cell lines. Cells were transfected with 2.5 μg of DNA mixes using standard procedures (1) and expression assayed after 48 hr. Extracts were prepared and luciferase activity determined using the Luciferase Assay System (Promega).

Figure 7:
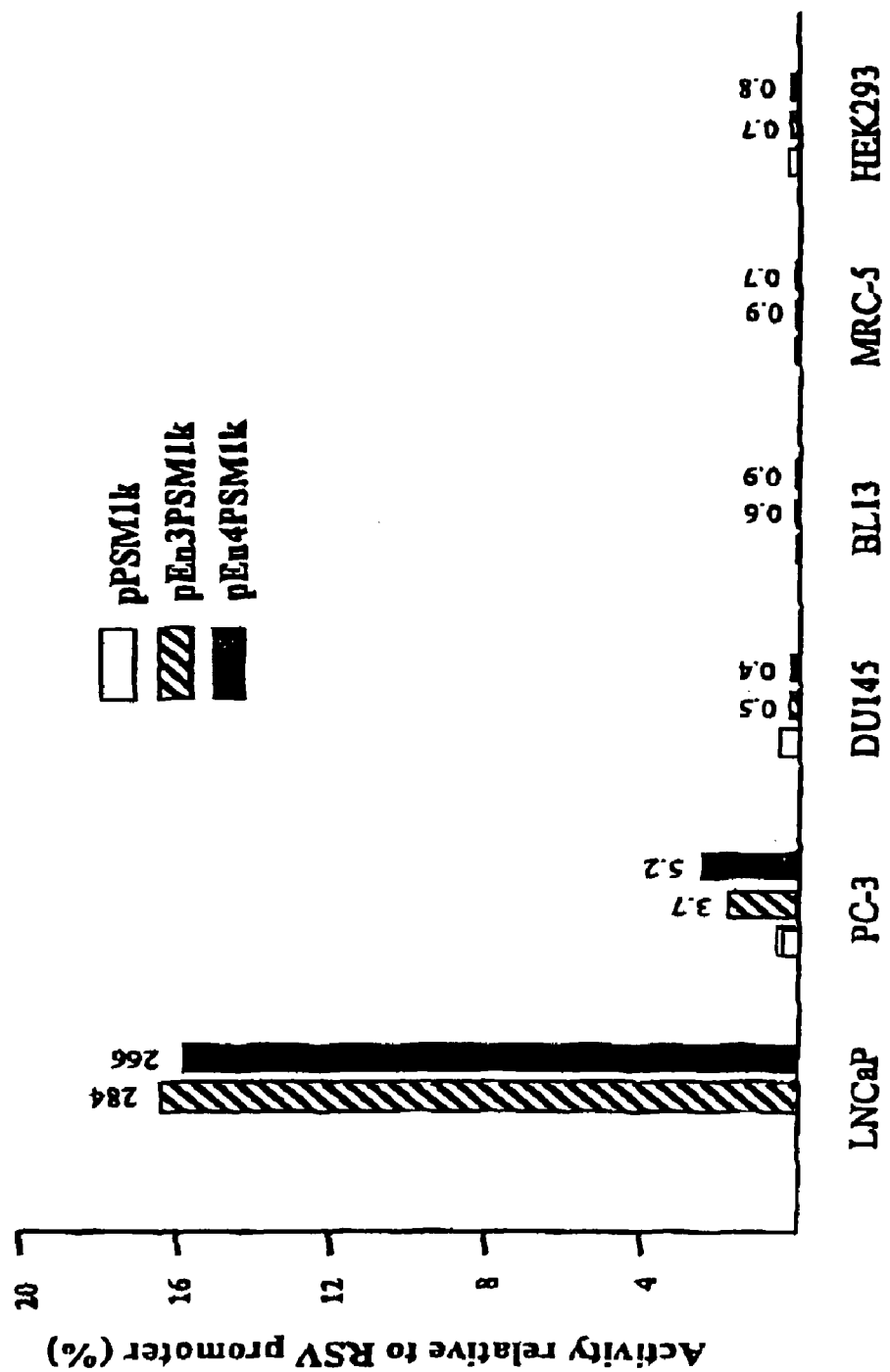

CAT activities were determined as previously described. Luciferase expression levels were standardised with respect to the pRSVCAT reference plasmid and then standardised activities expressed as a proportion of that of pRSV-GL3/pRSVCAT (FIG. 7).

In LNCaP cells expression from the PSM 1 k promoter was strongly enhanced by both En3 and En4 enhancer sequences (about 260 fold) with expression levels directed by pEn3PSMlk and pEn4PSMlk being 15 and 15.7% that of the RSV promoter. In the non-PSMA-expressing prostate cell line PC3 a low level of enhancement (3.7 and 5.2 fold for En3 and En4 respectively) was seen, while there was no enhancer function in the other non-expressing prostate line, DU145.

For a range of non-prostate cell lines tested, HepG2 liver cells, MRC5 primary lung fibroblasts, BL13 bladder carcinoma and human embryonic kidney HEK293 cells, essentially no activity was seen for the PSMA enhancer/promoter or promoter alone constructs. Activity is thus highly specific for the expressing prostate cell line LNCaP with partial enhancer function in one non-expressing prostate cell line PC-3.

Example 6

Characterisation of the Enhancer Element

To determine the extent of sequences required to provide enhancer activity a construct was prepared that contained all the sequences encompassed by clones En3 and En4 as well as constructs containing the overlapping region present in both cones (see FIG. 6). pEn3+4PSM1k-GL3 was prepared by cloning a KpnI to NdeI restriction fragment from pBKSEn3 into pEn4PSM1k-GL3 cut with KpnI and NDEI. Clone pOverlapen3/4a was prepared by cloning the San to HinDIII fragment from pEn3PSMentrap into PBLUESCRIPTSK+ cloning vector, subsequently cloning the HinDIII fragment from pEn4PSMentrap into the HinDIII site of the intermediate vector and verifying that it was in the correct orientation. The overlapping enhancer fragment was then cloned as a KpnI to EcoRI fragment in front of the PSM 1 kb promoter in pPSMlk-GL3 cut with KpnI and EcoRI. A construct with the overlapping region in the opposite orientation relative to the PSM promoter was likewise prepared by first cloning the SalI to HinDIII fragment from pEn4PSMentrap into PBLUE-SCRIPTSK+ cloning vector followed by the HinDIII fragment from pEn3PSMentrap and then cloning the overlap region in front of the PSM promoter as a KpnI to EcoRI fragment.

The effectiveness of these constructs was compared with that of the PSMlk promoter alone and the EN4/PSMlk promoter by transfection (as above) into LNCaP cells. Clones containing either orientation of the overlap region gave rise to expression levels similar to those containing En 4 sequences. The construct containing the whole region encompassed by enhancers 3 and 4, however, gave significantly stronger expression. The level of expression was about half that of the RSV promoter.

Example 7

PSMA Enhancer Action on Other Promoters

Figure 8:
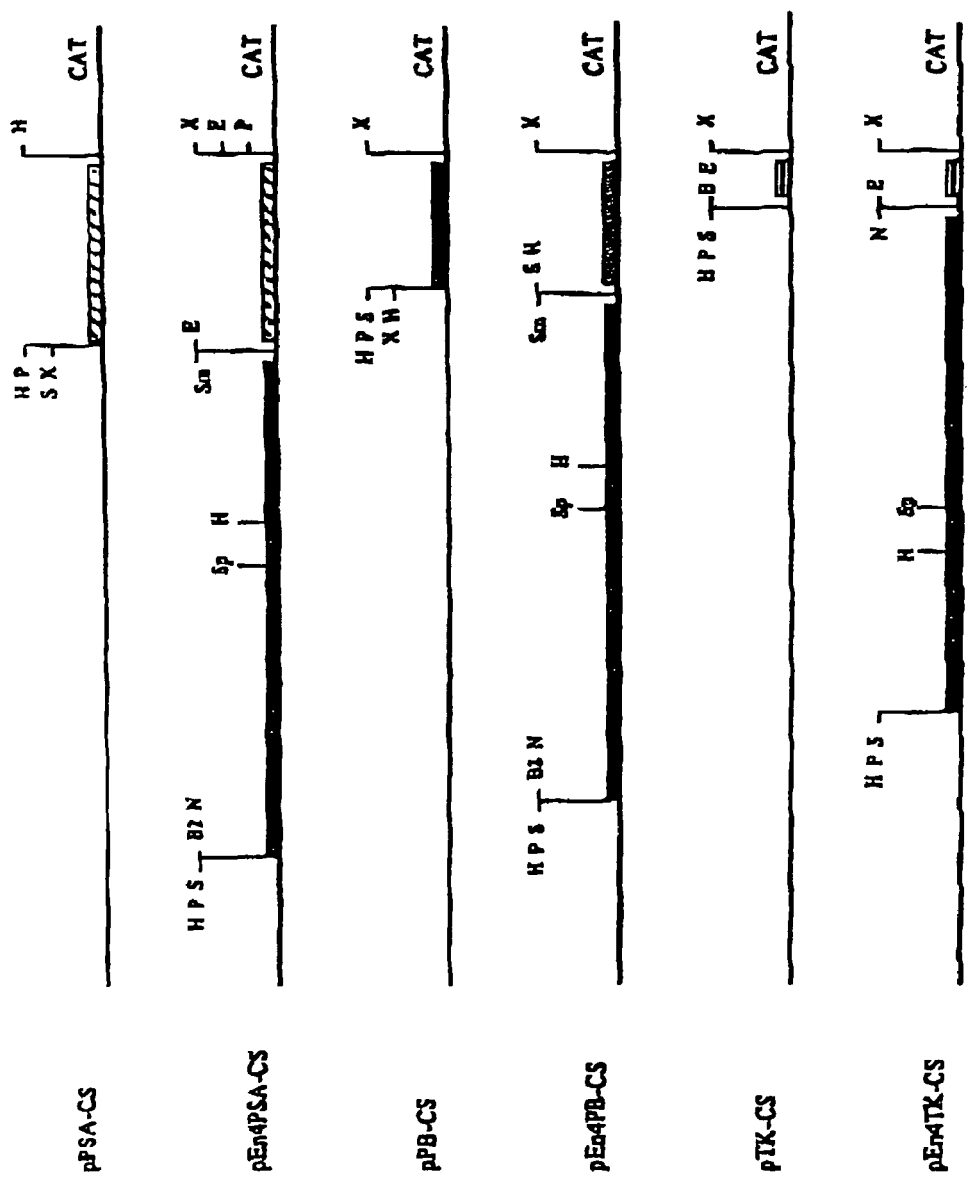

The properties of the enhancer were further assessed by linking it to other promoters, both those active primarily in prostate cells, PSA and probasin, and a non-tissue-specific promoter, that of the herpesvirus thymidine kinase gene (TK). The structures of these promoter regions are shown in FIG. 8. For the PSA and probasin constructs the enhancer region, En4, was cloned as an NheI fragment from the pEn4PSMlk-C3S plasmid into the XbaI-cut plasmids pPSA630 CATSAT and pPb430 CATSAT respectively (by partial digestion with XbaI for the probasin construct). pPSA630CATSAT and pPb430 CATSAT have been described previously (1). The plasmid pTKCATSAT. 1 was prepared by cloning the TK promoter region, bases −101 to +59, as a SalI to XhoI fragment into the SalI-cut vector pCATSAT. 1 (1) [pCATSAT. 1 is a derivative of pCATSAT (1) in which SalI, PstI and XhoI sites present upstream of the RSV promoter were removed or destroyed by XhoI and partial SalI digestion and religation]. pEn4TKCATSAT was prepared by cloning the SalI to BglII enhancer-containing fragment from pEn4PSMentrap into pTKCATSAT.1 cut with SalI and partially cut with BamHI.

Figure 9A:
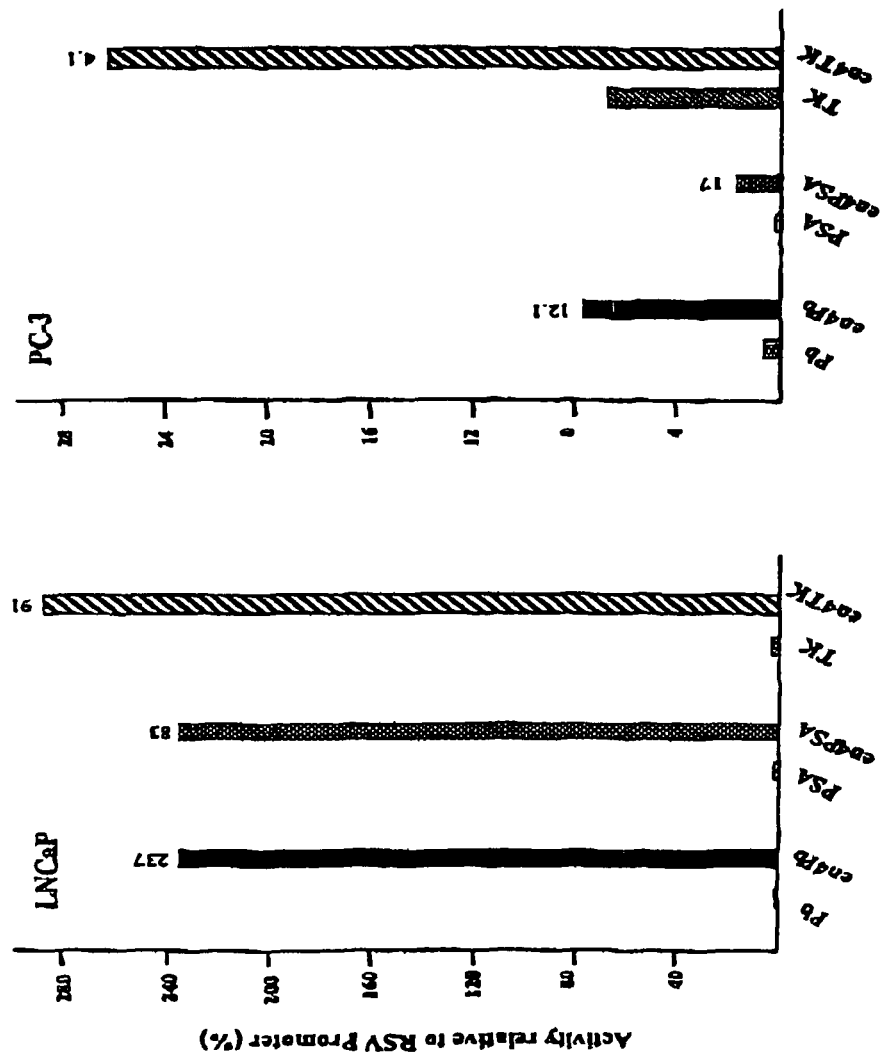
Figure 9B:
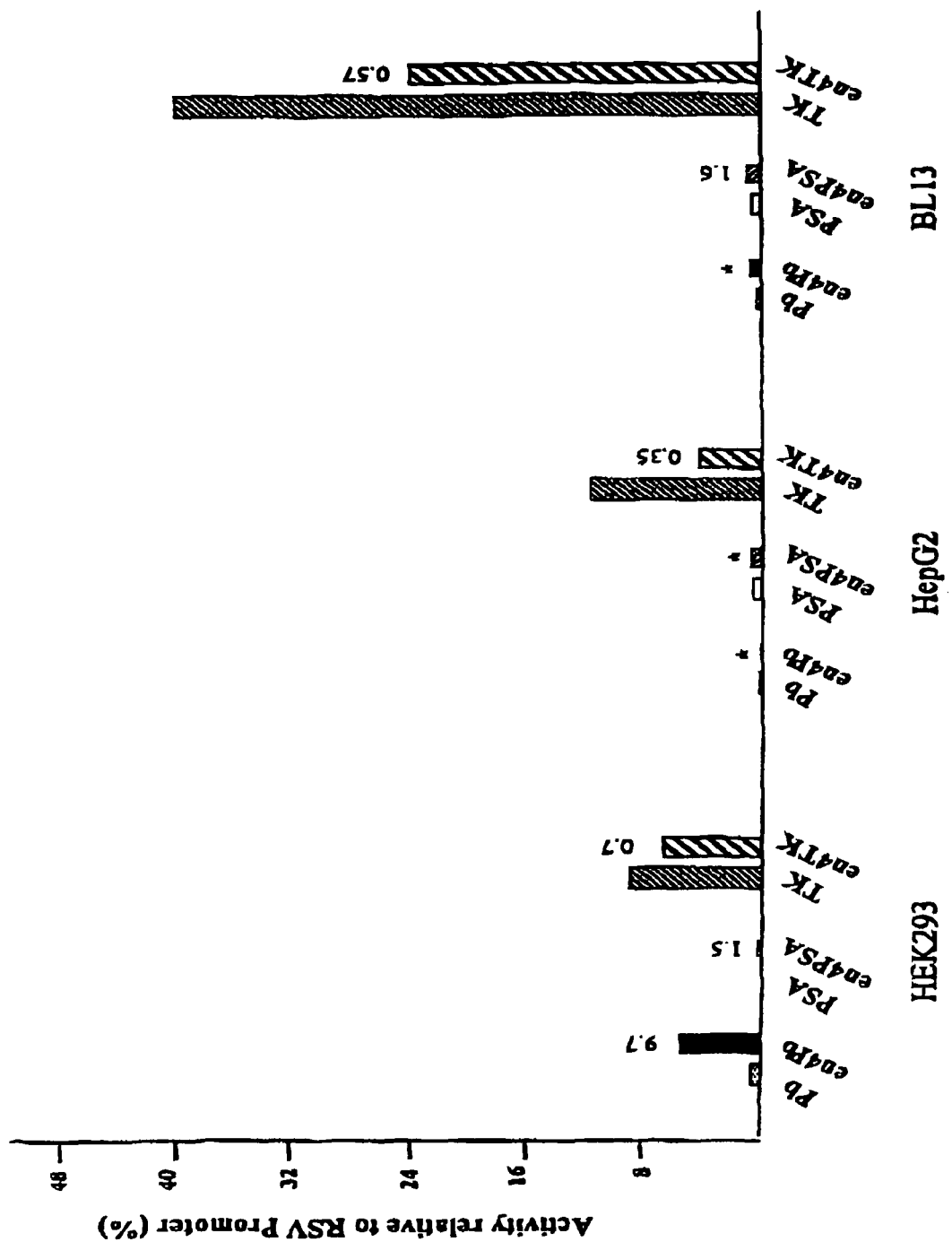
Figure 10:
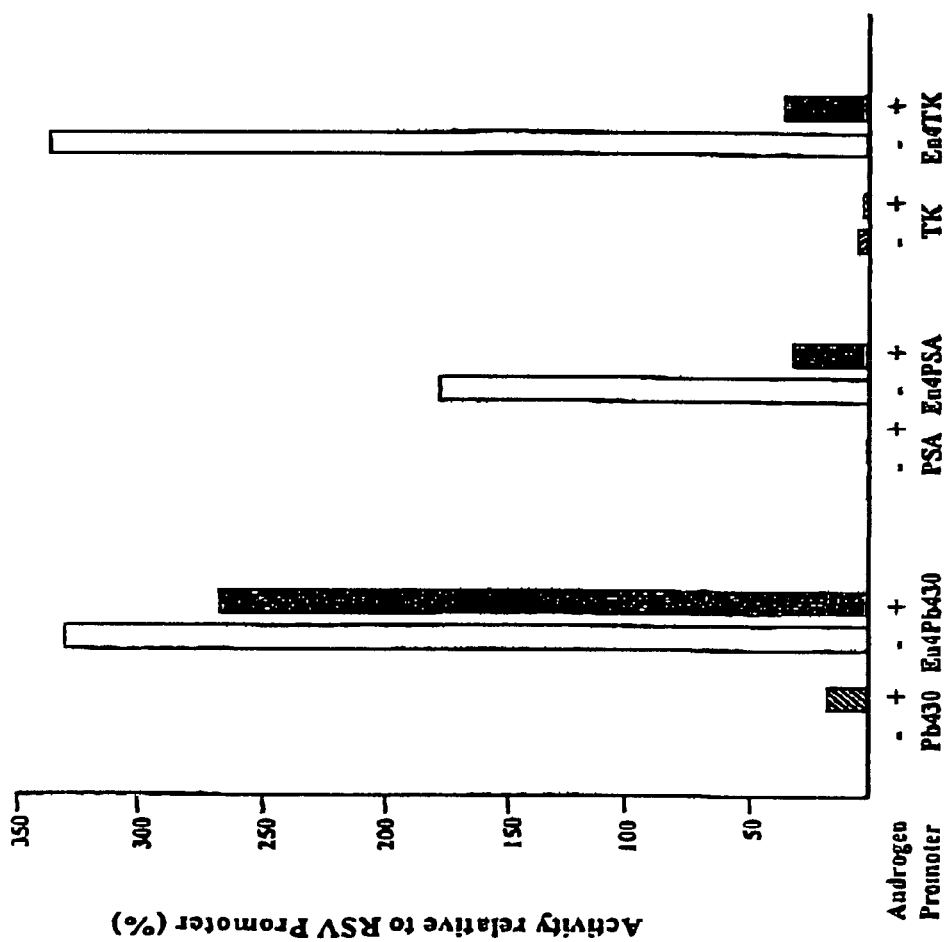

All six plasmids were transfected into a number of cell lines and CAT and SAT reporter gene expression determined as described (1). Expression levels were standardised against that of the RSV promoter determined by transfection of a standard mixture of pRSVCAT and pRSVSAT plasmids as described (1). Results are shown in FIGS. 9a & b.

In LNCaP cells strong enhancement of the PSA, probasin and TK promoters was seen, with that for probasin being strongest. Levels of expression for all enhancer constructs were 2 to 3 times that of the RSV promoter. Since all promoters achieved similar levels of expression in the presence of the enhancer the "fold-enhancement" shown probably reflects differences in the level of non-enhanced expression from the different promoters.

In PC3 prostate cells, which do not express PSMA, much reduced enhancement was seen, being 5 to 16 fold for the different promoters. This is similar to the results seen when the enhancer was joined with its own PSM promoter. Thus it appears that PC3 cells contain some factors that can interact with the PSM enhancer to activate transcription, but lack others, or do not have sufficient levels, to enable full enhancer function as is seen in LNCaP cells.

For the non-prostate cell lines, no enhancement was seen in HepG2 liver or BL13 bladder cells. Enhancement was seen in the embryonic kidney HEK293 cells. Low level enhancement (1.4, 1.5 fold) was seen for the PSA and TK promoters, while there was a stronger 9 fold enhancement of the probasin promoter. No enhancement by En4 of its homologous PSM promoter was seen in HEK293 cells (FIG. 7). Since the proximal kidney tubules are a site of low level PSMA expression, the expression seen in HEK293 cells may be biologically meaningful.

Example 8

PSM Enhancer Function does not Require Androgens

The androgen requirement for activity of the PSM enhancer (En4) was studied when it was linked to two highly androgen-inducible promoters, those of the probasin and PSA genes and one constitutive promoter, TK. LNCaP cells were transfected with plasmid constructs using media that had been charcoal stripped to remove androgens. Cells were maintained in androgen-free medium or incubated in the presence of the non-metabolizable androgen analogue, R1881 added to 0.28 nM (1). For all promoters strong enhancement of expression was seen whether or not androgen was present in the medium.

However, for all three constructs containing the PSM enhancer the level of expression actually decreased upon androgen addition. This suggests that the enhancer may contain sequences mediating the observed androgen-suppression of the endogenous PSMA gene.

Example 9

Sequences Required for Enhancer Function

In order to determine what sequence regions were critical for enhancer function a series of constructs were prepared in which different fragments from the PSME region were placed in front of the PSM promoter in the pPSMlk-GL3 plasmid. The sequences included in each construct are shown in the table below. The orientation of the enhancer sequences relative to the promoter is indicated as either F (forward, as for pEn4PSMlk-GL3) or R (reverse, as for pEn3PSMlk-GL3). Activity of these constructs was assayed following transfection into LNCaP cells along with the pRSVCAT control plasmid. Extracts were prepared and assayed 48 hr after transfection, luciferase activity normalized using the activity of the co-transfected pRSVCAT plasmid and expressed relative to that of pRSV-GL3 (Table below).

| Construct | Enhancer sequences | Activity in LNCaP cells (% RSV) |
|---|---|---|
| pPSMlk-GL3 | | 0.2 |
| pEn4PSMlk-GL3 | 14760-16575 F | 16.0 |
| pEn3PSMlk-GL3 | 14045-15804 R | 15.7 |
| pEn3 + 4PSMlk-GL3 | 14045-16575 F | 39 |
| pEn3/4aPSMlk-GL3 | 14760-15804 F | 25 |
| pEn3/4bPSMlk-GL3 | 15804-14760 R | 21 |
| pEn4Sal/HindIIPSMlk-GL3 | 14760-15374 F | 20 |
| pEn3Sal/HindIIIPSMlk-GL3 | 15804-15369 R | 0.1 |
| pEnO2/770SpeIPSMlk-GL3 | 14760-15530 F | 24 |
| pEnO2/2/592NsiIPSMlk-GL3 | 14760-15352 F | 22 |
| pEnO2/445MscIPSMlk-GL3 | 14760-15205 F | 18 |
| pEnO2/331SmaIPSMlk-GL3 | 14760-15091 F | 26 |
| pEnO2/168NdeIPSMlk-GL3 | 14760-14930 F | 6 |
| pEnO1/722SmaIPSMlk-GL3 | 15092-15804 R | 0.3 |
| pEnO1/886NdeIIPSMlk-GL3 | 14925-15804 R | 0.4 |

These data indicate that most of the enhancer activity is contained within the 331 bp region encompassing bases 14760 to 15091. This region shows similar activity (26% that of RSV) to the En3 and En4 clones and to the approximately 1 kb region shared between them. Deletion from the 1 kb overlap region of either the left half or the entire 331 bp region (constructs pEnO1/722smaIPSMlk-GL3 and pEnO1/886NdeIIPSMlk-GL3) eliminates enhancer activity, showing that this region is essential for activity. Elimination of the right half of the 331 bp region, leaving just 170 bp covering bases 14760 to 14930, leads to a marked reduction in activity.

Thus bases 14760 to 14930 are essential for PSME function, but sequences extending from 14760 to 15091, provide for much stronger enhancer activity. The sequence of the region is shown in FIG. 11.

Example 10

PSME Core Enhancer Region Retains Cell-Type Specificity

Experiments were carried out on the 331 bp core region of the PSME that provides for enhancer function (bases 14760 to 15091) to determine whether this region retained its cell-type specificity. The activity of plasmids pPSMlk-GL3, pEn02/331SmaIPSMlk-GL3 and pRSV-GL3 was assayed after transfection into a number of cell lines (Table below). Plasmids were co-transfected with an internal control pRSVCAT plasmid, extracts prepared and assayed 48 h after transfection. Luciferase activities were normalized using the activity of the pRSVCAT plasmid and are expressed relative to that of pRSV-GL3.

| | Activity Relative to the RSV promoter (%) | | | | |
|---|---|---|---|---|---|
| Construct | PC-3 | DU145 | MCF7 | MRC5 | HepG2 |
| pPSMlk-GL3 | 0.45 | 0.21 | 0.12 | 0.032 | 0.033 |
| PEn02/33 1SmaIPSM1k-GL3 | 1.70 | 0.13 | 0.14 | 0.048 | 0.022 |

As for the longer enhancer fragments, partial enhancer activity was seen in the PC-3 prostate cancer cell line that does not express PSMA. For the other non-PSMA expressing prostate cell line, DU145, no enhancement of basal promoter activity was seen. Likewise the 331 bp PSME core region is not functional in three non-prostate cell lines. The core region thus retains the specificity of the PSME.

Example 11

Tandem Enhancer Sequences Provide for Greater Activity

Figure 14:
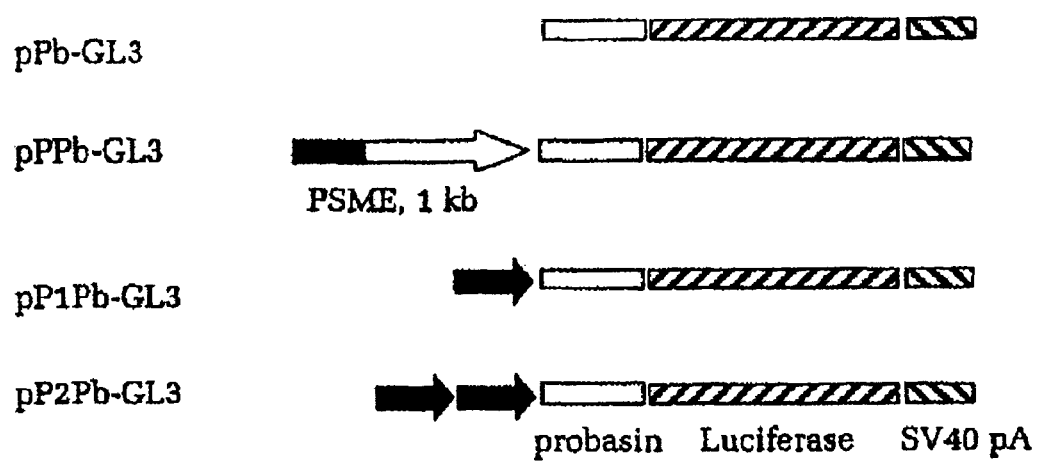

A series of constructs were prepared in which the probasin promoter, with or without PSM enhancer fragments was subcloned in front of the luciferase reporter gene in the pGL3 vector. The structure of the constructs is shown in FIG. 14. The 430 bp probasin promoter fragment has been described previously (1) and was re-cloned from the pPB-CS plasmid (see FIG. 8). pPPb-GL3 contains the 1 kb overlapping enhancer region (bases 14760 to 15804). pP1Pb-GL3 and pP2PPb-GL3 contain one or two copies respectively of the 331 bp enhancer region (bases 14760 to 15091). All enhancer sequences are in the forward orientation.

The constructs were transfected, along with an RSVCAT control plasmid, into LNCaP, HEK293 or MCF-7 cells and expression measured in cell extracts prepared after 48 h incubation. Transfections were done in androgen-depleted media and luciferase activity corrected using the co-transfected RSVCAT internal control.

| | Relative Luciferase Activity | | |
|---|---|---|---|
| | LNCaP | HEK293 | MCF-7 |
| pPb-GL3 | 1.45 | 2.36 | 0.36 |
| pPPb-GL-3 | 246 | 2.17 | 1.09 |
| pP1Pb-GL-3 | 346 | 3.2 | 0.73 |
| pP2Pb-GL-3 | 798 | 1.8 | 5.75 |
| pRSV-GL-3 | 318 | 277 | 107 |

Greatest expression in LNCaP cells is seen with the double enhancer construct, being 2 to 3 times greater than those constructs with a single copy of the enhancer. Specificity of expression is largely maintained in these transfection studies, though the pP2Pb-GL3 construct shows an elevated level of expression in MCF-7 cells.

Example 12

Enhancer Function in a Viral Backbone

The properties of the PSME combined with the probasin promoter (its high activity and specificity and limited responsiveness to androgen levels) are particularly suitable for directing prostate-specific gene expression in gene therapy applications.

Figure 15:
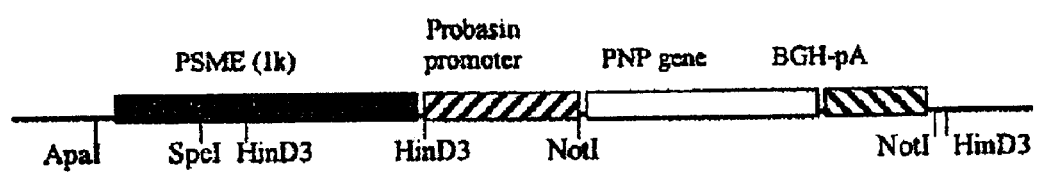

The *E. coli* purine nucleoside phosphorylase (PNP) gene in combination with the pro-drugs fludarabine or 6-methylpurine 2-deoxyriboside (6 MPDR) can be used to deliver enzyme pro-drug therapy (41). An expression cassette was prepared in the pGEM11 plasmid in which the PNP gene was placed under the control of the 1 kb PSME region (bases 14760 to 15804 in reverse orientation) adjacent to the 430 bp probasin promoter. A map of this construct (pPPP (for Psm/Probasin/PNP)) is shown in FIG. 15. The cassette in pGEM11 was partially sequenced to confirm its structure The expression cassette was subcloned by cutting with ApaI and NotI (partial digest for NotI) and inserting into ApaI/NotI cut ovine adenovirus (OAV) vectors (42). The expression cassette was inserted into two separate sites in the OAV plasmid. One isolate was prepared by cloning into OAV200 cut with ApaI and NotI (Site 1) to give clone pOAV223. In the other isolate, pOAV623, the cassette was cloned in an alternate site (Site 3) of the plasmid POAV600 (42). Plasmid DNA was transfected into CSL503 cells as described (43) and viruses OAV223 and 623 recovered.

Figure 12:
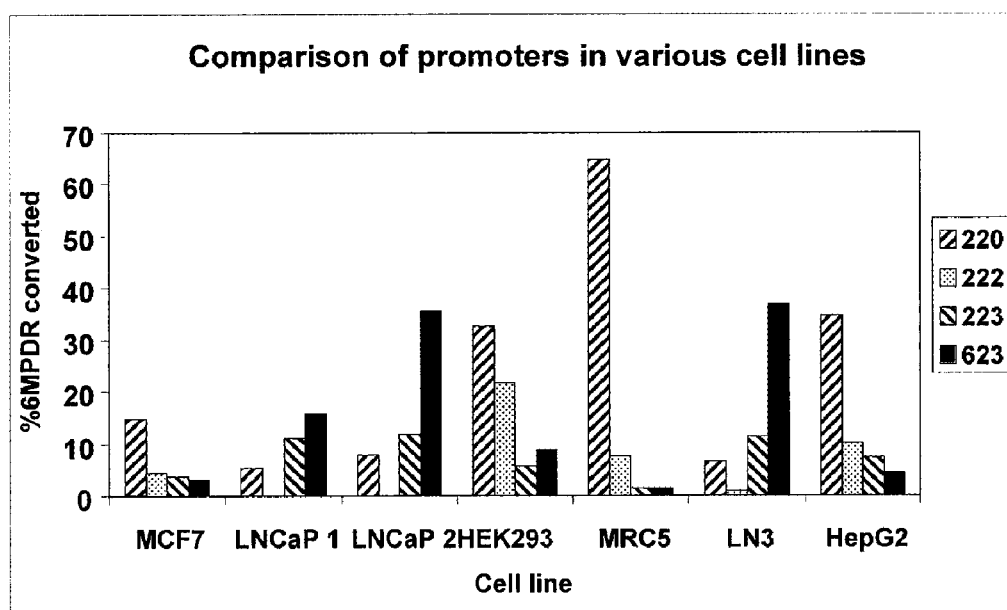

OAV223, OAV623 and two other viruses OAV220 and OAV222, that are equivalent to OAV223 except that the PNP gene is under the control of the RSV and CMV promoters respectively, were used to infect a variety of cell types as shown in FIG. 12. Cells were infected with the different viruses at a multiplicity of infection of $10^3$ opu/cell and PNP expression measured after 4 days (44). For each cell type an amount of lysate was used such that PNP expression from the most strongly expressing virus fell within the linear range of the assay. Thus, the absolute amount of PNP activity cannot be compared between cell lines but ratios of expression can be compared.

The data presented in FIG. 12 show that in the context of the viral backbone and OAV infection strong specificity of gene expression is maintained. Highest activity is seen from OAV623, then OAV223, being greater than that of the RSV promoter in LNCaP and LN3 prostate cancer cells. In all the non-prostate cell lines the RSV promoter (OAV220) provides strongest expression. The differential specificity of the PSME/Pb promoter versus the RSV promoter for prostate compared to non-prostate cells ranges from expression about 15 fold for HEK293 and MCF-7 through to 200 fold for MRC-5). Thus, in some cell types specificity is reduced in the OAV context but it is still substantial. In the following example retention of cell specificity of the PSME in combination with its own PSM promoter is also demonstrated when carried by a human adenovirus Type 5.

Example 13

Enhancer Function in Human Umbilical Artery Cells

PSMA has been shown to be expressed in the neovasculature of a range of tumour types, but not in normal vasculature. We have determined, using reverse transcriptase PCR, that PSMA is expressed in endothelial cells derived from the human umbilical artery (HUAECs) (data not shown). Other genes that are up-regulated in tumour vasculature are also expressed in HUAECs and related human umbilical vein cells (HWECs), e.g. endoglin (45). Function of PSM regulatory sequences was therefore examined in these cells. The activity of the PSME coupled to the PSM 1 kb promoter was evaluated using a replication-defective adenovirus, human adenovirus Type 5, into which the expression cassette from the pPSMentrap vector with the En4 insert had been inserted. The virus, Ad525, carries the GFP gene with bovine growth hormone 3' polyadenylation sequences under the transcriptional control of PSME En4 sequences coupled to the PSM 1 kb promoter. A control virus, Ad526, in which the GFP gene was under the control of the ubiquitously-active EF-1 promoter was also used.

HUAECs and HUVEGs were dissociated from umbilical arteries and cultured as described by Underwood and Bean (46) except that tissue culture dishes were coated with bovine, rather than chicken, fibronectin. HUACs, HUVECs, LNCaP and control human lung fibroblast MRC-5 cells were plated at $4×10^4$ cells per chamber in fibronectin-coated microscope slide chambers. The following day they were infected with $5×10^8$ optical particle units per chamber of either Ad525 or Ad526. Expression of the GFP gene was monitored by fluorescence microscopy 3 days after infection for the control Ad526 virus and after 6 days for the PSME driven Ad525.

Expression from the control virus (EIF, OAV526) was strong in all cell types. For the En4PSMGFP virus, clear expression was seen in HUAECs and LNCaP cells, weaker expression in HUVECs, but no expression could be detected in MRC-5 cells. The combination of PSME and the PSM promoter is thus able to specifically drive gene expression in these arterial cells that express the endogenous PSM gene and should prove useful in directing expression to tumour vasculature.

Example 14

Construction and Stability of OAdV Expressing Green Fluorescent Protein

The plasmid pOAdV217A, containing the HCMV/GFP cassette in site I was constructed as follows. The coding portion of the GFP gene was blunt-cloned into the XhoI/SmaI sites of plasmid pCI (Promega Corp, Madison Wis.) to place it under the control of the HCMV promoter. The entire cassette was excised by BglII/BamHI digestion and blunt-cloned into the XbaI site of pGem11zf (Promega Corp, Madison Wis.). A clone with a 5' ApaI and 3' NotI site was selected and the insert was cloned into these sites in pOAV200 (site I insertion) for virus rescue (Vrati et al., 1996b). Subsequently, the cassette was further subcloned and modified by AflII digestion and blunt end ligation to remove the intron provided in pCI. The virus was rescued after transfection of CSL503 cells as described previously (Vrati et al., 1996b) except that cationic lipids were used (Cameron et al., 1999) in place of lipofectamine. The virus proved difficult to rescue and several attempts were made. On the third attempt a cytopathic effect developed and medium from the cells was transferred to fresh permissive CSL503 cells to grow a stock of the virus (OAdV217A). The virus was subsequently passaged to expand the stock. Viral DNA was extracted from a portion of each passage, digested with BamHI and analysed by agarose gel electrophoresis. Passage 1 virus had a similar amount of the 3.1 kb band that was diagnostic for the cassette compared to the starting plasmid from which the virus was rescued. However, by passage three this band was significantly depleted relative to the band immediately above it and a smaller product of ~1.7 kb had appeared, demonstrating the instability of this particular genome. PCR amplification across the site of the inserted cassette and nucleotide sequencing revealed that a variety of deletion events had resulted in the loss of all or part of the HCMV promoter and the GFP coding and polyadenylation sequence.

Example 15

Figure 13:
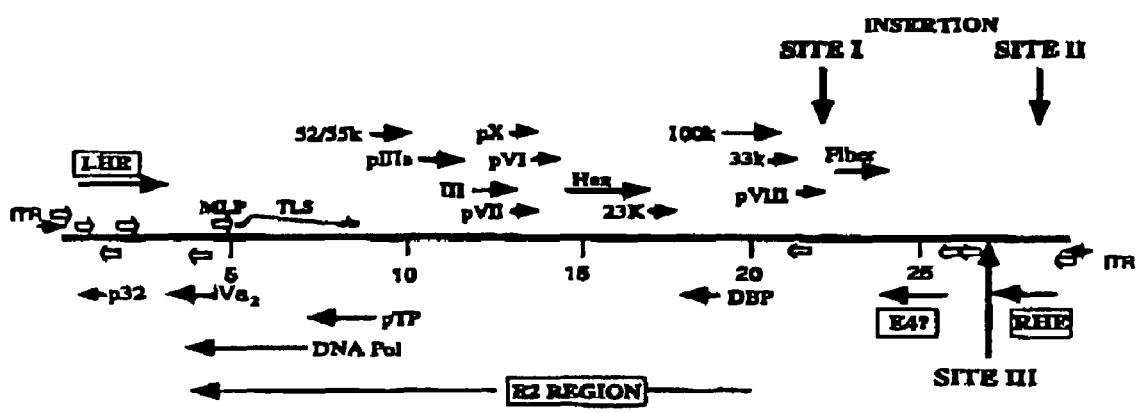

Construction and Stability of OAdV Carrying an HCMV Alkaline Phosphatase Cassette Two plasmids, pOAdV216 and pOAdV616, were constructed in which a cassette containing the HCMV promoter and human placental alkaline phosphatase sequences was inserted in site I or site III of the genome, respectively (see FIG. 13). The corresponding viruses were rescued and passaged in CSL503 cells. From gel electrophoresis it was apparent that the 1.95 and 1.8 kb bands representing the cassette in OAdV216 were lost rapidly after passage two and by passage two had been replaced by a ~1.4 kb band. For OAdV616 however, the genome is stable. The diagnostic 1.8 kb band was retained, even after four passages.

Example 16

Construction and Stability of an OAdV Carrying Cassettes for Prostate Cancer Gene Therapy A series of plasmids was constructed in which different promoters were linked to the purine nucleoside phosphorylase gene from *E. coli* and the polyadenylation signal of bovine growth hormone. The plasmids pOAdV220 and 222 contained the promoter from Rous sarcoma virus and HCMV, respectively. Plasmids pOAdV223 and 623 contained a prostate-specific promoter/enhancer element derived from the prostate-specific membrane antigene gene linked to the promoter the rat probasin gene promoter. These cassettes were inserted in the left to right orientation into the ApaI/NotI sites of pOAdV200 (site I) and pOAdV600 (site III), respectively. The corresponding virus from each of the above plasmids was rescued and passaged three times in CSL503 cells. DNA from each virus was analysed by Southern hybridisation using a radio-labelled 1.1 kb AgeI fragment from pOAdV220 as a probe. This contained the 3' end of the RSV promoter, all of the PNP and BGH sequences and ~300 bp of 3' OAdV genome sequence. The expected bands representing each respective cassette and the 3' BamHI fragment were observed for wild-type OadV, OAdV220, 223 and 623. However, for OAdV222 which contained the HCMV cassette in site I, the expected band was reduced in intensity and an additional smaller band was seen, indicating genome instability. Thus, site III is the preferred site for insertion of foreign gene cassettes. As site III is located between recently defined transcription units (Khatri and Both, 1998) the insertion of a discrete transcription cassette may not interfere with other viral functions. With this precedent, it is anticipated that expression cassettes could also be inserted into the OAdV genome between the Left Hand End and IVa2 transcription units (see FIG. 13).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Brookes, D. E., D. Zandvliet, F. Watt, P. J. Russell and P. L. Molloy (1998) relative activity and specificity of promoters from prostate-expressed genes. The Prostate 35: 18-26
2. Cleutjens, K. B. J. M., C. C. E. M. Vaneekelen, H. A. G. M. Vanderkorput, A. O. Brinkmann and J. Trapman. (1996). "Two androgen response regions cooperate in steroid hormone regulated activity of the prostate-specific antigen PROMOTER." J Biol Chem. 271 (11): 6379-6388.
3. Riegman, P. H. J., R. J. Viestra, J. A. G. M. van der Korput, A. O. Brinkmann and J. Trapman. (1991). "The promoter of the prostate-specific antigen gene contains a functional androgen responsive element." Molec. Endocrinology. 5 (12): 1921-1930.
4. Murtha, P., D. J. Tindall and C. Y. F. Young. (1993). "Androgen induction of a human Prostate-Specific kallikrein, hKLK2-characterization of an androgen response element in the 5' promoter region of the gene." Biochemistry. 32 (25): 6459-6464.
5. Claessens, F., N. K. Rushmere, P. Davies, L. Celis, B. Peeters and W. A. Rombauts. (1990). "Sequence-specific binding of androgen-receptor complexes to prostatic binding protein genes." Mol. Cell. Endocrinol. 74: 203-212.

6. Rushmere, N. K., M. G. Parker and P. Davies. (1987). "Androgen-receptor binding regions of an androgen responsive gene." Mol. Cell. Endocrinol. 51: 259-265
7. Kasper, S., P. S. Rennie, N. Bruchovsky, P. C. Sheppard, H. Cheng, L. Lin, R. P. C. Shiu, R. Snoek and R. J. Matusik. (1994). "Cooperative binding of androgen receptors to two DNA sequences is required for androgen induction of the probasin gene." J. Biol. Chem. 269 (50): 31763-31769.
8. Rennie, P. S., N. Bruchovsky, K. J. Leco, P. C. Sheppard, S. A. MCQUEEN, H. Cheng, R. Snoek, A. Hamel, M. E. Bock, B. S. MacDonald, B. E. Nickel, C. Chang, S. Liao, P. A. Cattini and R. J. Matusik. (1993). "Characterization of two cis-acting DNA elements involved in the regulation of the probasin gene." Molec. Endocrinol. 7 (1): 23-36.
9. Virkkunen, P., P. Hedberg, J. J. Palvimo, E. Birr, K. Porvari, M. Ruokonen, P. Taavitsainen, O. A. Janne and P. Vihko. (1994). "Structural comparison of human and rat prostate-specific acid phosphatase genes and their promoters: identification of putative androgen response elements." Biochem. and Biophys. Res. Commun. 202 (1): 49-57.
10. Celis, L., F. Claessens, B. Peeters, W. Heyns, G. Verhoeven and W. Rombauts. (1993). "Proteins interacting with an androgen-responsive unit in the C3 (1) gene intron." Mol. Cell. Endocrinol. 94: 165-172.
11. Ho, K. C., K. B. Marschke, J. A. Tan, S. G. A. Power, E. M. Wilson and F. S. French. (1993). "A complex response element in intron-1 of the Androgen-Regulated 20-kDa protein gene displays cell Type-Dependent androgen receptor specificity." J Biol Chem. 268 (36): 27226-27235.
12. Zhang, Y.-L., M. G. Parker and O. Bakker. (1990). "Tissue-specific differences in the binding of nuclear proteins to a CCAAT motif in the promoter of the androgen-regulated C3 gene." Molec. Endocrinol. 4 (8): 1219-1225.
13. Allison, J., Y.-L. Zhang and M. G. Parker. (1989). "Tissue-specific and hormonal regulation of the gene for rat prostatic steroid-binding protein in transgenic mice." Mol. Cell. Biol. 9: 2254-2257.
14. Maroulakou, I. G., M. Anver, L. Garrett and J. E. Green. (1994). "Prostate and mammary adenocarcinoma in transgenic mice carrying a rat c3 (1) simian virus 40 large tumor antigen fusion gene." Proc Natl Acad Sci USA. 91 (23): 11236-11240.
15. Greenberg, N. M., F. J. Demayo, P. C. Sheppard, R. Barrios, R. Lebovitz, M. Finegold, R. Angelopoulou, J. G. Dodd, M. L. Duckworth, J. M. Rosen and R. J. Matusik. (1994). "The rat probasin gene promoter directs hormonally and developmentally regulated expression of a heterologous gene specifically to the prostate in transgenic mice." Mol Endocrinol. 8 (2): 230-239.
16. Matusik, R. J. Isolated DNA mol. contg. an androgen responsive element comprising a 5'-flanking region of the rat probasin gene, used to generate transgenic animals and for human prostate cancer therapy. International publication no. WO 94/03594
17. Greenberg, N. M., F. Demayo, M. J. Finegold, D. Medina, W. D. Tilley, J. O. Aspinall, G. R. Cunha, A. A. Donjacour, R. J. Matusik and J. M. Rosen. (1995). "Prostate cancer in a transgenic mouse." Proc Natl Acad Sci USA. 92 (8): 3439-3443.
18. Gingrich, J. R., R. J. Barrios, M. W. Kattan, H. S. Nahm, M. J. Finegold and N. M. Greenberg (1997) Androgen independent prostate cancer progression in the TRAMP model. Cancer Res. 57: 4687-4691.
19. Schaffner, D. L., R. Barrios, M. R. Shaker, S. Rajagopalan, S. L. Huang, D. J. Tindall, C. Y. F. Young, P. A. Overbeek, R. M. Lebovitz and M. W. Lieberman. (1995). "Transgenic mice carrying a PSArasT24 hybrid gene develop salivary gland and gastrointestinal tract neoplasms." Lab Invest. 72 (3): 283-290.
20. Belldegrun, A. S. and S. Pang. "Nucleic acid contg. prostate specific antigen promoter useful for prodn. of heterologous protein, or for gene therapy of prostatic cancer.": International publicationno. WO 96/14875
21. Pang, S., S. Taneja, K. Dardashti, P. Cohan, R. Kaboo, M. Sokoloff, C.-L. Tso, J. B. Dekernion and A. S. Belldegrun. (1995). "Prostate tissue specificity of the prostate-specific antigen promoter isolated from a patient with prostate cancer." Hum. Gene Ther. 6: 1417-1426.
22. Henderson, D. R. Transcriptional regulator specific for cells expressing prostate specific antigen used to express toxins, immunostimulants or anti-sense cpds., for treatment and prevention of prostatic cancer or hypertrophy. Internation publication no. WO 95/19434
23. Schuur, E. R., G. A. Henderson, L. A. Kmetec, J. D. Miller, H. G. Lamparski and D. R. Henderson. (1996). "Prostate-specific antigen expression is regulated by an upstream enhancer." J Biol Chem. 271 (12): 7043-7051.
24. Rodriguez, R., E. R. Schuur, H. Y. Lim, G. A. Henderson, J. W. Simons and D. R. Henderson (1997) Prostate attenuated replication competent adenovirus (ARCA) CN706: a selective cytotoxic for prostate-specific antigen-positive prostate cancer cells. Cancer Res. 57: 2559-2563.
25. Horoszewicz, J. S., E. Kawinski and G. P. Murphy (1987) Monoclonal antibodies to a new antigenic marker in epithelial prostatic cells and serum of prostate cancer patients. Anticancer Res. 7: 927-936.
26. Troyer, J. K., Q. Feng, M. L. Beckett and G. L. Wright Jr. (1995) Biochemical characterization and mapping of the 7E11-C5.3 epitope of the prostate specific membrane antigen. Urol. Oncol. 1: 29-37.
27. Troyer, J. K., M. L. Beckett and G. L. Wright Jr. (1997) Location of the prostate specific membrane antigen in the LNCaP prostate carcinoma cell line. The Prostate 30: 232-242.
28. Liu, H., P. Moy, S. Kim, Y. Xia, A. Rajasekaran, V. Navarro, B. Knudsen and N. H. Bander (1997) Monoclonal antibodies to the extracellular domain of prostate-specific membrane antigen also react with tumor vascular endothelium. Cancer Res. 57: 3629-3634.
29. Murphy, G. P., W. J. Tino, E. H. Holmes, A. L. Boynton, S. J. Erikson, V. A. Bowes, R. J. Barren, B. A. Tjoa, S. L. Misrock, H. Ragde and G. M. Kenny. (1996) Measurement of prostate-specific membrane antigen in the serum with a new antibody. The Prostate 28: 266-271.
30. Israeli, R. S., C. T. Powell, W. R. Fair and W. D. Heston (1993) Molecular cloning of a complementary DNA encoding a prostate-specific membrane antigen. Cancer Res. 53: 227-230.
31. Su, S. L., I. P. Huang W. R. Fair and W. D. W. Heston (1995) Alternatively spliced variants of prostate-specific membrane antigen RNA: ratio of expression as a potential measurement of progression. Cancer Res. 55: 1441-1443.
32. Pinto, J. T., B. P. Suffoletto, T. M. Berzin, C. H. QIAO, S. Lin, W. P. Tong, F. May, B. Mukherjee and W. D. W. Heston (1996) Prostate-specific membrane antigen: a novel folate hydrolase in human prostatic carcinoma cells. Clinical Cancer Res. 2: 1445-1451.
33. Carter, R. E., A. R. Feldman and J. T. Coyle (1996) Prostate-specific membrane antigen is a hydrolase with substrate and pharmacologic characteristics of a neuropeptidase. Proc. Natl. Acad. Sci. USA 93: 749-753.

34. Wright, G. L., C. Haley, M. L. Beckett and P. F. Schellhammer (1995) Expression of prostate-specific membrane antigen in normal, benign, and malignant prostate tissues. Urol. Oncol. 1: 16-28.
35. Lopes, D., W. L. Davis, M. J. Rosenstraus, Uveges, A. J. and S. C. Gilman (1990) Immunohistochemical and pharmacokinetic characterization of the site-specific immunoconjugate CYT-356 derived from the antiprostate monoclonal antibody 7E11-C5. Cancer Res. 50: 6423-6429.
36. Silver, D. A., I. Pellicer, W. R. Fair, W. D. W. Heston and C. Cordon-Cardo (1997) Prostate-specific membrane antigen expression in normal and malignant tissues. Clin. Cancer Res. 3: 81-85.
37. Israeli, R. S., C. T. Powell, J. G. Corr, W. R. Fair and W. D. W. Heston (1994) Expression of the prostate-specific membrane antigen. Cancer Res. 54: 1807-1811.
38. Wright, G. L. JR., M. Grob, C. Haley, K. Grossman, K. Newhall, D. Petrylak, J. Troyer, A. Konchuba, P. F. Schellhammer and R. Moriarty (1996) Upregulation of prostate-specific membrane antigen after androgen-deprivation therapy. Urology 48: 326-334.
39. Fair, W. R., R. S. Israeli and W. D. W. Heston (1997) Prostate-specific membrane antigen. The Prostate 32: 140-148.
40. O'Keefe, D. S., S. L. Su, D. J. Bacich, Y. Horiguchi, Y. Luo, C. T. Powell, D. Zandvliet, P. J. Russell, P. L. Molloy, N. J. Nowak, T. B. Shows, C. Mullins, R. A. Vonder Haar, W. R. Fair and W. D. W. Heston (1998) Mapping, genomic organization and promoter analysis of the human prostate-specific membrane antigen gene. Biochim et Biophys. Acta 1443: 113-127.
41. Lockett, L. J., Molloy, P. L., Russell, P. J. and Both, G. W. (1997) Relative Efficiency Of Tumour Cell Killing In Vitro By Two Enzyme-Prodrug Systems Delivered By Identical Adenovirus Vectors. Clinical Cancer Res. 3: 2075-2080.
42. Xu Z Z, Hyatt A, Boyle D B, Both G W. (1997) Construction of ovine adenovirus recombinants by gene insertion or deletion of related terminal region sequences. Virology 230: 62-71.
43. Vrati S, Macavoy E S, Xu Z Z, Smole C, Boyle D B, Both G W. (1996) Construction and transfection of ovine adenovirus genomic clones to rescue modified viruses. Virology 220: 200-203.
44. Martiniello-Wilks, R., Garcia-Aragon, J., Daja, M., Russell, P., Both, G. W" Molloy, P. L., Lockett, L. J. and Russell, P. J. (1998) Human Gene Therapy 9: 99-106.
45. Graulich W., Nettlebeck, D. M., Fischer D., Kissell T and R. Muller (1999) Cell type specificity of the human endoglin promoter. Gene 227; 55-62.
46. Underwood, P. A. and P. A. Bean (1996) The effect of vitronectin and other extracellular matrix molecules on endothelial expansion and plasminogen activation. Cells and Materials 6: 193-207.
47. Cameron, F. H., Moghaddam, M. J., Bender, V. J., Whittaker, R. G., Mott, M., and Lockett, T. J. (1999). A transfection compound series based on a versatile Tris linkage. Biochimica Et Biophysica Acta 1417(1), 37-50.
48. Khatri, A., and Both, G. W. (1998). Identification of transcripts and promoter regions of ovine adenovirus OAV287. Virology 245(1), 128-141.
49. Vrati, S., Brookes, D. E., Strike, P., Khatri, A., Boyle, D. B., and Both, G. W. (1996a). Unique genome arrangement of an ovine adenovirus: Identification of new proteins and proteinase cleavage sites. Virology 220(1), 186-199.
50. Vrati, S., Macavoy, E. S., Xu, Z. Z., Smole, C., Boyle, D. B., and Both, G. W. (1996b). Construction and transfection of ovine adenovirus genomic clones to rescue modified viruses. Virology 220(1), 200-203.
51. Xu, Z. Z., Hyatt, A., Boyle, D. B., and Both, G. W. (1997). Construction of ovine adenovirus recombinants by gene insertion or deletion of related terminal region sequences. Virology 230(1), 62-71.

The invention claimed is:

1. A recombinant vector comprising an ovine adenovirus genome and a sequence encoding a heterologous polypeptide, wherein the sequence encoding the heterologous polypeptide is inserted between E4 and E3 transcription units of the ovine adenovirus genome, and wherein at least one enhancer element obtained from intron 3 of the PSM gene is operably linked to the sequence encoding the heterologous polypeptide.

2. A recombinant vector as claimed in claim 1, wherein the sequence encoding the heterologous polypeptide is inserted between nucleotides 26,682 and the 5' end of the E4 promoter of the ovine adenovirus genome.

3. A recombinant vector as claimed in claim 1, wherein the sequence encoding the heterologous polypeptide is inserted between nucleotides 26,682 and 26,555 of the ovine adenovirus genome.

4. A recombinant vector as claimed in claim 1, wherein the sequence encoding the heterologous polypeptide is inserted between an Apa1 and Not1 site between the E4 and E3 transcription units of the ovine adenovirus genome.

5. A recombinant vector as claimed in claim 1, wherein the vector comprises a heterologous promoter.

6. A recombinant vector as claimed in claim 5, wherein the promoter is located upstream from and is operably linked to the sequence encoding the heterologous polypeptide.

7. A recombinant vector as claimed in claim 5, wherein the vector comprises at least one regulatory element obtained from intron 3 of the PSM gene operably linked to the heterologous promoter.

8. The recombinant vector of claim 1 wherein the ovine adenovirus vector has increased stability.

9. A recombinant vector according to claim 1 in which the enhancer element comprises nucleotides 1-171 of SEQ ID NO: 1.

10. A recombinant vector according to claim 1 in which the enhancer element comprises nucleotides 1-332 of SEQ ID NO: 1.

11. A method for directing expression of a coding sequence in a cell, the method comprising introducing into the cell a recombinant vector according to any one of claims 1-4, 5 and 6.

12. A method of delivering a sequence encoding a heterologous polypeptide to a target cell, the method comprising transducing the cell with a recombinant vector according to any one of claims 1-4, 5 and 6.

13. A method of delivering a sequence encoding a heterologous polypeptide to an animal cell, the method comprising administering to an animal or a cultured animal cell a recombinant vector according to any one of claims 1-4, 5 and 6.

14. A method of gene transfer to human cells, the method comprising administering to the cells a recombinant vector according to any one of claims 1-4, 5 and 6 such that the vector infects at least one cell and the infected cell expresses the heterologous polypeptide.

* * * * *

SEQUENCE LISTING

```
<160> NUMBER OF SEQ ID NOS: 2

<210> SEQ ID NO 1
<211> LENGTH: 335
<212> TYPE: DNA
<213> ORGANISM: Homo sapiens

<400> SEQUENCE: 1
aattattttt tcctttaacc tttcaaactc aaggaaaacc agttggcctt gactctgttt      60
gtggaaaatt ttaaactact ggtttaattt ctttattggt tgtaatatga ctattttacg     120
tcatataaca attttattg tttgttaaat gactttattg tttgtcatat gataatttta     180
tgtcatagaa caatttttat tgcttgatat atgactttat tgttatatgg ctatacaact    240 agatttttt gttgttttttg accgagtctt actctgtcac ccaggctgga gtgtaatggc    300
atggtctcag ctcactgcaa cctccgcctc ccggg                                335

<210> SEQ ID NO 2
<211> LENGTH: 93525
<212> TYPE: DNA
<213> ORGANISM: Homo sapiens
<220> FEATURE:
<221> NAME/KEY: misc_feature
<222> LOCATION: (81824)..(81824)
```

```
<223> OTHER INFORMATION: n is a, c, g, or t
<220> FEATURE:
<221> NAME/KEY: misc_feature
<222> LOCATION: (88177)..(88177)
<223> OTHER INFORMATION: n is a, c, g, or t
<220> FEATURE:
<221> NAME/KEY: misc_feature
<222> LOCATION: (88179)..(88179)
<223> OTHER INFORMATION: n is a, c, g, or t
<220> FEATURE:
<221> NAME/KEY: misc_feature
<222> LOCATION: (88185)..(88185)
<223> OTHER INFORMATION: n is a, c, g, or t
<220> FEATURE:
<221> NAME/KEY: misc_feature
<222> LOCATION: (88188)..(88189)
<223> OTHER INFORMATION: n is a, c, g, or t

<400> SEQUENCE: 2
aagggtgctc cttaggctga atgcttgcag acaggatgct tggttacaga tgggctgtga      60
ctcgagtgga gttttataag ggtgctcctt aggctgaatg cttgcagaca ggatgcttgg     120
ttacagatgg gctgtgagct gggtgcttgt aagaggatgc ttgggtgcta agtgagccat     180
ttgcagttga ccctattctt ggaacattca ttcccctcta cccctgtttc tgttcctgcc     240
agctaagccc atttttcatt tttcttttaa ctccttagcg ctccgcaaaa cttaatcaat     300
ttctttaaac ctcagttttc ttatctgtaa aggtaaaata ataatacagg gtgcaacaga     360
aaaatctagt gtggtttaca taatcacctg ttagagattt taaattattt caggataagt     420
catgataatt aaatgaaata atgcacataa agcacatagt gtggtgtcct ccatatagaa     480
aatgctcagt atattggtta ttaactactt gttgaaggtt tatcttctcc actaaactgt     540
aagttccaca agccttacaa tatgtgacag atattcattc attgtctgaa ttcttcaaat     600
acatcctctt caccatagcg tcttattaat tgaattatta attgaataaa ttctattgtt     660
caaaaatcac ttttatattt aactgaaatt tgcttactta taatcacatc taaccttcaa     720
agaaaacaca ttaaccaact gtactgggta atgttactgg gtgatcccac gttttacaaa     780
tgagaagata tattctggta agttgaatac ttagcaccca ggggtaatca gcttggacag     840
gaccaggtcc aaagactgtt aagagtcttc tgactccaaa ctcagtgctc cctccagtgc     900
cacaagcaaa ctccataaag gtatcctgtg ctgaatagag actgtagagt ggtacaaagt     960
aagacagaca ttatattaag tcttagcttt gtgacttcga atgacttacc taatctagct    1020
aaatttcagt tttaccatgt gtaaatcagg aagagtaata gaacaaacct tgaagggtcc    1080
caatggtgat taaatgaggt gatgtacata acatgcatca ctcataataa gtgctcttta    1140
aatattagtc actattatta gccatctctg attagatttg acaataggaa cattaggaaa    1200
gatatagtac attcaggatt ttgttagaaa gagatgaaga aattcccttc cttcctgccc    1260
taggtcatct aggagttgtc atggttcatt gttgacaaat taattttccc aaatttttca    1320
ctttgctcag aaagtctaca tcgaagcacc caagactgta caatctagtc catctttttc    1380
cacttaactc atactgtgct ctcccttcct caaagcaaac tgtttgctat tccttgaata    1440
cactctgagt tttctgcctt tgcctactca gctgggccat ggcccctaat gtttcttctc    1500
atctccactg ggtcaaatcc tacctgtacc ttatggttct gttaaaagca gtgcttccat    1560
aaagtactcc tagcaaatgc acggcctctc tcacggatta taagaacaca gtttatttta    1620
taaagcatgt agctattctc tccctcgaaa tacgattatt attattaaga atttatagca    1680
gggatataat tttgtatgat gattcttctg gttaatccaa ccaagattga ttttatatct    1740
attacgtaag acagtagcca gacatagccg ggatatgaaa ataaagtctc tgccttcaac    1800
```

```
aagttccagt attctttttct ttcctcccct cccctccccct cccttccccct cccccttcctt    1860
cccttttccct tcccttcctt tctttcttga gggagtctca ctctgtcacc aggctccagt    1920
gcagtggcgc tatcttggct gactgcaacc tccgcctccc cggttcaagc gattctcctg    1980
cctcagcctc ctgagtagct gggactacag gagcccgcca ccacgcccag ctaattttttg    2040
tattttttagt agagatgggg tttcaccatg ttggccagga tggtctcgat ttctcgactt    2100
cgtgatccgc ctgtctgggc ctcccaaagt gctgggatta caggcgtgag ccaccacgcc    2160
cggctttaaa aaatggtttt gtaatgtaag tggaggataa taccctacat gtttattaat    2220
aacaataata ttctttagga aaaagggcgc ggtggtgatt tacactgatg acaagcattc    2280
ccgactatgg aaaaaaagcg cagcttttttc tgctctgctt ttattcagta gagtattgta    2340
gagattgtat agaatttcag agttgaataa aagttcctca taattatagg agtggagaga    2400
ggagagtctc tttcttcctt tcatttttat atttaagcaa gagctggaca ttttccaaga    2460
aagtttttttt tttttaaggc gcctctcaaa aggggccgga tttccttctc ctggaggcag    2520
atgttgcctc tctctctcgc tcggattggt tcagtgcact ctagaaacac tgctgtggtg    2580
gagaaactgg accccaggtc tggagcgaat tccagcctgc agggctgata agcgaggcat    2640
tagtgagatt gagagagact ttaccccgcc gtggtggttg gagggcgcgc agtagagcag    2700
cagcacaggc gcgggtcccg ggaggccggc tctgctcgcg ccgagatgtg gaatctcctt    2760
cacgaaaccg actcggctgt ggccaccgcg cgccgcccgc gctggctgtg cgctggggcg    2820
ctggtgctgg cgggtggctt ctttctcctc ggcttcctct tcggtagggg ggcgcctcgc    2880
ggagcaaacc tcggagtctt tccccgtggt gccgcggtgc tggactcgcg ggtcagctgc    2940
cgagtgggat cctgttgctg gtcttcccca ggggcggcga ttagggtcgg ggtaatgtgg    3000
ggtgagcacc cctcgagtta ggaggagggt agctgggaac ggtgcagggc tgagttctcg    3060
acaagctgct ggtaggacag tcactcaggt tgagggtaga actgagagaa cctgaaactg    3120
ggcgtaggaa ggttccaagt gctggagccc tgcaagacag aggaagtttt ttttttgctt    3180
ttgttttgtt ttgttttgtt ttgtttgttt ttgttttgtt gtttgttttt ttacctctct    3240
gtgcattctt tcttccttgg aagtaacaga ggcaagcttg ggaactgtgt gaaccaggtc    3300
agcaatctgg acaggtcttt accagcgggt cttttgctgt ttttcctggg tactgatttg    3360
cagacttgat ccaactttct aagaaaagca gaaccacaca ggcaagctca gactcttttta    3420
ttaaattcca gttttgactt tgccacttct tagtggcctt gaacaagtta ccgagtccct    3480
ctcagcgtta gttaccctat tttatgatga ggataatatt atctgcaaat tattggtaat    3540
agtaaataat atagcatgta aatctcctag cacagtactg ggattttcgc cactttattt    3600
cttctttttac caagatactc ctcattggac tttaatacac aggactagtc taaggtatca    3660
ccaggtagtc cactcctgct cggaattctt gaccctcttt cgggatttag aagaataggg    3720
catggaccag atgggtttaa acaaattcaa tatcttccac tagcttcacc ttggggttgt    3780
taaaagattt ttgaaccaca cactgtgctc ataacaatct tcatctctta aaaggatttt    3840
attcttcctg gtattgccct cactctcatc cctgtattcc gtgctcagtg gctgacacag    3900
aagagttctt tattgatgtc cgccccccac ccactaggat tctctgctct ccccttcccc    3960
ctacaggcct ccatcctctt catcctgttc attttttcaga tctcagttca agcatctcgt    4020
cctcagtgtg gtgtttcctg atccctcact ctaatccaag tctttctgtt ttatgcacag    4080
gtggaatctt atttccgttt gcgtccaatc atgtatttta atatgcatgt atatatgtat    4140
```

```
gtgcatttgt atgcatgcga ttaagaacta gaataattaa taattggaaa gctccatgaa   4200
agctggttgg ggactaattt tgtaactact ttattcccag atcctgtaat ttctctaaat   4260
aaaccctgga atcttgcctt atctccttca ggttaaaagc caactgcaag gtctaatgac   4320
tgcaggatct agctatccat tgtttctggc cgcctatgcg tgcactgggt gtctggcaga   4380
gaggctgggt aaattgtagt ttcattgtag ctgtctgaac ttggatttct cacgcctact   4440
tcactggaaa cgcaaactct cacagcattt tgttttagtt tcagaatcag agcaaattag   4500
aagtctgaat ttccttcaac acttggaaat aatttattta tttgaaatat attcataatt   4560
aattcgttat aaaaatgtat taaatgctta tttgagtcag cagaggaaga tagaaacttt   4620
atgaaagtag aaggtggatc tccttttgc cttcattttc agaacatctc gtttacaccc   4680
attagttgaa acattaatgt cattttattt tcgtcctgat tatctcataa aacatttctt   4740
agaataacag caatacctat cattgaagtt ggataagaaa tattttgcaa ttggtttgca   4800
acttaaaaat ctgtttgcat gactcttttt cagtgaaagt aggcaagaga aattaaaatt   4860
cagaaatatc tcacctaatg tcagaggtaa tattgataat ttgtgtttta caaataatac   4920
atacaacaat aatgaaaaat aagtcctatc tataggctcg tatctcatgc ctattttttgg   4980 atgtattttt cagggtggtt tataaaatcc tccaatgaag ctactaacat tactccaaag   5040
cataatatga aagcattttt ggatgaattg aaagctgaga acatcaagaa gttcttacag   5100
taagtacatc ctcgaaagtt tatatggaca agttgttaga aaaatttatc attctgtttt   5160
ggtccaatat tttatatata ggaactggac tttttttctta aaattttatt tattaaagat   5220
cttggatcat atttcatctg aggaggacta tactttcagc taaattttgt cattacagag   5280
gtttagagca ggagtcagca aacttttttct gtacaaggac cagcctttgt aggccagctg   5340
atctgtgtca catctagtca gctctgctat tgcagcacaa aagaagtcat agaaaataca   5400
taaacagtca gttctgataa aactttcctt atgggcactg aaatttggat ttcatataat   5460
tgatgtgtca aaaatattat ttttaaaacc aatttaaaat ataaaaacca ttcttagctt   5520
gtggactgta cagaaacagt tagtggtcca gatttggcca gtggaaccta gtttgctgat   5580
taatgcttta gagaaagata ttgcattttta gttaaaaaaa tggactttga gttagaattg   5640
agtttgaatt ccatctttgc ctattaatac tttggatgaa tacttaacct ttctgagctc   5700
tcttttccac atctgtaaaa tgggaataat gatcttatta tgatatggat gaagtcaaag   5760
agcatatatt tagcataaat ttggcatatt ttaaaaacta gctccctact tcctgaaata   5820
gctatttcca gtgtaggacg aaagagataa ataagtaaat ttaaaaagca accaaaaaga   5880
aaatacttat atagaattac tatatataat tgattagaat acttgttttt ttttcttttc   5940
ttttctttcc tttttttctt tgagatggag tttcgctctt gttgcccagg ctggagtgca   6000
atggcgtgat ctcagctcac tgtaacctcc gcctcccagg tacaagcgat tctcatgcct   6060
cctgagtacc tgggattaca ggcatgcacc accacaccca gctaatttg tattttaat   6120 agagacaggg tttctccatg ttggtcaagc tggtctcaaa ctcctgacct caggtgatct   6180
gcccgcctcg gcttcccaaa gtactgggat taccggtgtg agcccccaca cccagcccag   6240
aatacttgct ttttttttaa gcatgagatc cttttgtgaa tttttacaaa ttgagttagc   6300
tcatgtgtcc taaaatactt gaagtccctc taatgattgc aggattcgct ggtgaataaa   6360
ggttgtaatt ctaaattaaa agaccattac acacacacac atgcacatag gtatgcatag   6420
atgtgcacac atataatcat acaaacatat atatgtttgt attaattaca acagaattaa   6480
aagtataaat acaaattgat aggataccctc tcaggtcttt ggaagggccg tttcaaatgt   6540
```

```
gagactctga agctcaaact tctttatctt tgtggaaaac cctcctctgc ctgttgtgct    6600
tattccactc taataatgta tagtaggtat aataaaagtg gaggtctggc aaggtatggt    6660
ctttactcct tgacagagct gctgttccag ctttcttcct ttcccaatat tagtggtgga    6720
agagatccaa gttactccaa gttatcagca gcctatccat aaggtcagca gcaacttcag    6780
tccttgcctc ttcagaagaa agaattcaac tgggggcaaa agcagaaaaa gagaccaagg    6840
caagtttcag agcaggaatg gaagtttatt ttaaaaggcc ttataacagg aaagaaagga    6900
aggtgtgctt ggaagagagc caagcaggca catgaaggtg agagaaggcc aagtgcccca    6960
cttaactgtg atcgtaggac ttctttacgc ttgcctcttt cccatgattc ttctcttagg    7020
gtgggctgcc cagccctcct aacccttggg aaaagagcac ccgcaatgtg tttagggaag    7080
tatacacagg cccatctgag tctctcttcc tttttctggt ggagtgtacc tggaagatta    7140
tactatacca ttttttgtctc taacacgcat gcccaggaag ttgcttctcc ctggagtctg    7200
cattcagtta acattttggt gttaacaggt gtggaccatc aagagctggc ctctccctgg    7260
cactgctaaa tcattttag agaggcaatg cgatcaatgc tgaactgaac catcacctga    7320
cattctagag ggtgggggga gagcccccctc ctgacttgct cctgtctaac tacttgtaac    7380
actaacttgt gacatagatt gaccaacaaa gaagaaaaat aaatgccttt atttctcttt    7440
ttggaccctc agcaagatta agcagtcagc ttcttgttta ttctccatgt ctctaaccaa    7500
gctcctctaa ccagaacaca gggggatatt cagcataaac acacaaaaga agaaattga    7560 aagaattccc tctcattcct ccaaggacca cagaatctcc agaagcctcc taaactctcc    7620
agattttcaa tttgccattt gtccatcaga gagctttcaa ttaaaatata cccatgggtc    7680
agagactatt aaaacctctg accttccatc tggtccccct ttaaaatctt ttgttctgct    7740
cttaaaagcc cccactgcct ctgaaatatc tgcctcagta gtgaatggga agattaatta    7800
ggagcagctt ttttttcactc tgccttgatg tacagggttg tctgtgtttt cccttctttg    7860
aaaacaccca gttgaattca cagatctgtt taccattttg catctctcta gagggattct    7920
tccttttcca cattgttttg caagataaga ttgttttaaa aggtgtttta gacttttggt    7980
ctcagaattt tactggtctg tatttgaata cataggtctg tatttgaata tataggccca    8040
atgaaatcac atattaaact acacttctta atctattaat cacttgagat gtgtgtcaca    8100
agtaatttgt tgatactaga atatcaaatt ttgttaaaaa gaaaaggtaa gaataagaat    8160
ttacacattt tccagaatag caaaaatcca ttcatagatc tctctcagac tggtttaaat    8220
atattccaag tatcgtcaca ttatctcaat tattattatc attattattt tcagacaagg    8280
tttcactctg ttgccaggct ggagtgcagt ggcacaatca tagctcactg cagcttggag    8340
ctccagcctc cccagtaggt agtactacag gcacatgcca ccgtgcccag ctaattccac    8400
cttttactaa ataccttcgt catcttgaag tcttggaaac actgccaaat tatttgtaaa    8460
caagatgaaa tgtactaaaa cagaaataac agtagctctt ttaaaggact gagataatgt    8520
attcgggcat agtggctcac ccatgtaatc ccagctcttt gggaggacaa ggcaggcaga    8580
tgccttgagt gagactctgt ctctacaaaa tatttttta acttatctgg gaatggtggc    8640
atgtgtctgt agtcctatct actcaggaag ctggagttcc aggttttagt gagctatgat    8700
tgcaccactg tattccagcc tggcaacaga atgagactct gtctcttaca aaaaaaaag    8760 agataatgtg acaatactag aaacacattt aaagcagccc tacagtgata tataaacaga    8820
atttggctat ttgggaaaat ttgtaaattc atattttat tcttattctt gtttattttt    8880
```

```
tacaaaattt gatattctgg taggttcaac aacttgtgac acacatctca aatgattaaa    8940
atcattgaga agtgctattt aatacgcaat ctaattgagc ctcaagtctt tgtgaagtag    9000
tgagacagtg atgttctccc catatacaga tgagaaactc aagacacagc tagggttaca    9060
tactgagtta atgacaacac ctgtattata ccacgtacat gatttatgct aattaattta    9120
tttagtgttt gcaatggatc ttttttttctc ctactaatct tttccaggat gtgttttgtt    9180
caaatgagtg agtcccaacc ctgataatag caaaatgttg tttcctagtt ggtagtgaca    9240
agactgttac aagaaaattc acttaatagt agcaaagcct tataatgatt ttctcccact    9300
tttttgtgag taggttcaag attccccata gtaattcctt tgcttatag ggacagaggc    9360
atagctggca cttcaggata tctgcatcct acattagtta cattgcagtt tgtgatcttt    9420
gtaatattca agaaaatagc gatatgttgg ctgtttttct gttttccctg caggtgctca    9480
ctgataaggg atagagactc cttagctgcc tcttatgttt gtgtcctttt tgttacaata    9540
ttttccatat tagaaattct gtgtaagata ttttgcccct aaacatttac caaacgagga    9600
ttttaatact attttttataa atacaattta aataactta atataattat taaagtaaac    9660
aagttacagg aaattccaat tttaaaaaat tgagttactt taattcattg ttgattcatc    9720
aaataaaaaa attaaaatac atggtagaat gaaacttgaa actggaatta tcatagtcat    9780
gttggttatt agtttttta aatcaccata aggatggaat tatgttgatt ttataaagct    9840
acatatttaa aactagaaat ttatgaagtt ccaaaagttt atgaactata tatatatata    9900
tatatatata tatcttttca tgctacataa tatcttgtca tgtatttaag ggcttaagtt    9960
aaaaatactt ccaatgagct cttcagggaa acaagaaatt tcccaggagg gagaaattta   10020
aaacaatcaa aagcaccaga atctaaatat attaaatgag aaattagtct actcctgaaa   10080
atatttctgg tagccaaatt ttggccacat aatttcttg ttaaagatat tcctcttcag   10140
actaattatt gtcattgatt ttaagtgtgt cactctgtat gatagatgga gtgcaagaga   10200
ttcattctga acttgtatcg gtatgttcag attattcttt gatgaagata ctttataaat   10260
ggttgctaat caaaaagttt atcacttgtc tataactctc agtatttaaa taaatgtaat   10320
tattagtaat tcttgccatg ttacaccttg atcttttgga taaaatattt ttgtctgttt   10380
catatttttac acagtgatat aaacagataa ttccatgtaa gttccaagaa gtataggtct   10440
taagaaagaa tatgataatc taccatacga ggttatagta ataggattac acataatgat   10500
acaaaaatca gtttctccga tttttctctt gatttagtac aaattagagc ataaaaattt   10560
caaagcagac tttgaaaatc tatttcatgc aataatacta ccactttaat ttttaacgt   10620
atcacacttc aaagtacttt tgtgtaactc tgctttactt tgttgatttg gaataaaagt   10680
tgattaaaca ttaatatcta accactttca attttttgttc accagtaatt ttacacagat   10740
accacatttta gcaggaacag aacaaaactt tcagcttgca aagcaaattc aatcccagtg   10800
gaaagaattt ggcctggatt ctgttgagct agctcattat gatgtcctgt tgtcctaccc   10860
aaataagact catcccaact acatctcaat aattaatgaa gatggaaatg aggtaaaaaa   10920
taaataaata aataaaagaa acattccccc catttattct ttttcaaata ccttctatga   10980
aataatgttc tatcccatct ctaaatatta atagaaatca atattattgg atcttgtgaa   11040
tacctttaat atctcattat ccgtgtcaac tactttccta tgatgtttga gtttactgtg   11100
ttttagaaag attcgagaaa ttaatgcttg ataacagctg ctgttttta gtttttagta   11160
ctacacacca atatcaaata tgatatactt gtaaacctcc aagcataaaa agagatactt   11220
tataaaagag gttctttttt tcttttttttt ttttccagat ggagtttcac tcctgtcagg   11280
```

```
caggctggag tgcagtggtg ccatctcggc tcactgcaac ctccacctcc catgttcaag    11340
ggattctcct tcctcagtct cctgagtagc tgggattaca ggtgtgcacc accacaccca    11400
gctaattttt gtattttaa tagagacagg gtttcatcat gttggccagg ctagtctcga    11460
actcctgacc tcaggtgatc cacccgcctc agcctcccaa agttgtagaa ttacacgtgt    11520
gaggcactgc gcctggccag gagatacatt tttgataggt ttaatttata aagcactgc    11580 acagatttgg agttgctggg aaatgcacgg atccagtatg caatttgacc cagcaagttt    11640
ttattggtac ttaatgatta tgtctcaatt gatcaggttg aactctgtgc gaagaatttg    11700
tgtgtggaca tttggagagg acaagtttgg aggcaaggta ttttagcatg gtatttaaag    11760
aatttgcaat cttgtttgca agttggggca tatacttgag aaagagaaga caatgcagat    11820
aaattgatat atttattatg atgtatgttc aatatgaaag atcacaaaat ataacataca    11880
ttcatcctta cttaacatac ctcagttta gagctaccgt atgtagaaga gtccatttct    11940
atttaggtaa gttcctttag tccttttatt actgggcact cttaattaca tgtagcttga    12000
aatatgtcca gtttgatcag tgaactgaaa atgtcatgtg atttaagtac atatataatt    12060 tttttcata gtaggtcaat aacctccttt tattgactaa tgaatcagtt tcttcttaat    12120
gattaatacg ttgttatgtt ttacagtcag tgatataatt ccatactaaa ttttctaatg    12180
tgattggagc ttttcatatt aactactgtt ctcaatcata gtagttaaca ataatactt    12240 aaaaaatatt attaagccag gcgtggtggc atgttcccct aatctcagct acttgggagg    12300
ctgagatagg atgattgctg gagccaggag ttgcagacca gcttgaacaa catagcaaga    12360
ctccatctta aaggaaaaa aaaaaaaag aaaaacaaac taaaaaaacc ctaaaatata    12420
ttatattgaa aaggcaatac cactacacgt catatagtct cagaatgttt gttaaataag    12480
tggtggcata tctatacagt taaataccga ggggtcttta aaacatgttc agaaaatta    12540 tttaaagaaa taaatattg acaatgttaa aatgtataca tatgcttaaa cgtctctttg    12600
atctatcaaa tttgagaatt gtctaggtac aatgtggaaa agagcagaca tataatatat    12660
tttagttttt gttttttttt tttttgaga cggagtctcg ctttgtcgcc caggctggag    12720
tgcagtggcg gtatctccgc tcactgcaag ctccgcctcc cgggttcaca ccattctcct    12780
gtctcagcct cccagtagc tgggactaca ggctcccgcc acgacgcccg gctaattttt    12840
tttgtatttt ttggtggaga cggggtttca cagttttagc caggatggtc tcgatctgct    12900
gacctcgtta tccacccgcc tcggcctccc aaagtgctgg ttagtttttt tttaagatgg    12960
ggtcttgcta tgttgtcgtt ttttcttct cttttccttc ctcctcactt cccagttttg    13020
actataccat tgcttatttt atttcattat ttacttttgt attacaaaca tgcataatgt    13080
taccaaagcc tgttacataa tacaaaatga atcatgtaaa agttcactt gggagatttt    13140 cctgaatagt gttagatacc tagtttctta atttttaaa tttatatcat tagttctttt    13200
ttatttttat ccaagttata tatgtacata accacataat tttcctgagt gcttgctttt    13260
tctctatttt cctcttttcca gaggcaatca ttattcaact ataagttaat tctttttata    13320
tttacatcta tttctataaa ttacatgctt atatggcttt tatttcagat gcaggcatta    13380
tctattgaca ttgtgacaag tcagctccct gttcatccct tggccccaac caccatgttc    13440
tcttactacc tcccatctcc cagtacaatt taattgttat gaataacagt tcacagctga    13500
gctatgtggt aaactatgat ttcttttata cccctgcaca aaacagacaa gttctccatc    13560
cgtaggcaac aaatatgatt agtattttgt ggatcctatg agaaatattt ttaatgtata    13620
```

```
cagagacatt gtttcacctt tgattatgca gaaataacat cccataaaga tttaactata   13680
tattgacttt tttatgtcac aaaatgtaaa cagaaattat aaactaatat tgttttagtt   13740
atactcagaa tatataattt gaggctacca gtgcattttg gaaagtaaaa aatactctaa   13800
gactgaaatt taatctaact ttgataaagt caaccaaaaa ggcatttcct tgacattaaa   13860
aacttttctt acttgttaga atagctcata aacttgctgt aaaattcagt gtggcatagt   13920
ggtgctgcaa aattgattac cataaaggca aatcaagtga gacaagtttg aatattccct   13980
tgcctgaaag acatgcttat ataatgactt tgttccttta ttgatttta ttgcacctca   14040 gcataatttt tcttttaatc ttacctagtg attcagatga gttcatttct catgtgaatc   14100
acagaaaaaa atatgggaaa tttggaatat gtggggatgt ggcaagtcgt agttgatttg   14160
gtttcatttt agcttctatc catgtcagaa aagggaaata actactgctc tagtcagtac   14220
aatgtaaaat ctgcccagat cccctcctca tctccaaatc cctcccattt gtattactgc   14280
actgaccaag acctatacaa tataatgttg aaaagaagtt ttgatagcag atatccttaa   14340
ctttcttctg gtcttgaagg aaataccttt aattctttct caccattaat tatggtattt   14400
actgttttct ttttctggtt atcttaaagt acatcctttc cacatatact aaaatttttt   14460
gctgtatgga tttatattaa acacattttt ctttaagatg agcatgcgat ttttctttct   14520
tgatctgaag atgacattca gtgatattct aatgttagaa taatcttata ttttttgaac   14580
ttgtaatatt agcattaggg ttttaaattc atatattgat atatattatg tttatactca   14640
tagcatgttt agtctgtgtt tttgcaatct attttgttggg ttataatttc aatattctac   14700
ttgccttcta aaatgagttg ggttttttaat attttctgaa gtaggtttta ttgcaattaa   14760 attattttt cctttaaccct tcaaactca aggaaaacca gttggccttg actctgtttg   14820
tggaaaattt taaactactg gtttaatttc tttattggtt gtaatatgac tattttacgt   14880
catataacaa ttttttattgt ttgttaaatg actttattgt ttgtcatatg ataattttat   14940
gtcatagaac aattttttatt gcttgatata tgactttatt gttatatggc tatacaacta   15000 gattttttg ttgttttga ccgagtctta ctctgtcacc caggctggag tgtaatggca   15060
tggtctcagc tcactgcaac ctccgcctcc cgggttcaag ccattcttcc acctcagcct   15120
cccaagtagc tgggactaca ggcatgagcc accgcacccg gctaattttt gtattttag    15180 tagagacgtg gttccactat gttggccagg ctgatctcga actcctgacc ttgtaatcca   15240
cccgcctcgg cctgccaaag tgctgggatt acaggcgtga gccattgtgc ctggccgatt   15300
ttttaaaaaa tgtattctta tgtcagtttt cataagtttt atttaaaatg cattttccat   15360
ttgatgtaag ctttcaaatt tatagtatag ttgttcctag tattttctta tctttttgtaa  15420 tctgttcagc gtctgtagat gtgcctcttt ttaataaata atattattg tttgcgcttt    15480 tgctattttt tttcttattg ctcttgagag ggatatgtca aatttactag tgtatccaaa   15540
gaataaactt tggcgttggc aatcttttct catctatctt tgcttatat tttattaatt    15600 ctgttcttgt tttataattg cctctttat cttctttgtg tttactttgc tgttctttgt    15660
aaaatcctca gtagaatgct taacttattg acattcagtc tttcttcatt tctactatga   15720
gtatttagag ccataaattt cccctttaac ttcccttcc acttcaacta catctcacaa    15780
atttggatta ggagtagttt aattatcatt agtatctaaa tattttttaa tttctgtatt   15840
ttcttctttg atcctgcaac tatttacaag tatttttaa aatcctgaat ataaagattg    15900
ttattgttat ttgtttgatc tgatctctaa attgaatata ttgagatcag ataatgtggt   15960
ttgtaggaca ctaatccttt gacaattgtt gaggcttcct ttggaaccta atatgtgctc   16020
```

```
aattttttata gacgttctgt gtttctttgg gaaaaacatg tatttgatgg ttgtttggtt   16080
taatattttg tatttgtaca ttagtttgag tttgcttatt atttggctga aatctccatt   16140
atccttaatg tgctctctca ttttgtctgc ttcctttatt aattagagat aaatgttaaa   16200
ttatctcacc tcactatagt gatgtctgtt ttatactata tatataaaat ttataattcc   16260
ataaatttat gttatgtata atttggagac ctattatcat atataaacag aattgttgat   16320
gaaatgacag acttatactt atgtagtagc cttttttatc tcgtcataat gttatttgac   16380
tttgtcctaa aattttttt aattaatatt tgtttggtat ttcttttca gcgggttat    16440 gtcactgctt gtcaattggt acacagctga ttttatttag acatgctacg cttttaatt    16500 attcttttt ccattttcat ttttataat tctgatatac aatatttagg tcacttttac     16560
cttcctctag tgtgaatttt actcttcctt ttttccccta aagctttggt gtcataattc   16620
aatcaatatt tctacaatat agaaaccttta gaacactttc acttttgtta tatattacca  16680
atttatatgc ataattttaa ttcagtcttg tttcataaac ttgataaata tgtttattaa   16740
tatgatagta ataagaattt gggaattctt taaggctaat ttgaaggctg attcctcctg   16800
atcatttctc ttaggcccca gggagcacta caaacctggc actgctttaa aataaatatt   16860
ttcgcttgag gcatactata taaacagtga atggaaattt gtagggttat gaattatctg   16920 gaacccttt ttcctgctt acgctaagcc attactttcc atggagcaag tttattttga    16980
atttatcctt aaccctgaag gatattgttg ttctttttt ttttttttt tttttttgtca    17040 cccaggctgg agtgcagtgg catgatctcc actcactgca agcttgcatg ctgggttcaa   17100
gtgattctcc tgtctcagcc tcctgagtag ctgggattac aagcacgtag gcccggctaa   17160
ttttcctatt tttagtagag acgcggtttc accatgttgg tcaggctggt ctcaaactcc   17220
tgacctcgtg atccacccac cttgggctcc caaagtgctg ggattacagg cgtgagccac   17280
ctcacctggt caggatattg ttgttcttag accagcttta tgcacagtct tctgctagat   17340
tccattatgt gaaccagctt taaactaact cctgaatcct tttcatgggg ccataggctt   17400
tgatagatcc atctaaggca aagccaaatt tcgtgctacc tctgaggatt cttgctttca   17460 tttatttt ttgcttctga atattcctta ctattttttt tccaatttaa ttttaaactt     17520
aaaaaaacat atatttggtt cagtgttttt cattcttttc agtgcatatg ttgttcagag   17580
aatctagata aggccagttg tggattcccc aatcatgtac ttttttttaa agtaaattta   17640
atatttaatt tgttcctagg taattatcta agcactatta taatgattga gattaccaaa   17700
caaaggtact ttttatttgg tgattaaaat cttctccaa aatcgaaagc tagtccttac    17760
aagttctctc aagaaaattca tgaggttaat ttacttctaa ccttctgtga agcaactaca  17820
tatttaggct tgtgttcaca ctagcttagt atgtatgcca cttacaaaaa ataaatttct   17880
aattcttcct tctatcagta cacagtttac agtatatagt attccttttg gaagagtatc   17940
tttttacctc ctctgagctt ttcttctat agtacttact tattttatga ttgttgtttt    18000
tcatttggtt gatttttagt tattggtggg gttttttag ctttgttcc ttgaatagat     18060 ctaaccattt tgaggacaga atctgtgatt tattcatctc gtgaattctt cacaacttct   18120
agcatagtgc tgggtatctg atactatcat caaaatcctg aaggattcat tcaccctcta   18180
ctgacataaa agataatatt catttttttt gtgtttgatt atagtaatca aacttttaact  18240 gttttatttt gattataata ttttgttct ctagattttc aacacatcat tatttgaacc    18300
acctcctcca ggatatgaaa atgtttcgga tattgtacca cctttcagtg ctttctctcc   18360
```

```
tcaaggaatg ccagaggtaa aaacacagtg caacaaataa aaatgacaaa aagaagcctt     18420
ccttctcttc atatgttcag ccgataatta aagggtcata aagggacttt taatgtaatc     18480
caattcattt ttccacattt aagtaatgag aatgtcttag taagaagaag gaatattgat     18540
tatattttat taatggtatt tttaaagata caacttactg caatgagatg cacaaatccc     18600
aaatgcacat ttattgattt ttgacaaatg ccaacatctg ggtgatccaa atcccatcaa     18660
tgtacagcat attaccttca cttcagaaag ttcccttatg gttcttctta atcaactcta     18720 catacccag aggatatctt tctttgacat ttctgccacc ataaattagt tttgcctatt      18780 ctaattttc atcttttgt tcactctgtg ttttcctttg ttgaaaagag atccttaatt       18840
ttgacgttgt caaattattt tccttatgtt tttgcacttt gggccttctt tattaatatt    18900
ctccttcttt atgatttaca gtgatataac ttcatgactt atgtatacca aaaattaaca    18960
atacattttt atttaaaaat agtattaata ttatcagatt gaagctaaat ataaaagacc    19020
agatagtata tgatagcaga aagtataatg aataaattta atttaaaata gctaaaaaaa    19080
tataaaatat actttaaaaa tcttaaatga atgtgatcta ttgaagaagt tgaagtgtga    19140
agtgtgaaat tgaagaacac tgaaatgtat tgagcagtga aaagactgtg tataaaaaaa    19200
caggttggcc gggtgcggag gcaggcagat caactgaggt caggagttcg agatcagcct    19260
ggccaacatg gggaaacccc atctctatta aaaatacaaa ataattagcc agatgcggtg    19320
acacacaact gtagtcccag ctactcagga ggctgaggca ggaggatggc gtgaacccgg    19380
gaggcggagc ttgcagtgag ctgagattgt gccactgcac tccagcctag acagagcga    19440 gactccatct tagaaaaaca aaacaaaaca aagaaaaaa cagttaaacc gtttatgttt    19500
ctggctgaga agacatcata ttataaggag aaaattacac ctagattagt ttgtaggttt    19560
actgcatacc caattaaaat cttccaaata attttggac tttgacatta ctattaatcg     19620
taagaaagag ttataaagac cgttgtctct tatttccttc aaatagactt aaaatcttcc    19680
agatcaatgg ctaaatacaa agagcacaca tgttgtatgg gtttgctgtt tatgttcaaa    19740
tatcagatga gtttgctgat cggtgttcct cactggatca tctgtaaccc agccagtgga    19800
atgtcaattc tttcaaaact atgtatgtcc atatgtgtgt ttaaaacgtt ttacaggcca    19860
ggcgcagtgg ctaacgcctg taatcccagc actctaggag gccgaggggg gcggatcaag    19920
aggtcaggag atccagacca tcctagctaa cacggtgaaa ccctgtctct actaaacatg    19980 caaaaaatt agccgggagt ggtggcgggc gcctgtagtc ccagctactc cggaggctga    20040
ggcaggagaa tggcgtgaac gcgggaggtg gagcttgcag tgagccgaga tcgcgcctcc    20100
tgacctcagg tgatctgcct gcctccgcac ccggccaacc tgttttgta tacataatct    20160 tttcactgct caatacattt cagggttctt caatttcaca cttcacactt cagcttcttc    20220
aatagatcac attcatttaa gattttaaa gtatatttta tatttttag ctattttaaa     20280 ttaaatgtat gcacttcagc ctgggcgaca gagctagatt ccgtctcaaa aacaaaaca    20340 aaacaaaaat tcacgatcag taatctttga atttacgtct gaatcctgtg aatatgaaa    20400 tatgggactc tgctttatgc tatttaaaat tagcaatttg cgatgttcat aaaatatagt    20460
ctatctagtg gttctcaagc tttagtgtct gtcacaataa tctggatggc ttgtaaaaca    20520
cagattctag tttccactcc ctaagttaa tggggtggag cctgagagtt tgtgttttgta    20580 acaagcgtga tattgtttct gagggtccaa ggaccatctt tgagaatcac tggttttgcc    20640
tcccaattct gtctctataa ataagagtta gggagatgga agcttaagga aacaaagaaa    20700
attccgggct aagagtgcaa gattctattt attcacagtc atagaacaat ggatggtaca    20760
```

```
gtgtaagttg tacaagaagg tctttgtcta aaaacaaagc tcttttctaa cagtgacaac   20820
ttgcatttga gaagtgctga gagggaatat ctgtcacact tgttttcatt ttcaaagttt   20880
actctcattt ttaagctaat atgtttttca gtttcctctc cctcacagtt tgttttgtga   20940
ggattgctga tatatcaaaa gacagccaca tttagagaca tttaaaggta caatctcctc   21000
aaagttactt atattaaggg taagaaagt aggatattta cactaaaaaa attattttgc    21060
tgaaatcaca ttggttaatg actttgtagc cacagttaaa atagaatgag tgtgctccag   21120
agagggttaa caatgataaa tcagacatat agtgttatga ttaatagtgc attaatatta   21180
cattggtctt aggaagaaat acaagagcta aatgtaatcc ttttacagag gcaaagattc   21240
aaatgtcagt ttcccaatta gactttcctc atttttattta atattacacc cacttaagct   21300
ctagttcacc atttgtatac tctatttaaa tgcttttaa tttttttctat actacttatc    21360 acctttaat ataatgtatg ctttgcttag ttattaactt taatgctcat tattgtatta     21420
tcccatccac attacaggaa acccccaact taagatggct acttaaaatt ttttgacttc   21480
atgatggtgc aatagccata ctcattcaat acacttctca acttaccatg aggttatgtc   21540
tggataaacc cattataaat tgaaaatatc ctaagtcaaa aacacacttt aggtgtataa    21600
ttattttcaa cttaggtgag tttagtaaga cttaattcca ttgtgagtga aggaggacct   21660
gcagtgtaag ttccttcaag ggcagagatt tgttgtatta cataggcac tgcctaacac    21720 ataatagatc ttcaccaatt tgtcaaatta atcctagaat cagcttggaa acaattctat   21780
tttaatatct tatgtatatt tgtcgtgtac atgctatgaa aaatgtagtc aaaaaggaaa    21840
acaataacca aaataaaatg ataggatatt ggaaatcatc tgggacaggg gtttcaaact   21900
aggctgtgta aagactttcg aaaggcaagc atgacatggt tttaaagaga tcagtttgca   21960
gatcatcaat taccctgtgc gcttttttcat ggtattgaaa gctagcctgt cgtgaggtcc    22020
tgctccctat ttacaagcat tttcatctta ttttataaat gaaaaacatc tcctacccat    22080
tctaagtcaa tatgaagcat atatctgtgt tgtaaaaatc tctgggctt caaaaaaga     22140 gacaattaga aatattgttt tcaatgttaa gatagtgaat ggttctaata gctacgtaac   22200
aaattcttag caattcaaat ggtttacaat tgagcaaaat taaaggtaaa cccaattgag   22260
tttccagcta atatcattaa aagacacttg aatgatggat caatttgtga ttttcagatt   22320
ataacttgaa agaagtttaa ataagttagt aacaattcca taacaaatct ttcattccta   22380 tccaagttttt ctcagaactt actgtaaaaa caagaaatgt aaattgaact gttgttgctg    22440
atcccagtct cattctagca ataatttgtt cacccactga acaaatgtgt taagataacg   22500
cttcactgtc ccactcattg cattaaaaga tatatttcta atcaaatttt atggttatgc    22560
attatatata agaattgcaa tgatgttgtt agacttaatt tgatactgct agtaattata   22620
attataactt aatctatctt tttttttttt tttttttgaga ccaagtctta ctctgtcgcc   22680
cgggctggag tgcagtggta tgatcttggc tcactgcaac ctccacctcc cgtgttcaag   22740
caattctcat acctcagccc ccgagtagct gggattacag gcggtgccac cacgcccagc   22800 tgattttgt gttttagta gacatgggtt ttcactatgt tggccaggct ggtcttgaac     22860
tcccaacctc aagtgatcca cccaacccag cctcccaaag tgctgggatt acaggcatga   22920
gccaccatgc ctggcctata attataactt actcttgaag ctgttctta acacaatctg   22980 tcacaaaaat aaattttaa aaaaattga cttataaaga tatactgatt caaggaaatt    23040
tgacagtgat taataaaaga ctttcaagca tacccatatt taaggtaata gattctgaat   23100
```

```
tgaaatttag aatgctagtt gataattgtg gagtgttctc ttgggatcaa catctgtgaa    23160
aagcagagct ggattaggca gagggagaag tcaccctgca atgccagctg aaggatagcc    23220
ttggctaagc ccataaggag gtctggaata gtttctcaga attgtcctac gttagactga    23280
gatgtccagg tctctgtacc ctcacatcaa tcagtcactg aatgtgtggc attctagaaa    23340
gggacatgac cttgagcaag ggggctgtct acagctgagg caatccttga aggggctgac    23400
agatgaagat tgtctgcaga gagccttccc tgcagctgga gcaaaagtc cttcattgac     23460 cgtgaatctg gacagctcat ctggtgccca gcacaaatat attttacttt agagtaaaat    23520
tctgtggggg aagatggaca atatacaagt tcaagaaaaa aaaagagatg acaaaatttt    23580
gactgtaaag aacagcatgt tcatgtattt tttaaaattg atgatgttga atagtaaata    23640
aatacagtat ttaaatcctt tggatcaata taaaagttgt atacaatttc ttctaaaaat    23700
attaatattt atagtaagct agatattgca tgctttgcag ctacttaaag gtatgataaa    23760 aaatttaaa ttttagatga aggggtacat tgtcaaaatt aatttaggga ataggtgagc     23820
aaaaaaggtt ggaagatcac tgatttaatc taacagatca ttgagccaat gagaatatcg    23880
agactcaaat atgttataag atttgcacat aatcacttaa tgattgaaat cagacctgtg    23940
aagcaatgat gttacctgtg catttttctt tacttggtgg ttgttaagaa ccattaagct    24000
actccctgtg aacacacact gaagagagaa aaggtctcat taagggcttc ttagcctagg    24060
gtatctggac accttcaagt tgcgtgcagc aatgtgtaca cgtatatgct tttctgtgtg    24120
tgtgtggggg gggtgcttct gtagcttcag cttcgtagcc actaaatatg ggacaaatac    24180
aaacaaatat tactttattc atgtgcttct agcccatcta attccattct caatttaaat    24240 tcattttttcc cttgaatctc ttctttggag ctcatgcatt tctgaccttc ctgtgtgctc    24300
tgacctcttc cctctttcaa aaatgtccaa cagtccccat gcagaaaaac ctccttgttt    24360
tatatctgac tcatattaag tcattcccga tctcaacagg gcgatctagt gtatgttaac    24420
tatgcacgaa ctgaagactt ctttaaattg gaacgggaca tgaaaatcaa ttgctctggg    24480
aaaattgtaa ttgccagata tgggaaagtt ttcagaggaa ataaggtaag gtaaaaatta    24540 tctcttttttt tctctccccc aatgtaaaaa gttatagtgg gttttacatg tgtagaatca    24600
ttttcttaaa actttatgaa taccattatt ttccttgtatt ctgtgacatg cccaccttac    24660
agagaggaca catttactag gttatatccc gggttaaat tcgagcattg gaatttggcc      24720
agtgtagatg tttagagtga acagaacaaa ttttttctgtg cttacaggtt atggctgtgg    24780
cctacaaaga agcatgcact gggtttatta ttaactttca gtatctttgt tttaaatatt    24840
ttctacaaaa atgtttacta aattaaattg tagtatgaat tgttataaat aatgagggaa    24900
aacaatttac acatagcaaa tttaaaaatt actgtcattt gatttgttaa tatatttttc    24960
tctttagtgg gaaattaaat tttaaaaaat tcccttttcga ctgtagaaca aataggaatt    25020
tggcctgtgg ggtctacttg cttattatat ttgtaagcta gtggtaggaa atagcaaatg    25080
ctcactacca ctaataagaa catttctaaa tctgatgttc tgaggatttt tagagcttat    25140
agtagcaaaa agaaagggaa aattctatcc gagatgtcct ttgttgtagg cctaatgaga    25200
aaaggttgaa gataaagttc tggtactcat ttaagtgtaa tattgaaaat tgatattacc    25260
gaatctggaa caaccaattt aaaataagga aagaaagaca ctgtgttttc taggttaaaa    25320
atgcccagct ggcaggggcc aaaggagtca ttctctactc cgaccctgct gactactttg    25380
ctcctggggt gaagtcctat ccagacggtt ggaatcttcc tggaggtggt gtccagcgtg    25440
gaaatatcct aaatctgaat ggtgcaggag acctctcac accaggttac ccagcaaatg      25500
```

```
gtgaatgatc aatccttgaa tatcatagga aacttaacat ttgaaagaga ctttattaaa    25560
gaatttcctt tggtacaatg gactaagcat gtctttttt attctctttg catttaagaa    25620
tgaaagaatt ttgaactcta aagtgattgg ttcaggcccc ttaccccctt attttgaaac    25680
ttgggcctgg tgggctttca aattcagact tattcagcta tttaaaaaac attatggtgt    25740
tacacatata ccataacttg cataacagtg cataggggg ctgggacaga atatggggaa     25800
aaagcatata aatattttg ttgcagagtg tatgaatact tacgctaagt agtaagtggg     25860
gggcggggaa taaggaatat aaacagactt atgtctactc aagtcaaatt ttgctttcaa    25920
atgagttcag gtcagatcag gttttgctgt taaataaatt cccccagat ttacagattt     25980 cacagtgtgg gtaagggaca ggagagcaga agttccataa acttttaaa tggccaattt     26040 aggatatagg gcccaggaaa tgcatattgc ttcatttctg taagataaca gagataactt    26100
tcaaagagtg tttcctaaat gccagcattt tacttgcatt aacaaccta aagctagggg     26160 gtgttattat ctcttattca cagggaggaa agtgagacta gaagtcagcc caagatcacc    26220
cctcctctga atgggcagtt ggattcaaat tcaggcagtc tggctcacag agtccacata    26280
gtagtcttat gctgaaaggc tcccctgtaa aacattaaca aagggagcta atttattttg    26340
aatgtgctca actatttaat gatgtttaca aaaatctgtg atcattaagt ttgtggggtt    26400
taaagctaac taaattttta aaacttgtat aaaatacttt gccaagtttt ctatgacatt    26460
tatgtcttca tctggtttta ctcttaaatt gtagactcct gtaaagagta tgtattttt     26520 ttggctttgt aaatcttctt agaacataat acattgtcag agatttttt ctttttaaa      26580 aaatgcaca tattacccta tagtaaaatt atataaatct acctgaactt catttgctcc     26640 accttttat ttccaagttt taaaaatgc agcttagcct aagctttatt agttatgcaa      26700
agtcaaaata atgaaaataa aatgagatta actggaatgt ttctgttgat tttcttcaaa    26760
tttgaatgat ggtattttag ggggaaatta tgttatttct atggggctaa tgtttattga    26820
attatatttt gtgctctata cattttatt ttctttctaa ttttactttt tattatggca     26880
taattctaac atatacaaaa gtagagacag tcatcaacat gttgtcaatc ttgttttatt    26940
tgtttatctc tccaatttta ttttgctatt attctaaaga atttgaaaac aaatcccaca    27000
cagcatatca ttgtgtcatt ttacccataa aaacaaggat ttgcagttac ctaagtttct    27060
tattagattg ttttaaaaac agagaaaaaa atggaaaaac aactctgatt tttcttaagt    27120
ctgaagaaat gataggatgt gtgtgcttat tttgaggtac agtttacatg caataaaata    27180
catagatctc aagagttcag ttcaataaat tttgcaaatt gcatgtgttt atgtcactta    27240
aaatagaata taagggcctt tccatcactc tggaaagttc ttttgtaccc ctttctggtc    27300
aattttctct gtgtcccta gaagcaatca ctatctagta tctagcatcg tgtattcgtt     27360
tgcctgggtt tgaacttcaa gtaagtggaa tcaaacagta gatttttttt taaagccttg    27420
cttatttcag tgtagtaatt tgagattttc tatcatattg tatgtattag ttttttttctt   27480 ttgatgattg agtagcattc cattgtggga ttatactacg gattgtttat tcattcttct    27540
gttgttagaa acctagactt tgtctaatat ttggctaata taaatgtggc tgttatgaac    27600
aattttgtac acgtcttctt gtgggcatgt gctcatcttt ctagagtacc caggagtgga    27660
attgctgtgc catagtgcac atttctgctt gacattgctt ttcaaaagag ttaccttaag    27720
tgattgtata atttttagcct agattatcac aagcaatgta tgaggatttc agttgctctg   27780
cattctcgct aacatttgaa ttgttaatct gttttacttt aacaattcta gcaaatgtga    27840
```

```
aattagaatg tatttaatgt gatttataga gaaccgtttg aatgaaactg agtttttact    27900
ggaaatatgg caattttttt tttcagaata tgcttatagg cgtggaattg cagaggctgt    27960
tggtcttcca agtattcctg ttcatccaat tggatactat gatgcacaga agctcctaga    28020
gtaagtttgt aagaaaccat ggatggctat ttgggtaatt ttcttattga cagttttcaa    28080
atgttaggct tttatctcca ttttttagta cttaaatttt ccaacatggg tgttgcttgt    28140
aattttatca gtataaaata gaagagtggt tctgttctgg aatttagtat atacatgagt    28200
atctagtgta tgacagccat gaaaatgaac ctttcagatg tttaacttca gggaacctaa    28260
ttgatcaatt gctccagaca ttgtgctttg aaaccccact atatttgtgt caagaccatg    28320
cttcctgtag gtgttctcgg gcaatgactc agtgtggcaa ggatactact gcaggcctgt    28380
ttctggaagg cactggactc ctctgatgca aaactttggc ccagggactc cttgatagcc    28440
tcgcttaaat agatgctgca cccaacactc ctctttcttt tcctcctccc ttttcctttt    28500
attcaatatt agacctacct tgcagtctaa ggactttctc agggtttcct agctctctcc    28560
tcattttcca cacatgcttt tccctagtaa atctcttact catatattcc tcttactggc    28620
tacgtctggg aggacccaga ataacacact atgagagcaa cttccatttt gtttttatct    28680
ctattcttct tccccttctg ctttcattat tgaaactttc tgctttcatt attgaaactt    28740
tcccagattt gttctgctta acctggcatt ggaactgttt cctcttccct gtgctgcttt    28800
ctcccattgc catgtccttt tttttttttt tttttttttt tgagacagtg tctcactctg    28860
ttgcccaggc tggagtgcaa tggtgcaatc ttggctcact gcaaccccg cctcccgggt    28920
tcaagtgatt ctcctgcctc agcctcctga gtagctggga ttacaggtgc ccaccactat    28980
gcccggctga ttttgtatt tttagtagag atggggtttc accatgctga tcaggctggt    29040
ctcgaactcc tgaccgcagg tgatccgccc tccttggcct cccaaagtgc tgagattaca    29100
ggcatgagtc actgcgccca gccaccatta ttctttagag gtgagagaac actggctttt    29160
ctaaaagtga aattgataga gaccaaagcg tctggccagg tagtcccttt tcttctttaa    29220
gttcaagcct ttcttactaa ttttattcca gtatctatga ggaagcactt tttgaccaag    29280
ggcaaggcac tcattttag aggtgaggag gctgacgtct ggggagtagg acacatctgt    29340
tcaatttaag ggcagattaa gaaagtaccc tggtctttct tccttgggc tataagattt    29400
actgcattgg ttaagattca ggaccaggca caacttttga tagcaccata gactatgcat    29460
ttgcctaaaa atatgtataa ataaagacta agtattcatg acatttaaaa gataaaagtg    29520
attttagcat tacttgtaat agtggaaaac tgtagacaac acaaatcttc aacaatttat    29580
atgtactcga ataatacatt aattactctg atagtaaatg aagtgattaa aagatatat    29640
atgtagtacc agaataatta ataatataga aaaatgctta tattattaag tgaagaaaag    29700
caaatttcaa aactatatat atatagtatt atctcagttt tataaaaaat taaacatgg    29760
ggctgggcgc ggtggctcac acttgtaatc ccagcacttt gggaggccga ggcgagcaga    29820
tcatgaggtc aagagatggg gaccatcctc gccaacatgg tcagtgaaac cccgtccgta    29880
ctaaaaatac aaaaattagc tgggcatgct ggtgcatgcc tgtagtccca gctactcagg    29940
aggctgaggc aggagaatca cttgaacccg ggaggcagag gttgcagtga gccgagatcg    30000
cgccactgca ttctagcctg ggcgacagag tgagactccg tctcaaaaaa aaaaaaaaa    30060
aatttaaaac atgaacctgt attatctttg taattacaaa agagggatgc ataatattat    30120
ggaattagat gtgagattta tttagacgtc tacgatttgg tctggtttac taggtcaata    30180
tcagctgtgc tctgattgtg taatggaatt atctgattga ttgaaaaata acaaacacaa    30240
```

```
ttcatctgac attactgtgt cagcctctgt aagccatttt acaaatacaa tcaccattaa    30300
taacataact ttcatgaaaa agtgcatttt acattcaaaa tttcataatt aaaaatagac    30360
actatttatc cacctatact ttctaagcca taatgaaaca gtccatataa gtggaattta    30420
gttttaaaaa attgtttaaa agaacatatg gtttgtttat gaatttcact gtgaaaattt    30480
actctcttgg cacacgtacc ttgggagtgt gccaagatac tcaattctga ggttctctca    30540
agtggttagc agtttagcat tgtgcactaa ttagaaaaga cagtgtttta caaatggaat    30600
atatcatgaa ataaaagttt attaataaat gtgtgagtaa atgaggagag atataaagtc    30660
atataatggc cgaagaatgc tgagaactta aataaaaagt tgatgaaatg tgagtgatgt    30720
taaaaacttc aatgttgact tgagtgggac agaaagggga caccatatat actgtttcct    30780
atttttcttt acatgtaccc tgaacacagt gtgattatgt ggttttaatt tgccttctac    30840
agtaacttcc aggacgataa ttatagtgcc aacggcaaca gtaatagcat gtatcctgca    30900
tggagtgcta attacgcttt agcacttact gttgtgctaa atgctttaca cacatctcct    30960
caattaacct ataaaacaac aatatgagtt agtattgtga tactcattgt aaccaatgtt    31020
cagagagtaa gtgagagagc cagggcccaa attcatgtct gatgcaaaag acactttggt    31080
aaacactact tactctctac tcaatgacgc aagcatttag tagccacctc tgttgattat    31140
agtattggct cattcttatg cctctgctcg ggagaccttt aatggcgtct cacagcccac    31200
tcactcaaga acatttata gaatgacttt tatatttcag gcactgtggt agaagtagga    31260
attaggtaaa gtcagtagta atgtcctatc ttgtattctt gattttagta attacttttt    31320
aaacttggtc agtttaacta atggtttgct aattttgttg atcttttaa agaatcaccc    31380 ttggtttcat tgattttctc tatttatttt attatttctc tttcaatctt tgtaatttcc    31440
tttcttatgc tttagagttt agtttagttt tctttgtcca gtttcttaag gtgaaagctt    31500
agcttaatga tttgagattc tttctatata ggtgtttaca gctatgtatt ttcctttaag    31560
cactgttttt gctgcatctc ataaatattg gtatgttgtg tcttcatttt cattcatctc    31620
aaagcatttt taaattgtat ttgcaagttc ttctttgacc cattggttat ttaggagtta    31680
gttgtttaat ttccatatat ttgtgaattt cctaaattta cttttgttat tgattgctaa    31740
attcctttta ttgtggttgg attagtaaaa gaagtatatg agtaataaaa tgattgtata    31800
atttcaacct tttaaattta tccaggctcg ttttacagac atgattatt atgaaaaatg    31860 ctccatgtgc acttgagtta cactattttt caatttcttt ctcaaggaat cttagtcatt    31920
ttatatccca gccagaatag tcatcatgcc ttacacttgc tctatgcttg cctgcctctg    31980
tgcctggaag gctcttcgcc ctcatttttc catgcccggc ccttattcat ctttaaaatc    32040
cagatcaagt gaaaccttct ttagaaagta attcctgatc tcacaagctg attcaagctt    32100
tcttttgtcc aaatttttta gaattttacc tttgctctgt gatgttctgt tttatattat    32160
gattggtttt atatgtattt tcttctgagt gatttataaa ctctttggtg gaaagactga    32220
gtcttgtata tatttatatt ttttagtgaa taaaacacag tgccttaaac atagtagaca    32280
acaagtcttc tccaaattgt caaatcaaaa ttaatatgct acaagataca gaattataaa    32340
ctcaatactg tctatacatt aattactgga catctaccat ctaccaaata tgtttggaga    32400
cattttccaa catttaatgg tactttctaa tatttttgtg gtttgaaatt ttaatattca    32460
actattaaat atttgtggaa tttatttttt atttataaag tgagaaaatg acctaaagag    32520 atttattttct aaagagaacc taagagaac ctaaagagaa atttcagtaa catttttcaa    32580
```

```
ctgaaacttc tccatgtatg tgcattattt ttttcattgg tatattagat tcttatatat   32640
aactattatt atgttctctt ctagttattt gtttacctcc ttgtggggac actacaatcg   32700
tggttttata ttgtgttgtt ttatggaaat atggactatt aattttttatt ctgaaaagga   32760 aatacattta caaagttcac aattcaaaag gatttatagt aaagttttcc tctcatccat   32820
ttacaccccc aaagcaactg atgttattag tttatagtgt attagcatag ttctctgctg   32880
cagagagagg tcccggaaaa agtgtgttgc tggtccactg caaaatgcag aggggttttat  32940 agatgagctg gtgaagaggt agtgtctgat ttatataagt catggacaaa ctggttagac   33000
caggtgtgtc atttgcatag ggtgtgaatt tctggtggcc ccaccctaat cttttattat   33060
tcaggtgagt tctctgcctg agctgcgtca tagtgctcat ttctctgtta ctgtgcatgt   33120
gataacaaaa ccaggaaga tagaccctct atgtgtacat gcctggcccc caggtagcct    33180 ttttttctt tgttttttt tttttgagac tgagttttgc tcttttgcc caggctggag      33240 tgcaatgacg tgatctcgct tcaccgcaat ctctacctcc caggttcaag tgattctcct   33300
gcctcagcct cccaaatagc tgggattaca ggcatgtgcc accatgcccg gctcattttt   33360 tgccttttt ttttttttt tttagtagag acggggtttc tccatgttgg tcgggctgat     33420
ctcaaactcc cgacctcagg tgatccgctt gcctcgccct cccaaagtgc tgggattaca   33480
ggcgtgagcc accgcgcccg gctccaggta gcccttact attggcacag ctgccagcat    33540
tctcccgcac tttcagcttg ctaatctatg tttgcagctc gattttcag gctgcttttt    33600 gttagaaaaa aaaataatt tattgggctg cttttttgtta aagggaagc tctgctgagg    33660 actctgttgc ccccattatc tgcttactaa atttctttct acctcctgta tcaatatttt   33720
atgtataatt aagtatatgt atattcttta cttgcctttt gcaaattttc tgtttattta   33780
atactctgct gttttgacta tgtattgtgc tttctaccaa tgtaaaatgc ctcttcatgt   33840
tgcttgatgc tttatacgtg gcattttatt gtaaatagtt taaataaatt ttataataca   33900
ttacttgaaa ttctgtttaa tatacaaact ccttagtgaa aagggaaaa gagagaggaa    33960 ttatttacac tttgatagag cattttaaaa cgagatgtta attctaatga attttccacg   34020
agaaagtgat cttactgatt gtttccttat tgcatgtgca gtagattcta ggttaagttg   34080
agctattcat atttcctcaa acaggtagac agggaacaac cacccgtgta caggcacaga   34140
agaaaacagg acatgacaga gcatgctgca ccgcacagcc tggagtgcat gagggtgcgt   34200
gaccgcagag aaagccttac aggacagatt gaaattctcc acttttgatt tcataactaa   34260
acatctcagt ataatatcag ataatgacat ttattttttcc aggccattat ttaagtggag  34320
ctgggtttaa ggtttggagt attcatttaa caggaacaaa atgcccgtgg taggcccaaa   34380
gaagtctgtt tttgccttac agctggattt tcataaaaat atagttacaa ttaaggtcga   34440
gattattcag tttgaacact cagtctctta agtttgtctg gaaacacatt tgtctctctg   34500
tagctgttta gtaaaagtat attgtttttac atgcccatat caagaataag ttaatccatc  34560
atcttaatac agtaaaggca gatatgttga agtgaaacta caagaacccc accatttcat   34620
aaacattacc atgttttctt tctcggtcac ctgctgaaag ataaccaggg accatggcat   34680
atactgggtg gtctgcctga atctttattt ctgaattta aaaaatagcg tgaagctttt    34740
aggggcttct gaaatgaaat cctttcttt gatcctcctg tcttcttagt aggtgtgtat    34800
gaaagtactt tgtaaaaaat aactatatac cagtgagaca ataagaatg gaaaatttca    34860 gagagttaga catcaagctc tttcttcagc acatgtctg gaaagcactt ttagatttac    34920
tactagatac tggtaaggca gatcaaattc ttatcaataa tttgaatctt aattatacca   34980
```

-continued

```
tttactagtt gcatgacttt gggcatgtta tctaagcctc ctgtgcccca tctgtgaagt    35040
ggaggtagca attcctcaga attatggtaa ggtttaaatg acgtattata ttcaaagcac    35100
tttgcactca ttaaagatat tatgagcaga tgctcaataa agtgaatcca ttaacatttt    35160
aatgcgttac ttcaaggttt ttttgtggct aataatgttt ttttgtgtcc aatagaaaaa    35220
tgggtggctc agcaccacca gatagcagct ggagaggaag tctcaaagtg ccctacaatg    35280
ttggacctgg ctttactgga aacttttcta cacagttaag agactatttt aattttaact    35340
cttttaaggg ggagacttaa agaaaaaaat actatagagg atgacagaaa aagtaaaatt    35400
tatgtaatac cagcaggaaa caaaactgca agttagaacc agtgtaattt tgcctgtga     35460 acaattagaa atctttaagc aagattgaag atttaaaaat tatgagtgtt gctggaactc    35520
agaaaatgaa taacccaaag tatggtgttt tgacatgctg agcactttga actaaaggat    35580
aaaagtcctt agatgcagct tcagaatcaa taattctgac ctcttacttc accccacaag    35640
agcagagtgt aagtttctct ctgaagttcc cttatctgaa gctcctgcag aaggaagaca    35700
atgactttcc ttcccctccc tgaaatttta ttaaccaggg aagattgaac tcatgtagtg    35760
ggaaggaaga ctgaggcata tcactttatc tgcacaggct ttgtcacaag ctgttgactg    35820
ttctctagtt ccattcaagt tccaaagaga attatttata aactattgcc tgctcttttgg   35880 gcccatttaa ctctcttgaa aaccatttac caccccctcaa aaccacctgc actcccccac   35940 ttcccccctcc tctatgaaga gggtgctagt taaactttag ccatttggcc tttgtttgag   36000
tctcatattt tgtttggctc ctgtatacac tggtgtgtta gtaagtttgt atgccttttc    36060
tcctgttaat caattttcag tttatttttac cagacttgaa ccttcaaagg cagaggggaa    36120
aattccctta aacctatag tgttaatctg ttaaccagtt tttttttta agaatgtctt     36180 ttattttgc attagaaaag tcaagatgca catccactct accaatgaag tgacgagaat    36240
ttacaatgtg ataggtactc tcagaggagc agtggaacca ggtaaaggaa tcgtttgctt   36300
agcaaatatt gatcaagtaa ctgttatgtg ctggatacta ccaagctctg ggagtgcaaa    36360
gtgaatcaaa acaaacaaac aaacaaacaa acgaagaaaa tcggtggaac tcacctaaaa    36420
acaaaggaaa taagtatgaa ataatttgt attgtggtac aggtggtgaa taaaagtgaa    36480
tgtttggtgc taggctgggc agatgaccaa ggtgaatgat aaattgtgca ggcctcaatt    36540
aaaggatcaa gggaagcagg gtagggaaag atgtgttttc ttccgagttt tctgaatttt    36600 ttttaccat atttttgcat aaatatcttc atgataacta taaacatcta tataaaaat     36660 cacactctta gaaaattaag ataatcttgt attaatgaat cctttcatag ttttattttc    36720
taccactaaa gccactgata aaatatatgg acatatgatt tccatagaag ttcagatgat    36780
ctactgatta atacatttta tacgtagtct tagttcatga aggctcagtt tcttatgaac    36840
tattttgttc tgtatttctt accaaaacag atactattaa atgcatatta aacatattaa    36900
ttgcatgttt cttacaagca gccagtgatt tattttagat caagaatatt gatatccttg    36960
ttgtttgcat attctaaaga gtactaaaca atatataagt ggctactgtt gaataatacc    37020
gagtacctat tttgtgccag ttccatgata agcattggaa atggggagat aaaagaagac    37080
acagacccaa gacaaacaac tgacagtttg tgaagggagc catatgctta agggtgatca    37140
atgctttatc actcctgaga gctgggtagg caaagaaatt ccctcttcta tagaaaatac    37200
ttgagctgta ctttaaaaac tgcatagagg gagaaaatat ttgagctgta ccttaaaaac    37260
tgaatggagg gagaaaatat ttgagctgta ccttaaaaac tgaatagaaa gaataggaat    37320
```

```
tggagaactt cctatgtggc cactatgttc tcttactttg aatatattag aaagtggtaa   37380
gttaggtaag agaggagtaa tagagttaca aaaaatgtga acaaggataa ccttaaactt   37440
tcttaattac ttaatgtagt acttataatt atagtaatac attgaaatat atatttgctt   37500
tatcacattt atgctttctc agatagaaga aacacatatt aaaatcagaa ataacatatt   37560
ttcacaaatc ttggggaacc tagccttttt tttttttgag gcgtgagtgc tttgtattta   37620
gatgctattg agtcgtttgc aattttctct tttattgacc tgaaatgaca aataatcttg   37680
tatctatgct ttctagacag atatgtcatt ctgggaggtc accgggactc atgggtgttt   37740
ggtggtattg accctcagag tggagcagct gttgttcatg aaattgtgag gagctttgga   37800
acactgaaaa aggaaggtaa tacaaacaaa tagcaagaaa aaaaacagcc tatctgagtc   37860
tcagtttagt cttctgtaaa gggagtataa aaatactacc tcaaccatta catgtgtttg   37920
gtaaaaatac taatacaatt ttcagtgttg gttggttaat tatattgttt atttatttt    37980 gcatttattt atataacaca tatattattg atatttatgt attaagtgat aatctgaaat   38040
aaaggaatta tactgttaat ggttgttctt ggcaactaag aagatgaaga tgggttacat   38100
cactagagaa aacacactga aattagatta taagccaaag cttcctagtc agagactgta   38160
agcagacgtt cctccgtctc ttctaacccc agacctcaga ttacgtgtac aaagtaatta   38220
aggagataga tgctctattc agagaaatac aggtcttagg tctaatggga ttctgtcaaa   38280
agtttggaat ctgtgttctc acatcctgag ccctggtgtg ctctcacaaa aattaggttt   38340
acactcgtaa catcaccact ttagtcattt tagaatcttc atatgaaagc caaagtaaaa   38400
tttagttcaa atgtttgctt tttaaaataa taattacaca ttgagagcag gaagttcatt   38460
ctctttattg accctgcaaa caaggtgtct ggggctgtaa aatgtaatct atatattttt   38520
atcaaccata aaaacaataa tgtatgttgt ttgcatagta tttacttttt ttttgagaaa   38580
cttttttata tgtcctatctt ctttgaagtc atagcaacta gggagaagac atatttactt   38640
atcttctcat gttacagata ggttaaccaa ggtttagaga atcaagtaat tcccccagga   38700
ttatgtagct agcatgtggc agcataagag aatcagggct gaaactcaaa tttctcacta   38760
ccagtcctca aaaccatgat gtctctattt aaaataaaat gtaaaggcgc tcagttcttt   38820
tttctacaca gctatcttat atttgaagaa acaaacaat ggagacctaa atttacataa    38880
ttcatgaagt aggtagtgtt taattttatt acaaaaatgt ttcatgattt ttctaggaaa   38940
ttcctgtggt aactatacaa aacatcactg tgacaattac agaatatgcc aaagaaatgg   39000
aatgctgatg aataataata ggaaatttga ataatactat tgacaaaaac aaaagactcg   39060
agttaacagc tatagtatac acattcttaa gcacacatga atatttacta agatgatgac   39120
tactcgcaat tttgaaagca cctactcagt gctttctaaa cattattcca tttaatcctc   39180
ccacaatcaa gtggtgtctt catctttact ctcttgttcc ttgtatacag atgaagaaat   39240
ggaagtttag taggtttgaa taactttccc tcagtcacgc tgctagtgag agaaccaggg   39300
tttgaaacaa gatcttgcct taactccaag gtcagtgttt ataacctccg agacacatca   39360
cccctctgct gaattatgtg gttttcagca acagcaaaca ttgctgttgc taactgagcc   39420
cttgttgatt aattctggca gagaatggtg tgaaatcata cggaccagct gatattgaac   39480
aattgttcat ttgatgtcag aacaacagga aagagttcta aaggattttc tttcagttat   39540
atctgctttc agaataccaa atgcatctag aaatttcttt ctttgttcta ggcagttgca   39600
gaccaccaat gacttcctat gcatagcgaa tcattataaa cctattagaa tgttttatga   39660
tcttgcaaga ttttactgt cacatgtccc cccttttcta tgtaattgtg ctattttgta    39720
```

```
ttgacaactt taaaatctta caaaaaaagt tacgtaagta aagattttt  actacaattt    39780
gcccttccca aaccatcaat gactttttt  ttttttttc  caatctgggc ttggtagtgt    39840
cctgggtata ttatgaattt tttttctatc atttatatat acacatacat tttagggtgg    39900
agacctagaa gaacaatttt gtttgcaagc tgggatgcag aagaatttgg tcttcttggt    39960
tctactgagt gggcagaggt tagttggtaa tttgctataa tataaatttt tataaaataa    40020
agtagccagg acttgtttgc caagcacata aaaataagaa gtgaatataa tgagaaagta    40080
ttcaaagttt ttccccaaa  atctgaagta acatattctt gttcaaaaat cagcaataaa    40140
aatctctgtt gctaaagaac taagttttgt ttgaacctt  tagagccact taatgtcaat    40200
tgtcaaaatt aatttatctt tatttcctgg gagtatgaga gtaaataagt agatatgcta    40260
gaaaccaaac atcaaaacaa ggagttagtt tcttaatcat attgtagttt attcttcaaa    40320
atattgtctt agcaaacatg aacgacttaa cagactttc  agtgaatatc ttggcataaa    40380
catgtcattt aaatggagaa tcttgtctga ttcaaaggga attaagctat ttcaaattta    40440
tgaaaaatat gaagttaaat tgtctctatt tcctgaccat gaagccaaat tttcctgtat    40500
catgtttgat ttctatcatg attctattac gctttccaaa atatctccta aagctaacta    40560
tacagagtct cgctctgttg cccaggctgg agtacagtga tgtgatttct gctcactgaa    40620
gcgtcagcat cctgggttca agcaattctc ctgcctagg  ctcctgagta gctgggatta    40680
caggcatgtg ccaccacacc tggctaattt ttttatgttt aatagagaca gggttttgct    40740
gtgttggcca ggctggcctc aaactcctga gcttaagtga tatgcctgcc tcggcctccc    40800
aaagtgctag gaatacaggc gtgcgtcacc atgcctggcc gtaaggtata cttttcattt    40860
atctttctta attcataatg acctgctcta tgttaaatta tgctaaaagt aaggcagaaa    40920
tttccaccac agaatattta ctaagccatt tgaaaagtaa ttttacctgc atgtattgtt    40980
ggctttatat aacagaaacg ttagctataa agtaaatata tgcaaagtca atgtttattc    41040
cattaatttc cagtcatgct gtaaatattt actggctcct ttcatactcc agatattatg    41100
tgcctgtgga ctttaatttt ctttgaaaaa aaaatggtg  ctcctgtaga cttagtcaaa    41160
gttttataag aaagaatttt gccactatct ggaagaacct aatatttga  cggtgtaatt    41220
tgtgtctttc aaattatttt tttcacttac agttgtattt ttttcatttt ttatcttata    41280
gtcagaatgc ttaggaaatt atgtatttta gagactcaga attcacattg atatctcaaa    41340
aaaactttgc tacgctttgt tctaaaagtg tgcaattatc aatattgacc aggagatggt    41400
accatcctac aggagagcct gacttctggt caggagatga tttaagttca cttatttttc    41460
gtaacatgaa atttaactta aaatttcata cacttaaaat accttcattc catatgaatc    41520
agacaagatt ctctgcttaa ataatgagat gtttatagga agattttcac tgaaaagtct    41580
cttaggtcat tcatgtttgc taagacaact ttttgaaaga taaactacag tatggttaag    41640
aaattaactc attttccact taccataagt atatggacaa tttcatctta aatattagct    41700
tttaacaagt tttgcttgtt gtttcctacc agtaatcttt attgaaattc tttcaaagca    41760
gctctttat  gagaatttct tatgtcaaat tgtcgttaa  tatgggtcag ctcaattaga    41820
aatctacata cattaaatgt agatgtgcat tttgtggggg aggggagtg  ggttataact    41880
ttatatttat agttttcctt tttattatag gagaattcaa gactccttca agagcgtggc    41940
gtggcttata ttaatgctga ctcatctata gaaggtgaat atcgttggtc tcataagaaa    42000
agatgtgatt aaactaggag cagcagtcta gttaataaat tatgcactaa caaggaaggc    42060
```

```
tatgcattaa tgtgtggtta gggaatctac tgcaacctct gacaggaagc agtgtatgaa   42120
ccctagttga gagttgggtg agccctaggt gaacaggtgt ttcttttctt ctttcctttc   42180
cttttgtttt cttttctctt ttcttttctt tcttttctta cttttttttt gctttgaagt   42240
atagagtact aattcagaaa agcagcattc tttgattagc ttcatctggc agatttcttt   42300
ttatatacag caggaattta gtaagtatct gttgaatgat taactcaggg acctaaagag   42360
ttctataatt tagaatggtg tagaaaaaaa gtatcatttg tggggtgcgg tggctcacgc   42420
ctgtaatcgc agcactttgg gaggctgaag cgggtggatc acttcaggtc aggatttcga   42480
aaccagcctg gccaacatgg tgaaaccccca tagctattac aaatgcaaaa attagccggg   42540
cgtggtggcg cactcagtat agataatata ctaaatcaat cttgaattat aatgtatgca   42600
ggtactttag aaagggtagg ataaaaccac tctgggagtt cagaggaaag aataatagaa   42660
acttcaggaa aggcttgaga aagggaatag gcatttgagg ctgactttga agaatggaaa   42720
tatatttaat aagcaaagga ccaaactaaa ggaaatctca gattgatttt catgaaaatg   42780
aaagagtcca ttttcactac aatccagctc cactaatata tctatatctt gaccatatgc   42840
aacatcccag ccattgctct cctgttctct acactcagat tgctcttcaa cacctcttta   42900
tgtgtttaat ccttatcctt agaccctcct ttgaaatgtt acttttttcag ggaagacatg   42960 tcttcatggc actcatcact gtcattatta agtaattatt tgttttacaa gtaatagact   43020
gtattcttta acaaggaaca gacagtatct tgcttattca ctcctagatt cctaacgtct   43080
tattaaataa atatttgtgg tatggttgca aaaaaaaaaa aaaggactaa atgaatgaag   43140
ggggaatttt ttagaatatt ttctttactg tattagtaaa tttgccatgt caacacttgg   43200
aacatgagac cttgatggag tcacgttggc attttctttt tcttttttctg gtttttttgt   43260 gtgtgttttt ttgtttctgt tctttttctg tttttttgttt gtttgtttgt tttttctgtt   43320
tctgttcttc ttctgttttt tgtttgtct gcttgtttgt tttgagtcag ggtctcactc   43380
cgcagcccag gttggagtgc gtggagcgat catggctcac tagtcttgat ttcccaggct   43440
caagtgatcc tccaacctca gcctccttgg tagctgggac tacaggcaaa cgctagacat   43500
ccagctaatt tttgtatttt tagtggagat gacatttgac catattaccc aggttggtct   43560
caaactcctg gctcaagct gtctgtccac attgttctcc caaaatgcta ggattacggg   43620
tctgagccac agcttccaac cttccttttc ttctttgtca atgcctctga gctacactgt   43680
tctgaaagtt agtttacaca gtacatttgg ttattctttt ctccttctct tagggtagtg   43740
gctaagagct tgaccttttgg cgtcagatgc ctggattcat tcctgccct gcaacttcct   43800 atttgtgtga cccaagctac ttactttctg tgcctcagtt ttctcacttc taaatataac   43860
ttctaagagc tcctatctca aaggctcctg taagggcaaa aaaagttaca tttgcaaatc   43920
tcccagacct gtgccttgca cagagtaaat gtcaaaaaaa gttaactttg attagtatca   43980
ttacacctac ttaaaacaca taaggtgaaa tatatacatg tatatatatg tatattatat   44040
gcccacccag aataaatact ccaaatatat tttcttgaaa catagaataa cgttctcttt   44100
attgatagtt ttttctgtt tttttttgtt gttgttgttg ttgttattgt tgttttgaaa   44160
tgagatcttg tagtattgtc caggatagtt tcaaactcct gagctcaact gatcctcccc   44220
cgtcagcctc ccaagtagct gggaaaacag gtgtgtggca ccatacttgg ccatagtttt   44280
ttaagatttg atattttaat gtattttaaa aactcattaa gctttgctac ttatgtcatc   44340
cctggcttga aattgctcca ttgtgtctct ataattttca aaatcgagaa caaaggacag   44400
gaggtactat atgattggga caccattcat ctcacttgtt ttatattttt acattgtatt   44460
```

-continued

```
aatgtttctt tctcaaataa tacaaataat catagattct gaaatttcta atgttaaaat    44520
gtaaaatgta caaataaagc gaaaatcccc aatgcaaact actctcaaac ttagtcctct    44580
ctccaaaggt attactgtcc tcagttttgg gtgtttccat catgttggca ttaatatata    44640
gaatttagct tcacaaagca ccaagagcgt agtgggtgct atctcaggtg ctttacacgt    44700
aaaaaaatta ttcagtactc acaataactc tctgagataa gtaagtaaat attttattta   44760
tcccttttgt ataaaagaag aaactgacac tcagagaggt taagtaattt tcccaaggcc    44820
acacagctag tgaagggttg agcttagact caaatcagac tggtctgttc caactttacc    44880
cctctaacca ctacactcta ttgtctctca ccaccttata caggtatttg gtatcatatt    44940
acagctaaat gcttctacaa cttgcctttt tcattcagca acacattatg aaaaactttc    45000
catatcagca catatctcgg tttcacttaa aaaacaaaca ctaccaccag acaacaaaaa    45060
tctacaatgt attcaatagg acaaattttg tatcagtttt ctagctgctg gacagcttgc    45120
ttcagtttgt tgtggttaat attattttat ttgcatgctt ttttggtata atgtgaggag    45180
agggtagaga gctacaagta tatttatttg gtcttcagat gtgggcaatt aaattgtaat    45240
aaatgctgcc aaactactcc actccccaat ttccactctt ataagcactt ctgttttaaa    45300
aattacattg gctgtttgta catatttatt cttccagata aattttagaa tctaaaatca    45360
aatctttaag ttccataaac aattctgttg tggtgtcact attttaaaag cctcaacttt    45420
tgctgttctc aaacatggat ccgaggcttt gggataaaag ctagttgcca tcctctgagt    45480
gtttcatgtg cttttacatt tctgggcatt cgcacaggct atgcctttag ctgcaaatac    45540
cattttcccc cccaactgtg tcctggttct agaaacccca gttcaagagt ccctctcca    45600
agtttgtgaa tttgtcttga cttccctccc ccaaaactcc tcctgagtca gcagcccctc    45660
cctgtgctgt gttggcttcc caagaacacc tctcctgggt gcttcacttg attgtcacaa    45720
ccaccagccc cctcctgagg aatggggact gaaactctaa gaagagcacc tggttcacaa    45780
attcattgtt acaacaaata ttgattggtt aaatgccaga ttctaggatt gttctaaaca    45840
cttggggtat ggcagcaaac aagagagtgc accttatccc aggggactta tcgtctagtg    45900
ggagggccaa taataaaaag acaagtactt aatatgtttt atgttaaata gatgagtaat    45960
atagagaaac aagagccaag gttaaaagag agagtggcta aaattagggg gtaagagagt    46020
gctattttag gtagggtgat caggggaaat ctctcagaaa acatgacat tagaccagag    46080
gaggaggagt aagtcatgca gatataatgc agaatactgt tccaggctgg aaggacagtg    46140
tgtgcaaaga tgctgaggga gtattcttgg gcagaatgta aaatgcagat tttgagaggt    46200
gacctagggt ttcatatatg gcagtgtggg ccatggtgag aatgatggac tttacagagt    46260
tagttgggaa gccattggag agttacagtt gaaatcaggt ttttaaaacaa tcattctggt    46320
aggaatttag cagtggtctt tgaagaaaat aataacagaa agaaattaaa ttttaaaatc    46380
tattcttttc ttatttttca ggaaactaca ctctgagagt tgattgtaca ccgctgatgt    46440
acagcttggt acacaaccta acaaaagagg tatataatta catataattt aagaaaaccc    46500
aaattctaca aatgatgttt tcttgaggta ttatgttaaa cataggtggt gttttataac    46560
ttcttgtctt catttcatat aacatatatg acatcacatc ttcacagacc atcacatcta    46620
gtaaactgtt tacacagatt gcctcatttc tcaccacacc agtgtgaggt agcccattag    46680
tagcatcatg tctaccatct ccattcttaa aacagtgaaa ctgagctcaa agaacattgg    46740
ccaccaaagt cacacacaac ttgtacggta gccgaaccaa gacttggtcc tatggctcaa    46800
```

```
ctccttaatt aaaaaacttg tttatactct tcagtatagt gataccaatt aattcagaac   46860
acaggaatca ttaaatgttc taactgattg agaaagaata ttcataagaa taccaggtgc   46920
tggcttccag ggacagaggc tagatgagat cacaattaca tttttttcaga tagggattat   46980 aaataaaatt taaatgccat taagctttgg tttcaaaaga atggaatgga ggagtgacca   47040
agatgactga ctagaagcaa ctatggtgtg tggctctcac aaagagaaat tgaaggggca   47100
agtaaataca gcaccttcaa ctgaaacgag cagatactca cattgggact aatcaaggaa   47160
acaacccaac ccaaggagaa tggagaaaag caaggcagga cgatggccca cctgggaatg   47220
acacagagtc aagggaacct cccccacca ggaaaatgat gagcgaatgt gcaacccag    47280 gaaaccatgc ttttccatg gatctttgca acgcttaggt cagcagatac ccttgtgaac    47340
ccactccacc agggccttca gtctgataca caggtgcatg gagtcttagc agaacagcca   47400
ctcaggcatg cacagagaca caggagcttt agatacacca gctttccagg cttcatggca   47460
aaagtaactg caactccagc acagcaggag gttagacccc catacatacc cataaaaaag   47520
aggctgaatt caagggcctg agcagtgatg gtctgcaggc cccacttcca cagcacttca   47580
caggataaga cccactggct tggatttcca gccagccact ggtagcagtg ttgtgcctat   47640
ctgggaaaga gctcttgggt ggtggtgggg ggcagggagg tgggggtgga ggggtgggct   47700
gccatctttg ctgtttgggt ggcttagcca ttcccacctt taggctttgg agagcccaag   47760
atgactgggg gtggaagcgg taccccagca cagcacagtg gcctcacaaa aacgtggcca   47820
gacttcctta taaagcagat ccccaactac gttcctcatc aatgggtgga gcctcccaac   47880
tagggtttct ggctaccccc actggtgttc tctggctaac agaggtttta ggacaccctg   47940
ggatggagct gccaggagga ggggcaaacc accatctttg ctgtttgggt gacttagcca   48000
tcccaggttt cagacttcgg agtgtccaag acaaccgagg gctgaagtgg accctcacca   48060
cagcacagtg gctctacaaa aacgtggcca ggctacttttt taaactgggt ccctgatcct   48120
tttcctcctg tctgggtaag acctcatagt ggggtctcca gccacctcct acaggtctgt   48180
tcaggctggc aacatgtcta taactcccatt ggacggaggt cctacagtaa gaagcaggct   48240
gcattcttta ctgtttcaca gccatcaccg atgattcctc caggtactgt aaaatctgag   48300
gcaactagcg attggagtcg accccccagc acaacacagc agccctgcag aaaagtggct   48360
agactgttta aaaaaaaaa aaagaaaaga aaaaaagga caagctccac tcaaaggtca   48420
ccaacctcaa agattgaagg cagataagcc cacaaagatg agaaaggatc agtacaagaa   48480
cattgaaaac tcaaaatgcc acagtgccct ctttcctcca aatgactgca tcacttctcc   48540
agcaaggttt cggaaccggg ttgaggctga gatgcctgaa atgacagaag tagaattcat   48600 aatatgata gggacaaagt ttactgaggt aaaggagcgt gttgtaaccc aattctagga   48660
agctaaaaat catgttaaaa cattgcagga actgacagta aaatgagcca gtttagagaa   48720
gaatagagct gaaaaatact acaaatgctg tcacaagtat tgatagcagt atagaccaag   48780
tgaaggaaag aatcttagag ttgaagactg tctttctgaa ataatacagg cagacaagaa   48840
tagagaaaaa ggaatgaaca aaaccaccaa gaaatatgtg attatgtgaa gagactgaat   48900
ctatgactga ttggtgtact tgaaagagat aggaagaatg gaaccagctt ggaaaacata   48960
ttccaggata taatccatga gaactttccc aacctagcta gataggccaa cattcaaatt   49020
caggaaatgc agagaacctc agtaagatac tacttgagaa gatcatcccc aagacacata   49080
ctcatcagat tctccaagga caaaatgaga gaaaaaatgt taaaggcagc agagggaaag   49140
gccaggttac ctacaaaggg aagcccatca gcctaacagt ggacctctca gctgaaaccc   49200
```

```
tgcaagccag aagagattgg aggccaatgt tcaacattct tagaaaaaag aaattccaat   49260
ccagaatttc atatccgacc acattaagct ttatacgtga aggagaaata agattctttc   49320
aagacaagca aatgctgagg gaatttgtta ccaccagact gtcttaacaa gagttattga   49380
gagaagtact aaatatggac aggaaagact atcaccatcc acgacaaaaa cacactgaag   49440
tacacagacc agtgatacta taaagcaatc acataagtct gcagaataac cagctaacat   49500
catgatgaca ggatcaaatc cacacatttc aattctaatc ttatatgtaa atggtctaaa   49560
tacaccaatt aaaatacata gagtggcaag ctggataaag aaccaggacc tattggtatc   49620
ctgtcttcaa gagacccttc tcatatgcaa tgacacacat aagtcaaaat aaatagatga   49680
aggaaagtct accaagcaaa tagaaaacag aaaatgcag gagttgcaat tctagtttct    49740
gacaaaacag actttaaacc aacaaagata aaaaaaaga caagaaggg catcacgtaa     49800 cggtaaagga ttcaattcaa caagaagagc ttactgtcct aaatatatat gcacataaca   49860
caggagcacc cagattcata aggcaagttc ttagagacct tcaaagagac ttagactccc   49920
acacaataat agtggtagac tttaacagcc tattgaaaat attaattaat tttcaagaca   49980
taaaataaca aagatattca tggcctaaac tgagtactgg atcaaatgga cctgatagat   50040
atctacaaaa ttctccaccc agaaacaaca gaatagacat tcttctcatc agcccatggc   50100
acttactcta aaattgatca cataattgga agtaaaacac tcctcagcaa aagcaaaaga   50160
aatgaaatta aaaacgtctc ttgtactgcc gtgcaaattc aaaatcaaga gtaagaaatt   50220
cactcaaaac tatgcaattc catggaaatt gaataacctg ttcctgaatg acttgtgggt   50280
atataatgag ataaaagcag gaatcaagaa gttctttgaa actaatgaga caaagatat    50340 gacacaccag aatctctggg acacagctaa ggcagaatta aagggaaat ttatagcact    50400 aaatgcccac attaaaagtt agaaatatct ggccaggtgt ggtggctcac acctgtaatc   50460
ccagcacttt gggaggccga ggagggcaga tcacaaggtc aggagatcga gaccatcctg   50520
gcaaacacag tgaaaccccg tctctactaa aaatacaaaa aattagccag acgtggtggc   50580
gggtgcctgt agtcccagct attcgggagg ctgaggcagg agaatcgctt gaacccggga   50640
ggtggaggtt gcagtgagct gagatcatgt cactgcactc cagcctggac aacagagaga   50700
gactccgtct caaaaaaaaa gaaaaaaaca ttagaaagat ctcaagttaa cagcctagtg   50760
tcaaaactaa atatactaga gaacaaaagc aaacaaaccc caaagctagc aaaagacaca   50820
aagtaaccaa gaccacagct gaactgaagg tgttggagac atgaaaaacc cttcaaaata   50880
ttaacgaatc caggagctga tttttttgaaa aaaattaata aaaaatagag tgctaactag   50940
actaataaag aagaaaagtg ataagattca aataaacacc gtcagaaatg ataaggggga   51000
atattctcac tgacccaca gaaatacaaa catcagagaa cattataaac acctctatgc     51060
acataaacta aagaatctag aagaaatgga aattagctgg gtgtggtggc aggtgcctgt    51120
aatcccagct gctcgggagg ctgaagcagg agaattgcgt gaacgaggtt gcagtgagca   51180
gagatcgcgc aattgcactc tagctcaggt gacagtgcaa gacttcatca aaaacaaaa    51240 caaaacaaaa acagaaaaaa aaaagaaaa ggaaaaagaa aaaaaggat aaattcctgg    51300 aaacatacac cttctgaagg ctgaaccaga agaaattga atccctgaac aggccaatca    51360
tgagttctga aactgaggca gtaataaata gcttaccaac caaaaaaagc caaggaccaa   51420
atggattcac agcttaattc taccagaggt acaaagaagg gctggtacta tttctattga   51480
aactattgcc aaataattag gaggagagac tcctccctaa ctaattctat gaggccagca   51540
```

-continued

```
tcatcccaat accaaaattt ggcagagata caacagcaac aaaaattcag gccagtatct   51600
atgatgaaca atgatgcaaa aatcctcaat aaagtactgg caaacagaat ccagcagcac   51660
attagaaagc ttatccacca caatcaagta ggcttcatcc cagggatgca aggttgattc   51720
aacatatgca aatcaataaa tgcagttaat cacataggca gaactagaaa caaaaaccac   51780
atgattatct caataaatgc agaaaaaagc tttcaataac attgaatatc tcttcatgtt   51840
aaaaactatc aataaactag gtattgaagg agcaaacctc aaaataataa gagccatata   51900
tgacaaaccc acagccaaca tcgtactgaa tgggccaaag ctacaagcag tccttttcaa   51960
aaccgacaca aaataaggat tcttctctaa tcactcctat tcaacatagt attggaagtg   52020
ctggccaggg taatcaggca agataaaaaa ataaagctca ttcaaataaa aagagaggag   52080
gtcaaactat ccctgtttgc agatgacatt attctatatc taggaaattc cattgtcaaa   52140
gcccaaaagc tccttaagct gataagcaac tatagcagtc tcaggataca aaatcaatgt   52200
acaaaaattg ctagcattcc tatacactaa caacagacaa gccaagagcc aagtcacaaa   52260
ttaccactca ttcacaatta ccacaaaatg aacaaaatac ctatgaatac agctaactca   52320
ggaggtgaaa gatctctaca aggagaacta caaaccactg ctctaagaaa tcagagatga   52380
catattcaaa tggaaaaaac attccatgct catggatagg aagaatcaat atcattaaaa   52440
cggccatatt gccccaagta atttatagat tcagtgctat tcctattaaa ctattgttgg   52500
cattcttcac agaatttgaa aaatctgttt taaaattcat atggatccat aaaagagccc   52560
atataaccaa ggcaatccta agcaaaaaga acaaagctgg agacatcaaa ctatactatg   52620
aggctacagt aatcaaaaca gcatgatact ggtacaagaa cagacattgc ggtttattgt   52680
atattattga atgactttgg caaccctact ggcaagaaac aatattaaat tgaatcctta   52740
cccttaacca gcttacttct ttttattttc tttgttgtga gatgagaaat agttttgact   52800
gtagtatctt ttaattcaga aaaatagaca aaaagatcat atgctatgcc attcatctaa   52860
agacaatggc ttggtatgaa tttggtgtag cctgtttatg ctatgcactt catacattta   52920
tttttataat atagttcacc tatatataat cacatgagta ttttcccact tgtcagaaac   52980
ttataattct tgatgactgc taatgtatgg atagcatccc ttgttttttgc tgaattgtgg   53040
cttagttact cacttctggt taatggacat ctagttttta atatatctga tttgtaagta   53100
ttctcttttt ttctttttaat ttgtgtagct gaaaagccct gatgaaggct ttgaaggcaa   53160
atctctttat gaaagttgga ctaaaaaaag tccttcccca gagttcagtg gcatgcccag   53220
gtaaacaaat gaatgaagtt tccactgaat tcagtgtggg attgttttga aaataaaagc   53280
acattttctt tcaatcatta agtgaaaaat taagtttcaa aatggtctaa atctgataa    53340
agaaaagcat tactttggtt cacaaataaa atattactat gtgttttgta gttaaatctg   53400
caggatatca aaatgtgatt tctctttaga atatgtaata tatacatatg aacatttca    53460
gcagattata aagattggtc atttcttata tgaaatgcgt gggatgagaa gtgttttgga   53520
ctttggattt ttttaagatt ttggaatatt tgcattatac ttactggttg aacatcccta   53580
atctgaaaat tcaatactg aaatgcttca gttagcattt cctttcagtg tcatgtaggt   53640
gcttaaaaac ttttggattt tgcagcattt tttaaaatgt tctaatcttt aattttgtg    53700
agtatgtagt aggtgtattt attttttggg tgcatgaaat gttttgatac agattttgga   53760
tttttggatt agggatactc aacccatgat agagataatg gtgaaaagta attttcctcg   53820
tttttctgcc acctcatcac cttgtaatta tccttttct gaatatcata tagttaacaa    53880
atattttgct tattgcaata aaaatgcaag catcatttca acattggttg tatcttcaca   53940
```

```
agcaagggaa gaagaataaa tatctcagtg ctctgagttt atcgatgtca acagcactat   54000
ttatattatt aagggcaaaa tttatgtcca aattatctga aaaatatttg cttttcactc   54060
tattatgtac aacaaataaa gatgataaat ggaatgaaat aatcttaagg aaaatgtttt   54120
ccaacttcag aaacctttaa caaaatgtga cataaaatag tcattcctac acgaaatagt   54180
ctcatagaag gagatatttt gtgatcaaaa ttatattctt ttcatgtttt tgctgcatgt   54240
ctaaagctgt atgtttaaaa ttacatttat aatagtaaga atggggttta gtttaatgga   54300
catgtaatct gtgcttaatg aacaaattac tttgaaataa ttctgttgtt ttatctctaa   54360
aaggataagc aaattgggat ctggaaatga ttttgaggtg ttcttccaac gacttggaat   54420
tgcttcaggc agagcacggt atactaaaaa ttgggtaagt gaatctcaaa ttatctaaga   54480
ttatttatga atatgtttta actaaacaaa taattctgac tccaaaaagt gactcaagca   54540
ttagaggaat agaaaatttt gaaagcagag ggagaagtct caatggttga cagtatcact   54600
actacgtagg ataactccta tatcttgtat tccaaccota aattcaagtg tcagttggta   54660
tcaatactca tgtctgcaaa tgtgaacttc tgtgtactcc tttaaacata ttttctgttt   54720
catttggtgg cattgcattc actcagtcat ttaagttgga aatgtaggaa ttgtctttga   54780
tttcaccctc ctccttattc aaaattagta tctccccatt atcattcaaa attaagagtg   54840
tatttggatt ccatctctt actgtatctc caattattaa acaaataaca agtcattaaa    54900
caaatgaaaa atgatatata tattagtctg ttttcctgct cctaataaag acatacccga   54960
gactgggtca tttaaaaggg aaatatgttt aattgactca cagtttcata tggctgggga   55020
ggcatcacaa tcatggctga aggtgagtga ggagcaaagt tacatcttac ctggcagcag   55080
gcaagagagc atatacaggg gaacttccct ttataaaacc atcagctcac atgagactta   55140
ttcactatca cgagagcagt gcaggaaaac tcgtccccca tgattcaatt acctcccata   55200
aagtctctcc catgacacgt ggggattatc ataattcaag gtgagatttg ggtggggaca   55260
cagagtcaaa tcatatcagt ataatacact gtgtacgtgt aaaagtcatg attcccttc    55320 ttttgttgtt gattatatat atatatatat atatatggtt ttcattttct tcaaagtaaa   55380
ttgggtacat agtttataaa atgtcaagta gttttataag aacagtggtt tataattaaa   55440
aacagttgtt tcttatttcc atttcatatt cataccaccc ctgatttctg ttcatcagat   55500
gaaacctttg tcaacttttta tgatacatcc atatttataa gtaatatttt aatcctgata   55560 cttttttcaat tttaaatttt atgttataaa gaaaatcat tctcacagtt ataaaaatgg    55620
taaggaagag ttcattcaaa actattccaa taagaatatt gcaataataa gagatcgagc   55680
tcaactccaa atacagaaaa gacatttggt gatttagagt tgacattaag tttctgtaag   55740
cctttcctca tgggctatcc ttcccagatg gaaaatcttc agtctcctgt ctgtgaggta   55800
ggaggttagg cagagttatg caggaggtga tagtgaggat aaatattaat attgtctaca   55860
ttttactacg aaaaaattac aacaaagaaa agtcaaatga ccacctaaag ttttggtag    55920 taagtcctga agcctagatt caaacccggg cagggtaatt ccagaatccc agtctcttca   55980
acacatcagt acataaaatg tcctttata ttaataataa aaaataagca tcttaagatg     56040
atcaaaagtg ataaaccagc aattcacagt ttgaaaagtc cttccttcta cctatacttt   56100
tggttttcct gacacctgtc tgggcctccc ttctctctcc ttagtgagat tttggatcca   56160
ctactgcacc cctcaccact cagactctcc agccttcagt acactgcttg tcagacaatc   56220
atttatccat ggaattttag tgattaagca atttagtgtc ttctcctata taatattgtg   56280
```

```
taatacttat gtacttgcct ttaacaattc gtcttcttt tatccaaatg caagattgtc    56340
ttgtcttttt tttcagattc ttaaaacatg aatctaagaa tgcaatgttc tgcattctta    56400
gaggcaagcc agtttggtcc ctttcaaata attttaaat aatatttgtt atatcatata     56460
cacatatttt aattgataca agcctggaat gtgtttatgt atcataatat tagccattta    56520
ggatgtagct tattgagatg cttaagtact ttccttgatc catcactgac caatcttact    56580
aatactaata gtaaatatgg tgctaatcat tttttgtaag ctatccctat aagagatatg    56640
ttttgttgtt ttttctgtag gaaacaaaca aattcagcgg ctatccactg tatcacagtg    56700
tctatgaaac atatgagttg gtggaaaagt tttatgatcc aatgtttaaa tatcacctca    56760
ctgtggccca ggttcgagga gggatggtgt tgagctagc caattccata gtgctcccctt    56820 ttgattgtcg agattatgct gtagttttaa gaaagtatgc tgacaaaatc tacagtattt    56880
ctatgaaaca tccacaggaa atgaagacat acagtgtatc atttggtatg ttacccttcc    56940 ttttttcaaat tcctcatctg tatggttcta ttaatctcct aaatataatg ggctatctta   57000
ggtcatttat tatttattgc tatttcaagt gatccaatat tctgtttatg tctataaatg    57060
tattttccat tttatggatg ctcacgtctt ataatataaa aatataaata ccttgtaaaa    57120
cacaaaagat gatggcttct atattgttcc ttttcttgaa ctatagagca gtgccattag    57180
aaattatgtt ctttaagcat ttgatgatcc caatttctat ttcagattca cttttttctg    57240
cagtaaagaa ttttacagaa attgcttcca agttcagtga gagactccag gactttgaca    57300
aaagcaagta tgttctacat atatgtgcat atgtgtgtat gtgtgtgtat atatatttat    57360
ttaaaagtaa actaacatga ctgttgctga actagctttg ggaatttctt gctgttttct    57420 ttttttttaaa tttgtttac tttaagttgc tggatacatg gacagaacgt gcaggtttgt    57480
tacataggta tacaagtgtc gtttcctgct gttttctgtc tttccactct agcacgtcct    57540
atgtagggct gccccatctc aaaagaccta ctttcgacat tctgagtggc aattgtgccg    57600
ctcagaaatg tcagtccctc cctcctgaca tttgatcagt tacaaaatac tctgcttaac    57660
attgaaggtc ctctactgtg tgaccccagc tgttttccagt tttatttctt gcttttttcag  57720 tatctgtaca tcataactca gccagactat ttatttttca aagcatgatt tctttctacc    57780
tcctttgttt ttgtcattac ctccacatag agctccttat ttccacttcc atctggcaaa    57840 attctgtttta tccagaatag caaatattgt gaagccatta attttggaaa tgttaaacat    57900
ttaggattaa ttctgtgtaa gattacacaa gtacaacaca atttgaacaa aattttaaga    57960
tggaaggaaa aatacttggt gagaatacta aggtaatttt tttaaagtat aattttgagg    58020
gcagagatct gtgtattaaa tatagtatca tgatataaat atcaaatccc caggagctga    58080
tgtaaggaca cataaaaaga ttacagtaga tgatgtagaa ataggcttgg tgatctataa    58140
ggaaatatta gtaataaatg atacagcaaa aattaatggg gaaagattac tcaaccataa    58200 tattatga actatgttag tacctgctat aactgctata aagtaaatt cagatcgca      58260 cttcacattg tatgctaaca taaacaacag gtgtaaagaa ttatttagta aaaatggaaa    58320
tttcttgaaa gatgccaggt ttagaagcaa tggggaaatg atgcaatcag atttgagacc    58380
atttgaaatg gttcagaata cgaaaattaa tattcacaag aaaaattaag aaagttgaaa    58440
acttattttc tagcaaaaat ggagagtaat atatacatta taaaaatatt ttttgaaaat    58500
taatttaaac agtccaaaag aaccagctga aaatatcggt aagaaacaag acaaataatt    58560
ttaaaaatgt tgtcaaagat acacctgcaa agaaacatgg caaaatattg cagttcacta    58620
atgcataatt cagaaataca aatgaaagta atgtgatgtt atttttataa cacattaata    58680
```

```
acaatttaaa ccttggtttg cccattgctg tagctggtac actgaagcat atgctctcca   58740
tgcttttctg atagcattat gaattatttt agcctttttg aaaaagatag atacatattg   58800
ctaatgtgtt caagagctgt cacagagtcc tgtgctttga catagtattt ccacttcttg   58860
gattatttct taggaaaaag tctcaattt ggaaaagaaa ggctgcctgg agaaagattt    58920
gaagtataaa attataatag caagtaattc aaaataacct aatgcctaag agaagagaaa   58980
ttactaaaaa atttgatatt caccaatttg aacattttat aatcctaaca atggattatt   59040
agaaatacaa cataatagaa gatacttaga ataaaatatg aagtaagcaa aaaggttgta   59100
aaattgtaaa tataatttga ttaattttta tttaacaaat acaggaaaaa ctttaaggga   59160
attaatgaat tattataata attgtgctat cctcagggaa tattggaaga attgttttcc   59220
tattcttttc aattctttat aatttttata tgtgagtaaa aaagtcaaca ataagaaata   59280
cattttaagg agatcccaaa caccatgtat cctataaaac tggttttctt tttgtattta   59340
aaagaaaaaa tgttttctcc ctctgacaaa atgcctcatg gtttgaattg tggtttgttt   59400
aggacactta ttgtttggca cactcagctt cccccttcctt tagtatttct atatttgttt  59460
tattttctgt aagtgatagt aaagatacac tctgttccct atatgatact tacaaattct   59520
gaaacacctg agcagtgctt tgcacataat agtaaattct gactaagtaa attaaactga   59580
atgttgaatt tctcaaccaa aactttgaaa tctaaggaag agacatgact ttatcctgct   59640
tttcttgtat cacttcttgc cccatcaaag aatataagac gttaacacag gatacagaga   59700
aagagaagtg tgtgtgtgtg tctgtgtgtg tgtgtgcacg cacgcgcacg cgcgcattta   59760
cgtgtgtgtg gccacatgag ttttttgtact tgtagcaatt cttttgtgaat ttgattccga  59820
aacccattgc atcttattga aattatcctt cattcgattc tctcaactgt ttatcggagt   59880
tgctaacagg tattctgtgt ttcatttacc tttatactat cacagaatct gaattcatga   59940
tgccaaatac ataaatgtta aaaatagctc aaatccaaat tatgggagtt taagttgttc   60000
ctatttcct tttgtcggca aggtgcagtt gaaagaacaa tatcaatctc ctatttcact    60060
ctaaactt ctagtgtgaa tttaggcaag ttatttaact catgatcctt tgttatctca     60120
tctacaaaat ggggctgtta ccctacccaa cttgcagaat tgctctgaaa attaaaaatc   60180
acattttgta taaagattca gaacagtaat tggcacatag gaaatgatca ctaaatgctc   60240
ttttagtaaa actaaattat gaaaagcaag aagtaaatta atgaacaaga tgattcatgc   60300
tttcttattg taatgatttt tctcagttaa ttaaattgtg aaataattgg tatattaaat   60360
tcagtaactc attgttgaag tattcagagc ttgctgataa actttcaatt atattgaatc   60420
attcttatta taataacaac cccaacactc cttttagaat gtaagttctg taaaagcagg   60480
gagtgtttga taaatagcag gtatccaaat attgttgaaa gacttaagta atcaccatct   60540
gttgtgttca taataggttt agctttaaaa ataaaaggaa tattattagt tatcacttgg   60600
taaatattta taatttgcca ggcatcttac taaacattag caagtcatct tattttaata   60660
ttgatattac ttcagtgagt agattgctag gatacctaag gtgaagaaaa tcttgcctat   60720
atttgtatat ctgggttgat cagttaatta tgccaatgta aataaaaatc actattattt   60780
tttccatttg cacatacaac tgtttctgtg cttttataag cctgagcagt atagtatttt   60840
ataagatttt aaagatgtca tagctatgta tgttattgtt cttaatttgc atattacaga   60900
atgttaaaat ttacaattga catttgaaca acagtgattt gaactgcaca ggtccactta   60960
tttacgaatt ttttcaatt aatacagtga gccctctcta tccatagatt tcacattagc     61020
```

```
aagcaaacac agatggaaaa ttcagtatta ttcactgtaa tccccaggta ctcaggaagc    61080
tgaggcagag gaattgcttg agctcaggtg tttaaggcta tactgagcta tgattaagcc    61140
actgcactcc agcctgcgca acagagcaag actccatctc ttaagaaaac aaaataaaat    61200
acagtattga aggactaaaa cccacatata tggagggctg actattcttg ttattttta a   61260 atatggaaaa cttttattt  tgccaaatta atcttttat  tttcaagctt acatttgaaa    61320
atgttagcat tgcatacata aaatgatttc attaaaaata tctaaaagta ggatggacat    61380
aaatctagaa caaaagtatt ttaactgagt aaattcattt atgtggaaaa aatctcaaca    61440
agcatctttc ttttagcttt gatatattag aacttttatc acagaatgat gctcactcta    61500
caagcttgaa tctgagaaac tcagatgtag ctaatgaaaa actaatgaaa aatataaagt    61560
aagagaatta tagaaactta aaaaaaaact gttacattcc atttggacta ctagccatgt    61620
gttccacaaa cattttctat tttatataat tgcctatctc attgtcttaa caacatgaag    61680
actaagatgt gaaaggggga ttaagcatgt ggtaagagtt atactggggg aagctaaccc    61740
aagggagatc agatgtggct tcagattcca catacacagc tacatttcct cactgaggca    61800
gagcaagtta atccagaaag tcatatcagg ctccaagaac gctgtactta aaccattctg    61860
aaaatcactt gaaacgatat aattttaagt aacttttaga cttaaatctg gatcattata    61920
ccgagagatc aatttaattt gtttggtagt ttgttcattt tcaccctgtt aattccacag    61980
aggactcgtc atttacatta ggtatacctc ccaatgctat ccttcccccc tcaccccacc    62040
ccacgacagg ccctggtgtg tgatgttccc caccctgtgt ccaagtgttc tcattgttca    62100
attcccacct atgagtgaga taacgggtgc agcacaccaa catggcacat gtatacatgt    62160
gtaacaaacc tgcacgttgt gcacatgtac cctcgaactt aaaagtataa taataaaaaa    62220
aaattccaca aaggaggagg gccgactttt cacatacatg tgtcctcctt gcaggacttg    62280
agtatgcaca aattttggtg tagagggtgg tcctgaaacc aatccccgga gataactaaa    62340
ttcagttttg ttctgaaatt tttatttttct gggtagaaac atattttcat gaagttataa    62400
ttatattcat tttcttttctc agcccaatag tattaagaat gatgaatgat caactcatgt    62460
ttctggaaag agcatttatt gatccattag ggttaccaga caggccttttt tataggtaag    62520 aaaagaaaat atgactcctt tctgtaatat cactttttct tctaattatt tttattttt    62580 tcactgtgga aaaatattg tagttgattt cttgcaagca aatagaaaat ttcaaaatat    62640
atgtagtaag tgatagttgt attgtttctt catataatgt aatatgattt ttgcatatct    62700
ttattttgag tatctttgtt ctgattataa aagaatataa atttattta gaaaatatag    62760 aagatccaga aagccatgac aaaaaataaa aatctcccca atttttatcag aaaaatataa    62820 aatcattgtt atattctggt gtgtataatt ttagctcctt ttctatttta aatatatttt    62880
tacttatgta tacacagaac ccaaacatct ctctatatat aatgtatata ataaatatat    62940
atttatttat tcttttccct aatgttgata tttagatatt ttatttcctc ctaaatcctg    63000
acagttggat ttttttctgc caaacattga ctgtccccag gttgatcttc taaatattgc    63060
agaatgagat agatcattgg acagccagaa atggccctaa cttttctttct agggattatc    63120 aaagggtcgg gcttgggagt aagagcatct tccaagcagg ttgactggat cagatcacca    63180
gtagcagcat attttatcc atccccaccc ccccttttt ttcctaagag acagggtccc    63240
actctgtctc ccaggctaga gttcagttgt gcaatttag ctcactgcag cctcagactt    63300 tgggctcaa ccaatcttcc tgcagcagcc tccaaagaag ctaggactac agtcacatgc    63360
caccatgccc agctaatatt tgtacgttca tttgtagcga cagggtgtcc ctatgttgcg    63420
```

```
caggctcgtc tagaactcct ggcctcaagc aatcctccca ccttggcctc cctaatatat   63480
gggattacag gcatgagcta ctgcttctgg cctatttac atctttacta tggagtttgt   63540
ccttctcttt ctgtgggcta ttacatgaac tgtcatagcc cattctataa aacattttct   63600
gccttggtca catggaacat tacaaaattg tttttgatga ttcttcaaac tctatattaa   63660
gtattctaac atggtagtgt gacttttta aaaaagacaa aaaaaaacca caatagaggg   63720
ttggctgatc acaagcaaga ctgtaatgat tacaattgtg ctataatata gggggtagca   63780
tgatatatta aaaaatcagc agttacttgt cgtgtgcctt gagacaaatc atttagttac   63840
ttgatctctc agacctcagt ttccttctct gtgaaatact aatatcaact gtgtagagtt   63900
tatttctaaa catcagaaaa attgcaagta aacattaaat accaagaatg attgctgtgg   63960
ttactatcat cattgttagt tttgtagcac tgaaccactt taatttattt gtttgaaata   64020
aaaatataat taattactat agatttcata taatagtctt cagagatgat tgaacttgga   64080
agttcagttg acaggtggct tgttcaaatt gttataggaa tatgcaatcc aggaattgca   64140
gagtgctctt gtgtttctct tgtatatcat ttgggcacct aataaacagc aaacgatttt   64200
atcaacaggc atgtcatcta tgctccaagc agccacaaca agtatgcagg ggagtcattc   64260
ccaggaattt atgatgctct gtttgatatt gaaagcaaag tggacccttc caaggcctgg   64320
ggagaagtga agagacagat ttatgttgca gccttcacag tgcaggcagc tgcagagact   64380
ttgagtgaag tagcctaaga ggatttttta gagaatccgt attgaatttg tgtggtatgt   64440
cactcagaaa gaatcgtaat gggtatattg ataaattta aaattggtat atttgaaata   64500
aagttgaata ttatatatag ttatgtgagt gtttatatat gtgtgtgttt atattgttta   64560
tcttctccct atggattaaa actgaatttc ataattataa gaggttattc tgaagtggaa   64620
aaatttaact cagtattaaa tctaaggaga atggcctaat atagtaaaac tctcatctgg   64680
cattatcagg gaatcaagtc taatctattc atgtcacttc acacagaaga aaacatcagt   64740
atgtcagaga gcacactggg gaatatgcac aagattatcc caagccagag gcctcacggc   64800
ctacctggcc agcctgggct gagaggatca ctatctcagc acactatttg ggaaatggat   64860
caaatcacac ttttagtaaa tgttatcact ctatagcata agaaataatt attttttatt   64920
tatataaaag gctatagtat aaaatatatg tatagtaatt aaatgaacac ttgtgaacct   64980
aatagccata tgaagaaaat aacatttcta atatctttgg atgccccatg tactaatgac   65040
agttatgctt ttgcattttc ttgaattta tgtttattta tctttcctct gtcattattt   65100
ataatttat cacacatggc tgtatccttt acatgttttg gcattatgta ttttgaact   65160
ttttgtaaag acaatcatac catgtgtaat tttcagggac ttgatttttt tcattgactt   65220
ttaagggttc aaatatatta tcactgtggc tgtagtttgc catattttgc tgatatagag   65280
cattcattca catgagggta ggattcaggg tccatttcat ttaattatca tgacttatcc   65340
tgaaataatt taaaatctct aacaggtgat tatgtaaacc acactagatt tttctgttgc   65400
accctgtatt attatttacc ttttacagat aagaaaactg aggttaaag aaattgatta   65460
agttttgcgg agcgctaagg agttaaaaga aaatgaaaa atgggcttag ctggcaggaa   65520
cagaaacagg ggtagagggg aatgaatgtt ccaagaatag ggtcaactgc aaatggctca   65580
cttagcaccc aagcatcctc ttacaagcac ccagctcaca gcccatctgt aaccaagcat   65640
cctgtctgca agcattcagc ctaaggagca cccttataaa actccctcga gtccctgcct   65700
ctttgcagac agccttccct ctgctgtctg gccagttgct cccttgcaat gtgtctcccc   65760
```

```
ttttctctaa ataaatatgc ctttctaaac tcattactgt cttggtatta aggtaaattc    65820
ttttactacc tgcacgtcag cctcacagtt gttgaccatg acaactttct caagaaaaca    65880
atgggcagat gtttgttttc tgaatcccac cgataagcat taggccatac tatacttcct    65940
tctttaacta ttgaaaaag attgaaggtg actcttcatg tcagaatttg tagaaacaaa     66000
catgaactaa atcaaagtat tatactcatc tatgaggtgt gttctagaaa aaaattaaaa    66060
tatttttaat tcctcttatt tccagccttt tacccatatt tgcctttgaa aaatacttag    66120
tcaagaaaaa tcactggctg cttttctttct ttctttcttt cttctttcct ttctttcttt   66180
ctttctttct ttatttattt atttattgtc aaagtctggc tttgtcacct caaaccgctg    66240
ggctcaagca atcctcccac ctcagcctgc caagtagcag aagctacaaa caccagccac    66300
catgccttac tcattttaaa aaaattttg tagagacagg gtcttgccat gttgcccagg     66360
ctgatcgtga actggccaca agcaatcctc ttgtctcagg ctcccaaagc cctgggaata    66420
aatacatgag ccactatgcc cagcctcctt ggctacttct taatctgtag acatagcatt    66480
cttggacttt aaactgcatg ctgaataaca gagctctaga agataaaaat tctaacttat    66540
ttctccaagt aatttgattt tttaaaattt cagtctttt aaattggggg tggttacata    66600
ggcatttata tttgttgaat tcttttgtc atatgttaaa aatatgtgca ctttattgta    66660
tttaaagtat aaattttaaa tttgatataa acaaaaagat agggcatag ataaataaga    66720 atgttcccta atggttcatc tgaattccat tgtttcaaag taattaattc tcattctcct   66780
tatgctaact ttacctaaag taggggaata tttgcagagg gaactttgta gacagatttc    66840
tttgcttcgg aattttgaaa aatagaaaat gtggtaatac tgtctccaat gtaatgatga    66900
aatggagtag taaatgaaca tatttagga aaaaatgctt gtaatattta aataaaatat    66960
atatttttcc tctgctaatt tttattacta aaataaaatg cttttttttt ttttttgtg     67020 agatggagtc ttgctctgtt gcccagcctg gagtgcagtg gcacgatttc ggctcactgc    67080
aacctccacc tccccggttc aagatattct gctgcctagc ctcctgagta gcagggacta    67140
caggtgtgtg ccaccatgcc cagctaattt ttgtattttt agtagaggca gagtttcatg    67200
ttagccagga tggtctcgat ctcttgacct ccttatctgc ctgtctcggc ctcccaaagt    67260
gctggaataa caggcgtgag ccaccgcgcc tggccaaaat gcttatttt atacagaagt     67320 ataaaagta ggaagcttaa gtaccatttt ataaccctct gtccttccc ttaacatatc      67380 accatccaga gatgaatacc gtcaacattt tggtagtaat tatttgagac attttttcttc   67440 aaatacacac aatacttcga atgaaaaatg aaatcatgct atgcctttat ttttaagaaa    67500
acttttaatt aacatataca tacataaat gtacaagtct taagtgtaca gcttgatgag     67560
tttttacaaa atgaacacac tggtcattca gcatcaagat caagagacag ggtatcaaca    67620
aaactccaca agccctcatc acatcccctt tacatcacta tctttcatgc tgacggatat    67680
ccactattct cctgttctaa attctaaata atgtctagtt ttgctgtttt gaaatttctg    67740
taattggaat cacgtagtac ttgtattttt gtgtttggct tgtttcccta ggaactatgc    67800
ttgtgaaata cattagtagt gtgctagtaa atcagctcta aagaaggggg aaagccttgg    67860
tttgcagcat ttactgattt ctgtgatgca aatattccca accatggcag atatcaagga    67920
aacaacaaga agttactgaa tgtgcagtct gaaaggggaag gccacaattg ccttttgtaa   67980
gctggcagaa gcaggctgca gcacaccact ggacactccc tgtctttcca tgtagcaata    68040
gttcattcat tttcagtgtt gtagatttat cagttgtata aatgtttcac aatttattta    68100
tctattctct ccttagtaga ttttagatt ttctccagtt cttggctatt agaaattgta    68160
```

```
cttcagtgaa ctttcttgtg catatctttt ggaggtcata tgtatgtatt tttgtgggta   68220
tttatctaga agtcataggt atgtatatgt tcagctttag tagaaacttt tagagttttc   68280
taaggttttt atgtactatt cataccagaa gagtatgtgg aattccagtt tctctctgtt   68340
cttgccaacc aactggtatt ttactgatga caactaaaat ggagcagctt ttcatgtggt   68400
tgcttctaat ttgtactctt ctttttttgc actgaccaag tgttttgtcc cattttcgct   68460
tgggtattct gccttttttct tttttatttg taggagtttt tgtatatatt atgactataa   68520
ttttataatt tattttattc aataatgcag aattttacat gagcatataa aagatctatc   68580
ttatcatttt gtcactttat agtatttata aaatatattt ataatatttt aaagaataga   68640
cataaaatga ggtatttcat ttttattcat atcaaaattc ttatcaaata agtgatttac   68700
aaacatttca tttgacattc tagttgtctt ttcactttct tggtaatatc acatgagtac   68760
ttaaaacaaa ttttttacg tgtacctgat tcacatgaga atttaataga tgctccctta   68820
cttacaatga tttggcttag gattttttcaa ctttatgatg ctgcataagt gatatacatt   68880
cagcaaaaac catacttcaa gtactcatac aatcattttg cttttcgctt tttgaacagt   68940
attcaataca ttacatgaga tactcaacac tttataacaa aataggcttt gtattagatg   69000 attttttttca actgttggct aatgtaagtg ttctgggatg tttaacttag gcgaggctaa   69060
gttataatgt tcaataggtt aggtatatga atcatacata cctgatttta aatttatctc   69120
agtcagtaac tcgcatatgc aaatatgggc aaattgttcc attttgcctc atttgtaatc   69180
tttaccattc ccagaaaagg ctcttctcaa agttaccaat ggtctaggtc ttttcaaagg   69240
cagtgatcag ttttttgatt ctgttttgtt tgtgtgtgtg tgtcagtgga caactgaac    69300 catgtgacgt ggtatagcca taagaattct ttagacccat aagaacatct gttcttacca   69360
aacaggaaaa acatgacaaa ggtgtaggtt tccatcaaga tcagaggtat tttgacctat   69420
gtaagaagat atttttaaata atataaaagc caaagaaaat taaatccagt gatataaccc   69480
tgagtgggtt tgcagaattc tgtgggaaaa aaatattata ggtgaaatcc aaactgaaac   69540
atgttatgta cctgaaccat aagattgcaa gaccatttag tgagttgata tggtgactac   69600
agataagact gaatatgttc tatcacagta acagatatca gagtccctgg tcaatatctt   69660
aggcgaatat gcatattcca accatctagg ggagtatcct caaagacttt gtggtaacac   69720 tgttgttttcc tttgtgggaa agcctacttt tacccttaaa atatttaaag taaacataga   69780
aatatttagg taattaaacc cattagttaa aataagttta agcatattta gtatttcaaa   69840
attgtgatgc gtactgttca gaagaatatt gactattcaa tgaaactttt ttttaatgta   69900
agctgtataa attgagtagt tgagttcacc ttttgagttt taaattcaaa gtacttacgg   69960
tatttatatg cactgtgact ggaatatgga aaagaagtta aaatcgggcc aggcacactg   70020
gctcactcct acgatcctag cactttggga ggctgaggtg ggcagattgc ttgagctcag   70080
gagttccaga ccagcctggg cagcatggtg aaaccctatc tctacaaaaa atagaaacat   70140
tatctgggtg tggtggcttg cgcctatagt cccagctact ggggaggctg aggtgagagg   70200
atagctcaca cctggaaggt tggagctgca gtaagcctga gtgcaagcca ccgcactcca   70260
gcctgggtga cagagtgaga ccctgtctca aaaaaaaaa aaaaagaaa aagaagtta   70320 agattactca taattataaa ttaaatatat tagacttaca aaaattaatt ttaagtactt   70380
agaaatgttt gttggacaga ccattgaagt acctaaaata ttaatagaat acatttataa   70440 atgttatttta aaatgcttaa cagtatttaa ttaactatgt aaaataagac gaagactatg   70500
```

```
agatatcctg taagttattg ttaaaattta ttagatttct aaatagagta agatatgccg   70560
agaccagctt ggtctgggag accctaaccc agcggcgcta gaggaattaa agatacacac   70620
acagaaacat agaggtgtga agtgggaaat caggggtctc acagccttca gagctgagag   70680
ccctgaacag agatttaccc acatatctat taacagcaag ccagtcatta gcattgtttc   70740
tatagatatt aactaaaagt atcccttatg ggaaatgaag ggacgggcca aattaaagga   70800
ataggttggg ctagttaact gcagcaggag catattctta aggcacagat cgctcatgct   70860
tttgtttgtg gcttaagaat gactttaagt ggttttccac cctgggcagg ccaggtgttc   70920
cttgccctca ttcctgtaaa cccacaacct tccagcttgg gcgttagggc cattatgaac   70980
atgttacagt gctgcagaga ttttgtttat ggccagtttt ggggccagtt tatggccaga   71040
tttttggggg cctgctccca acaaagatat atatatatat atatatatgg aatatcaaga   71100
agctaaagaa cagggttttt ttaaatgtag cttcaatcag ttaaatattg attataaaaa   71160
ttaaagtaaa actctgaaga gttttctgtg tataaacctg tcctcaagga tataaaaaaa   71220
ccgtcagtgc agacactcag agagtttaac aaagttaatt gctaattcct tcattaacac   71280
tttctcttct agactgtatg acaccattgt cctctgaaac tgactggcgt cccttctcag   71340
tctcctttgc cagccctgcc ttttttacca gacctttaaa tgttggagtg ttccagggct   71400 ctcccttttgg ccctgctctt ttcattctat agtgtctctt gaggtgattt caaactccaa   71460
gtaccatcta tatctggcca caactggcta gagttcacca aacacatttc cctattgttc   71520
tgggaataca gctaggccgc atgtctcagt ctcccttaaa ggtaggggtg tcctcattat   71580
tgtgtaagaa ctaataacat atgagaggaa gtgatgtatg tcccttccaa gcttatcccc   71640
ctccaaaagc ctcctataca attttcccct ctctttgttt accctaatgg tttctgaaac   71700
acacagaggc tctagcagag gatgcagagg ccctggagaa tgatacagcc agacagaaag   71760
agcctagatt actgaaccat tgctaggagc gatcaataac acccaaataa actttatagc   71820
aataaaagaa taaattattt ttttaactga atggattgat ttggtacaga agctggtgca   71880
ctaaacactt ctgatcttga ctgagacctg catttttttc gtatttgttg tccacttaga   71940 cttctcccctt gagattcagc attaaatatg taattactta attgaggtct ccaactggaa   72000
gtctattagc tcaagcttca catagtgaaa gataagttgc tctacaaccc actgcccaac   72060
aaatttactt tgtgcctccc caataccaac ccaacctatt gccagacttc cctccctgtc   72120
gtacctgaat aaatgatgac accactcttc acagcagttc aggctaaaat cctgtcactc   72180
ttgactattt tactcataac cagcagctac ctctacttag tcctaaaagg gaaaaaaagt   72240
catcttttcc ttgtaaacct ttaccttttac tctattttc tctgctaaac aaagtttaaa   72300 cttttttatca agatgtacaa atctttgcaa aatctctcatac aaatctagtc ttgcgatgaa   72360
cttctacctt gaaaacctca tgcccctggt cactgtgaaa tggatgaaga gtagatatct   72420
gactcagctt tggagaatat ttttgccaag gtgttgaatt caagtttaaa gtgactggaa   72480
gcattacatg agtggctagc tagcttctac ctcacatatg aattgactaa caaagaaagc   72540
aggattaact agaaagcaga ataaagcaag tgcccagaga ggagcagaaa caatattaga   72600
aatggagcac tccttcaatt tataatctcc aagatcttga ttactgcatt tcctgagacc   72660
cattgtcatt tctacatttg gcttctgtga gacattcttg tgtctttata ataagcccct   72720
accaccatta ctcccctctct tttttgctta agctaactgg aattggttta tttttatctac   72780 cgtatagaat cctgaataat taagcttccc agcctcatct ctaattcact agtactcccc   72840
gattcccttc tgccatcaca tatgaaaact ggatacattg aacttcaaat ggtttctaga   72900
```

```
atattgttgg ctattttgtg atattaggat ttaaaaaaat ctgtctcatt tgcttgtgat   72960
attcgctgcc acttagcttt ctggaaatgt tttagtcatg cattagggct cgtctcaaat   73020
atcacccttg cattggactt atttggacct tctgcaggaa gatatttta ttccatcttt    73080
tgtgctgtca tagtactcta tctacccatc tgtaatgaca tgaaggacat gaaatcatta   73140
ttgaaagatt ttcttcctca ttagactgac gcaaaggcag gaatgatgcc caattaattc   73200
tgaatgcctc aagtatacta cacgatttga cctacagttg tatgtctatt tgtcaaatga   73260
aggaagaaat acatgaaaga agaaactgtg ctagccctgc caattattat tttagcagat   73320
atcttatttt aattgtttaa gtttcaaatg atctttgtgg tatactggct tatttgttta   73380
gtttatttct cagcacattc tttgcatatt ttattaccca tcagcaataa aagacaagaa   73440
gggaaagaag gaattgtaat aatcagctct tcacaccctt atttctcttc cctaatattt   73500
ccccaagttt ttattttgtt ctcacaatta agtctatact acttagaaaa taagattaaa   73560
tcttctatgc tcctttggtt agaaattttt ctgggatgga tttaaagttg aacatctatt   73620
gcaacttaaa attttgttta aagttgctct ttctttctaa tagcaattat gttgggctag   73680
aggataaata gttggagata acggaatttt ctcttagtgt tattgctgcc tccattcttc   73740
tatatcttgt aatggactct ttggagatta taataataat gaatactagc ttaatattta   73800
tcaaccacag agccgggggc tgagccaagt ggttttatat acattgcctt atttactcct   73860
tttctcagca ctgtgactat agtactttca taatacgtat aactttagag gtattttgag   73920
ttactaagaa ataacatgaa aacaagctct ttgagcctgt aagattacta gctaggacag   73980
ctttgtaaga gaaagacctc tttacccttc aggagtagca ggaaaagtat gctattcaac   74040
aggattggct tatccacctg actctgacat aatcatatat gaaatgatac tgatatcagc   74100
tttctttctc caattgttga taatttggtt cattatttct tgtccttcct catgagtaat   74160
ttgatctgtc ctgttccagt tcttcccttc cagagcagga aagtcaaagg aaaggaggaa   74220
gttgtgtaga agaaaagttt caaggggcat tctccggaaa gactgaaaca ttatgctaac   74280
cagtcaaaac atattttgag aagttaaatt tggattagaa gtctctttct ataatttttt   74340
tttcaatttt taaaattttt tatctttaaa aaatgtgttt ttcaattttt atcaaaaagc   74400
tcgagctttg tcctagctga gctcacagga aaaggaatgt tttcagatct cagatctgaa   74460
taagtggggg aacagcttat ctctgagggg gcaagctggt aagagggtcc catttgaaaa   74520
actcagaaac aagaaaggat tttaagtggg aaccaggagt ttctcttcaa aataatcctt   74580
tacactctgt tcattaaaat atatatatat ttttatatat tatatattta aatatatatt   74640
tatttaaaaa tatattatat tatatataaa atatatatta tattttatat acatatatta   74700
tattgtatat ataaaatata tattatattt tatatacata tatattatat tgtatatata   74760
aaatatatat ttaaaatatt atatatatat atgaatttaa aaagtagtcc tttcacaagg   74820
tctaaggatt tctccactgc tgataatcac aagagaacaa actgagtctc tagatatggga  74880
gaaagtgaga gttgcaacat agttccagac tccagaagaa aagggttcac gtgccacgga   74940
ttgccaagat atcctgtgat aacttagctt ctgcttagag tgcttaggcc tatatctcct   75000
atctactatt ttctctattt cttgggaaag ctgtctgatt ccatctgtgt ttctatctgg   75060
atatttagca cttatcacca ttttattata ttattatata ttattcaact ggattttgtg   75120
gtttaagaga atgttgggct aggaatcaga ccagtggttt aatgcactga aaagacataa   75180
taatgttata ataactaaca cttattgctt atttgctctg tgttgggact atgcttaatg   75240
```

```
ctttacatgg aatgttgaga attactgaag tgttcagtga gcaacaaact atgaaggtag    75300
atctatgtga taaaaattta gtttggtaac agaataaaat atgtaaaaag aagttatctg    75360
tggtgtatgt gggatcattg gtgtgctttg tccttagaca taagtgtagg aggggcatt    75420 tcagatgaat gttgctattt ctacaagtca agccaagtaa ttcaatagaa taaaaatttg    75480
ccattattaa ttattattac tattaatttt gtcaagcctg ggcagctata tgtcatacct    75540
tcagtaaaaa ggaatatcca tagcctagac attgaaacta atatatttat tgttccagat    75600
gctaacacag ctgagtgatg cccttcattc aggagctcct ggggaacaca gtgctatata    75660
atacagtgaa atgggaatca gtgagaagag gaaaaataac ttcatcagga atgtgaatcc    75720
aagattctta aaagggcaga gtacttttct cattcattgt tttttttttt acctccattc    75780
aattaaagag acttggggtc atcgatgttt cttttctctt ccatttcatt tttgacttaa    75840
tacacaaatg gagtatgtta ttgacagagg gtcccccttg tggtccagcg taaactccgt    75900
cattcaatca aaactgcaca ccaaaaacct atatgattca taagcaagtg gcataggtgt    75960
ttgcgctacg tcatatttca acaggtagca tacctccaat ttatttgttt attttgagt    76020 ttcttagttt gtatttgcat tttctgggta ctagattcct gacaagaatc aggtaaggct    76080
gtcatagccc aatatatgga gttctataac tcagcacttt aaagaaaata gtcctcagga    76140
cttaaaaaaa gttttaaaa acttttaaa aagttttta aaaggcaaat taaataatta    76200
tttgtattta aaaaaaatct ttgtgctttt aaaatgctat taatttaaac atgattatgg    76260
acaatagatt gctagtgatg aatgatgggg ttttggacgc gccagacatt gtacagcttc    76320
tcttggggca agcatggtga tcgatgtggg tttcgcaagc tggagtcatt caacttggtg    76380
ttctagtctt gtatatatac ttaatttcat atttaaattg tacaattatg ttatttttgac    76440 tatagtcaac ctgttgtgct attaaatact agatattatt tattctttct aactatttt    76500 tgtacccaat aaccatcccc acctcaccct caaagcctac actaccctt gcagcctatg    76560 gtaactatcc ttctgctctc tacctccatg cgttctattg ttttgatttt tacatcccac    76620
aaataaatga gaacatgaaa tgtttgtctt tctgtgcctg gattatttca cctaaaataa    76680
aatgtttgtc tttcacctaa aataataaaa tgtttgtctt tctgtgcctg gattatttct    76740
cctcaaataa tgatctccag gtccattcat gttgttgcaa atttttttca gtgtctttta    76800
ccacctgttc tggtaccata cccatctgtg ttcaattttt tttgtactga aagtatata    76860 tatatctc caattccctg tgataccgag gaaagacagc atacacacac acacacacac    76920
acacatatgt atatgtatat atatacatat gcatatacag ctactgagtg acaagtggta    76980
tggtataata tcacctgtca ctcagtagct atcatatata tatatataaa acaaggaatt    77040
gtttccagga accccaaaga tactgaaatc tgaggacgct cagctcaagt cccttatgta    77100
aaatggcata gttatattgt ttctctgact tttggctaag atgaagttta gtatctgttc    77160
ttatcagttt aaagtggcat agtatttgca tatagcctat gcatcctcta tacattaagt    77220
aatctctaga ttacttatac tacttaatac aacacacatg ctatgtaaat agttgttata    77280
ctatattttt tatttgtatt atttttatt attgtattgt tatattttaa tgtttgttat    77340
ttccaaacgt ttttaattca tggttggttg aatctgtgaa tgcaaaatcc acggatatgg    77400
agggtcgaat gtacacacac acacacacac acattcataa ttttcaaagt ccacagtaag    77460
tatcaagcag tgtgtgttta cctgcatgtg taggtgaatt aactctgttc ctgaggcggt    77520
tttatttccc tccaatggat tctactttat ttccttaatgt caagaaatgg cttatctcta    77580
tctgagtacc tgtacttcct ttctctgtct ctctctgctg tttctgtctc tgtctctgtc    77640
```

```
tctatcttag tgtttgtgtg ggtgagagat caccattctg cctgcaccac tcaaaatgca   77700
gctctcctaa ctaaaagatt gtattattca cggaggtctc aaacgaaaat gtttctccca   77760
ttggacagaa atgagaatgc cctggcaacc atattaggga aacatgataa tttaccacat   77820
cctctctgta ttcttgttca tttattttc attctgtcgt actctgtacc tttttatagg    77880
ccacttcaat ttgttttta ctagagctgg aaacatgtta cttctcctat gaaccagcca    77940
agttttatg tgcttattat ggattcaaca taccctctt ctcaattcac aacaaatggc     78000
tcctctctat ctgagataga gcaagttgaa gtcctatccc tccagtactg tactttacaa   78060
tgtgaaggct tgggacagat tctcctccac agccccaga gggaacctat cccactgaca    78120
ccttaatttt atacttctag catctataac tgtgagacaa caattttg ttgttttcag     78180
ccactaagtt tgaggtgatt tgttctggca gtcctaggaa actaatacaa tgcctctatt   78240
aaaacaattc atcttgttta ctccagtgtt tttttttt ggcgtatctg tttcagactg     78300
gactatgtac tcatcaagag aaatgacctt atctgtcata tacttcactc tgtggtattt   78360
atgtaaggga tataaaatgt aagacatgat atgctatgta agatatgata cctgccttaa   78420
aatccagtgt ttattcatca aattgttact gagtgcctga tgtaattatg taacagccac   78480
tcctcaggat actggtctta caacggtgag cacagagatg atggtctcct ctctcgtgga   78540
gcaaacagtc tggaaaatgg tggggtgggg ggacattaaa aacacaaaca aaagaaaat    78600
aattgcacaa aaataattgt caagcaggag aaaaacatct gtatgtaaag aagaggaagc   78660
agcgatcatt cttggccatg ggatgatctg gaaaggcttc taaaaggggc agtagatttt   78720
aataaacagc acacacagag agactatttc cttgtgaaga agagaatggg gaaggacccc   78780
tgggtcatta gtagttcatt tgcctggagc atagagaaat agagtaagta gagtaatcat   78840
ggcaatagtt ttttgggtgt ttttaaaatg cttactaagt atcagcctta cattatctca   78900
tttaccttca cattttttg acgtaggctg ttgtcatccc aatttacaga taaggttgtt    78960
gagttttcct taatcgtagc tttatactta ttattatacc ataccacctg tcactcagat   79020
ttattcctag ggataactat aatttgaaat gagatctctg actccacagg ctctgtcttt   79080
ttttcattcc acaacagaga attattccct aaaatgcaga gtcagaaaga taggttgcag   79140
gcagatttta gaatacttct attactaatc aaagactata aaaatatact ttacagtaaa   79200
caaaggagaa aatcaaatgt ctgcaaagta gtaacatgat atacatgcta aaacattgaa   79260
ataggaaaaa atattggggg aagtaggatt ccttagcact tactgaagga aagatccaga   79320
taagaaatgt aaatgtacca ggcttggtgg ctcacacctg taatccctgc actttgggag   79380
gccgcagctg gtagatcact tgaggccagg aatttgacac cagcagggcc aacatggtga   79440
aatcccatct gtattaaaaa tataaaaatt agccaggcct agttacatgc acctgtaatc   79500
ccagctactc aggaggctga ggcaggagaa tcgtttgaac ccgggaggtg gaggttgcag   79560
tgagccgaga ttgtgccact gcacttcagc ctggtcgaca aagtaagact ctgtctcaaa   79620
aacacacaca cacaaaaagc aaaacaagtt atgtaaatcc atcatcagaa tgacttagtg   79680
tgaacaagaa gcatctgagt tgtctgctaa aaattcctgc ttcttcgcaa tgagaatatt   79740
caaaaatctc gcttcaaggt ggtggataaa ttacctcaat ttggtcatta cacaatgcac   79800
ccatttaaac acacatcgaa acatcaggtt gtacctata agtatgcaca attattatgt    79860
gtcaattata tttttgttta aattctactt ccagtcacca ctccagagga ctgctgacgt   79920
gaggaggttt tagacaatat tctgttctgg cctagccaag ggattaggga ggcaatgtaa   79980
```

```
gccaaacttc cttttttcaca gcaagctctt ggactgcagg gatcaaattt cattcaactt   80040
tttattccct tttcccctag gtcccagacc cttgctcata ataagcatgt ggatgactcg   80100
aattgaatta taagagtgaa agactcttgt gaaagaagaa tcattaagac tgtgtgaatt   80160 taaaagaga acgaattcaa gagaacatgc tttgtaagtc tgggaaagag aacgtgcacg   80220
gtacaagggc ggtaacatgt gaccaagaag agaagagtaa aatgaactca ctagccaatt   80280
acattcgagt gatctgctac ttagaatgca tgattgaact cctaggtggt cttatagcca   80340
ctgcgtactt ttcctctgcc agactttgaa agcactttga agacagggtg tcatctaaag   80400
gttggtgatt tgtattgagt tcccccaccc tagaactggc aggcaccatt ctctctgata   80460
aatatcacag gaagaaatca gagaattgta ttttcctttg aaatagttgg aagatatata   80520
gaaaagccta atgtggtttt ctcagttgga aattttccag gacataagga tgtgaatgcc   80580
catcttctca aaagacatgc tgtagatgcc aacagatctg agcagcagga tggaatgtat   80640
cgaaataaat ggcaggatta tccagtgctg gagcccttat ttaagaagcc catattaatt   80700
gagctgaata tagttggcat tccaacaaat atatgctgaa aggaaaatag caaaaacaac   80760
ttaggggata tgttctctca cgtggttgat aatttgtttc ctaacattct gtcactgaac   80820
ctggctggat atggaaaagt ccattctact ttcattctac ttcagctact cagatcttag   80880
ttgtacccta gaactttca tgatggataa ttgtacccttt ctatacttttt catttaaacc    80940 atgtcactca ccaataatta cctatcattt tcagctaatt gcctctagtg ccttggctcc   81000
aaacattctt tgacccaact gtatttacac ttttcctcat tcctttatac ccctaaaatt   81060
tgcagtcccc ttcttactta gctaatattt tacaatctct cccacaaaca ccctcaaatg   81120
gctttgcatc tctcttcttc attgtgttac ttttgtaaaa tccagaccct atttaaatac   81180
aatgttccat gtattctgtg cctgaaccta tgcagctgat gtagctgaag caaagcaggg   81240
gtattggctg gcctcacttt aaattcttca tccttaattg gaaatgtatc ttcatactcc   81300
ctggtaatcc tactttatat attttttacac ctattacttt tcctgaactt ccaatactgc   81360
ctcgctcctc ttcattttgg tttatgaacc tggcttccta tttcactggg gaaatagaag   81420
taatcagtaa taactcgcac gtcttttcac caccacatcg accagcccat cctatctgta   81480
catgtttatt gtctcttcct tccttttctta cttgagctgt acatgctcct atctgatcac   81540
acctatgcac agggtctcat tctctttcac ttcagcaatt agactcttcc ttaaaaaata   81600
attttctgtc tcaacttgat tattcccaca atagtgcaaa catgttgtaa tatctttttt   81660
ctttaaaata acccattttc tttaaaataa tttccaacta tcaactgatt cctctgtttc   81720
tctctctata aaattcctta aaagagattt cttatgttgc ttctctccct ttctctcttt   81780
cccattctca tttgaatcta cttcaaaagg tttactatac taanaaaaca agctcttctc   81840
aagattacct atggtttcca tagtgctaaa ttcagtgata aatttagtct ttgtcttaat   81900
cagcctctcg gtatctttga ttcagagggt aattctctcc ttcttgaaat actttcttca   81960
cttgacttct gggagctact cctcagtttt cctattcact ttagatgttc ccctaagctc   82020
tgtttactca tttatctcat ccctccactg gagttcacta gggttcagtc cttagatcct   82080
ttctctatca gcattcactc acaaggtgat atcacatagc ctttgaatag tatctgaata   82140
ttgatgatgg tcaaatgtta tttcccttga actcgagatt ctattcaact cctactaaac   82200
atccttacct gaacaattaa tagacacatc aaatttaata tatcctaagt tggactcttg   82260
atgtcctgct cttccaaacc tggtcctctt gcacattttc tatctcatta aatgtctatt   82320
tcttcccatt gcctaagcaa ttcagagtca ctctcgaagt gacttttcta atttccccat   82380
```

```
gcatatttga tcgatcagtc gtgttaatta tgccttttaa atgtgtcaag aatctaatta    82440
ctcctcttcc actgctaact tttcttgaaa tgaccatcag ctgtctcttg gataaatacg    82500
atgctttact tttggtattt ctgattcagc atttgcttcc ttattatccg ttctgaacat    82560
agcatctggg ttagaggtct tgtcacctct gtgtcccaaa gtctacagtg attcccacca    82620
ccctccttat caaggctaac aaggccctac atgatctggt ccccacttct tttcagacct    82680
aatttcttct acttttttca ggcttcactc attagccaca ctgtcctcct tggtgtgctt    82740
ccactcttag cacattccca gcaaaggcct tttgttctga ttgtccctct tcttggagct    82800
ctcttcctta aatatctgca aaatatctgc ttatctttt ccatcacatc cttcaggcct    82860
ttcctcaaat gccaatttct cagggaggtt ttccctggca accgtatcta agattacgct    82920
ttcctacccc agcactatca aaccccatcc ctgcacagtt ctcttcctat ttacagccat    82980
ctaacctact acatatgtga catatctatg tattgactgt tttcccctct agaatgtatg    83040
tacaatgagg gcatggatt tgttcactgt ttcatttcca gcaccgtaaa gagaacctga    83100
tatatagaag accctatata agtaacaatt gaatacttaa aggcaggcaa ctctagggtt    83160
tcttccccag acctctgtac cagaaattga aataggaaat agaagatatt gaggatacta    83220
ggtattctct acctgtgtta ttgaccagaa gcagcaacat ataattttc tttgcaagga    83280 ctaagctaat caataacgaa gcaatgtcac tgaaaatcac actcatgaa tgaatttaa    83340 taaaaatata ttttggatg cttttgtta tatttgagag aatgaattga gaatttttgt    83400 tttttttaa gtcaggtgga ctcctaataa cttttaaagg ctaagttaaa aaggtctcat    83460
tttctctaaa gcatttctga cttaccagtc agtcagtcac tctttcctca gcacatttta    83520
tgtgtgtctt aactctagct cttatcacat tatttcatag tttgctgtat tgggttaatt    83580
ccacaactag gctttgtgtc ccgaggagct acaactgctt ctgtcacata gtaggttctc    83640
ataaatcttt gttgaatagc ttatgtagac tcagatgcca caagattggc aataattcac    83700
tgttattaca aaagagaat taatataaaa catcaccttg tttgtagata tattaaagaa    83760
gaagggaacc atgaaacaca atcttaagga attacaatgt gtcctctaag ttttggattt    83820
aattgtccta cctaaatctt aacaaacaaa agcacattga tactttattt ttcttcttct    83880
tatgttttgt attaccctga cttagtcacc agatgtcact atgagactgt tgtccaggtc    83940
actctttctt taaacaagaa ggaaacaaag aactcacatg aggcaaaacc tatggagcaa    84000
aaacacatgg agcaaaacct atgtccttgc ggaaacacct tataaatgtt aaggctagta    84060
gctttagggt tttatttag agtggatttt ggcatggctt agtgtgtaag aaagagcgct    84120
ggactgggaa ttgagactcc tgtattttag ccccaattct gtcattttaa aatatttgac    84180
cacctggtag atttctttac cttttctgggc tgtgaaagat atcctcatct gaaaataagg    84240
gtggccaaag aacctcacaa tcttcaagct ctaacatcca gtgattctat tcccttcttt    84300
tgctaatttc ttggaaagta gccagaagac tttactacca gggatgattt ggaaagtcag    84360
cataagtgag aataatgaat acctattgca tactctattt tattctaaac acagtctctg    84420
ctaggctttg acctaccatg aagtggggaa acctttatgg tcactctcac ttctacacag    84480
tctctgtata ttggtggtac acattgtgtg aaataccttc tccatctaga gattgcttca    84540 ttttttatt ataaaaacat tacacaacat ttgtttaagg tgtcatgtaa atatactttt    84600
agtgactgtc atttttgggg tttcactctc agaggaaaat gaattattta tattaggtat    84660
ttctgaatac ctaatctgaa tatgcttgct tttttaaaaa aaccagttct ctgcaatgtt    84720
```

```
cacccatcca cctacctaaa atatgcacca cttaatctttt tattcatgct gctccacagc   84780
gtgccgtaat cataacccac ttgtggtaga ctcagacact gttgttgtat gaatgcctca   84840
tttatctctt tctgtgcata tttatgtttc agttagctat tttcattgca tgtagttcct   84900
tccatagtgt gggttcttgt attctcagcc attttctttg tcattatttt actcagagtc   84960
gaaccacaga gtaaatattt ttgagaacag tctgaattat atggagcctt taacacttag   85020
aggcactatc ctaatacccca aattattata tagaacaagt tgacacgtgt ttttatagaa   85080
ttatctaatc ctgaaacata tcttgagtat ttactaaatg ctccacactg ttgatgttct   85140
gggattgaaa aacagataa cacagtgtgg cacagagaga gcaggaacaa gcatttacac   85200
agcaaagtgg tgaccgttac agtggagttg tgtgcaacac actgtgggag gctagaggaa   85260
ggcagccagg cttcacagag gatggtatag acttacccctt gagctgacct tcaaaaatag   85320
tcaggaaggt ttgcatggga ggtgggagt ctattccagg cagaggggc agcagaggca   85380
aagaaaaaga ggtttgagac tacatattaa actggagaag tgcatatggt ctatacttac   85440
tgcttagcaa cagagtagaa tgatttgctg ggaggtgaga ctgaattaat attaatctat   85500
tgatttctct ttgaaattta caaaatttttc tcctctcccc ttccttctttt atgtatttttg   85560
gttctactgg agtcagttca ggtgtttctt aggaaattgt tctttatgat ctctgtgagt   85620
tgacattaaa atatacatta tgtatgttct gtgacacatt gttactctta tatgttagtt   85680
gtttaacacc tatatgggct cttgcctcag ctaaacagtg agttctcaaa ggtcacattc   85740
atgattagca gccacactga attattatta catggaagaa tggaaggcag gaatgaagaa   85800
aggaatggtg ggagggagga agaaggtagg aaggaaaaag aaacaagggg cggaataagc   85860
gcttgtagtg gaagatggaa ttaatgtttt tcaagagtat cttagtttct aagatgctca   85920
aatacaatga gaaatatatt tgagcatcct gaattgtgtg aaagttttaa aataatattt   85980
gtcaatgttc aggagaaaaa ttcttctgaa catgtgaaac aagaggaaga ccgaaggtag   86040
atatgcacag aaccctatcc acagttactg agtatgttta gtagggtaga aattgagaaa   86100
aactgcctta tagagagctc agctccaaaa tgactggcat gagatttaaa ctcagcatgt   86160
ataggttaca caaaataata tcacattcca atcatagata tcatagaccc taaaagggca   86220
atagtgcaag atctttcatt gcactgtctt gatatttcta agtcaaactg ctttttgttt   86280
caaggaaaca aaacctcttg aggaagaaac ttctgagatg gcagctgcca gagatataca   86340
agctgcccaa gtgagggggtt aggaaaagct gaagccaggc agacatgact gtgggtccag   86400
gctctacctc ttggtagcta tgtgaccatc agcaaggtgc tgtgtttctt ctacccaagc   86460
ttcagtttcc ttgcttatta aatacaatga gttttttttt tttctttctg acagaggggg   86520
cagcaaagac aaaaaattga ttacaggaca gggagtatct gaaaaactcg gcattgtgcc   86580
tgacacgtaa agtgctcgga aaataacagc cataattatt gttgacaagt ctggagcagg   86640
aaaacaaaca agcatacaaa acacaagatt agactgtagg ttaaaaaata caaggtctag   86700
ttctggctct gtcatttatt ttctatgtaa cctcagtcac atgtgttttt ttccctcatc   86760
tatacaattg gagaattcta cctattgtac ctacttggca gcatcatatg agattatata   86820
gatatagata tatatagcac tatatggtct aagggatcat ttttattaca ggcttgattt   86880
gaaaaacgca gagttccact ccctcaagat gaagcacccg tgccttgttc tgcctgacag   86940
cctaggactg atgctacttg cagaatttta gtgctcagcc ccttcagaga ttgccccagc   87000
tacagagcgg ccataaccaa ccacacaccc tccagagggt tgcctggata aaatgaccac   87060
tccatataga aggcctggcc aaattggccc gagtctggac aacaatgaag ggccctgata   87120
```

```
gcttcagagc tccccatagg gttggtggag gctgctattg agattacttt gcccatcaac    87180
ttctccctgc tgcttcctgc ttccttcccc ttccttcaac agatgtggac tccatggaca    87240
ctccttaata aacatcttgc aagctaaact gcttctcaga atctgcttcc cagagaacta    87300
atcccgtata atcccactga tacatttggt tacatatgta catattgaat aaagtttatt    87360
ttacctagca atttgggtaa aatattagct cgttacaaat ttccaaagtg cacagtgctt    87420
gcaactttta tctcatattg tatgactttg aaagttgttg agagcatatt ttataaataa    87480
tctcgctttg ggtgttttag tagtgtatgt gtagcgcata aattaggcag cattctcata    87540
caacacatat atcaggtact acagggacag aggaagatca gcgtgtatca acaaaaacca    87600
cacattttat gattaacaca gaggatgata tggaaagttg atgtataccc tcccctaatt    87660 ttttcccga ctctacaacc atgctgtgat gttcctggct ttgtgtgagt taacttactt    87720
gggagtacaa gaaaagaaaa gaggcttttc agcgtaggat tatttgttta tttgtttgtt    87780
tgtttgttta agagataaga tctcactctg ttgcccgggc ttaagtgcag tgacgcaatc    87840
atagttcact gcagccttga actcctgggc acaagcaatc caattctccc atcttggcct    87900
cctgagtagc tggaactaaa ggcatgtgcc accatgccca tcatgttgtt tttccttgtt    87960
aaaaccactg aagccatctt cctggtaccc atgatgagat cgcttctcta cttgtcttct    88020
tgttgcttat tctatcatct ctgcacctcc tgctttccaa gaattcactg gctactagat    88080
agccttctgc tattttctag tatccttatg tgctctcaaa atatgtgata cataagcaaa    88140
acactgttaa ccatcacgaa agtttagatt aacagcntnt ttctnttnnt gtagttcaa    88200 tctttcctct ctccttctac cattttttat ttgtttaat gaaaagaggc ttctaagcac    88260
tgattttcac tacctcttca agagccacaa aaatcaaaag tactaagagt aatattttta    88320
actttaggag cccaggcaat ctttcaaata gatgacaagc ttacggtcaa taaagaggaa    88380
ttttaaccac atatctcatg gatacaatga tgaaacttgt ccctttttac agtcaggaag    88440
tagaatcacc agacctcaag tcaaagtcca catttaaatc ccaaacactc agcttcctat    88500
gacgcatgca gacatccttg ccctttgaac atactcatc ccgtaatagc tgttttgcag    88560
tgaatgcaca tttcctggag aatcgaggtt gcctcctggc cttccaatgt cctgtgcttc    88620
acttctataa taggtacata ttcatgggca aagctgttgc ctttgtgttt tcactgttca    88680
agctcaggca ggaacataag ttatcaggat agcatcctaa aagcacttct atttcttcct    88740
gttggcagta catgccagaa aactaaattt tatgttgttt catcttattt ttggcaagtt    88800
cattctgcat aagatatatc ttaacagtag ccaagcacaa gcaatcaaac tcagacttat    88860
tattttctta atcccgtgtc accctcgat atggccattt tggccagatt taccctgtga    88920
ttaaatgtct acttgtgttc tgtttattgg ttattgtctc agtacatctg caattttaag    88980
attcattaca ttatctttg ctcatctctc ctattcacct gtccgcagtc tgtgtttcac    89040
ctttgccctc acctcctgtc atcagcctgt ctcccaaaaa aggccccacc attgttctgt    89100
tgcaaaattc tatttggtca gctgcctcat tacctctatt caggtctttt tcctctcccc    89160
atatgctcca gttctctgtt cctggatatg ctgggtataa ctggcactca ctactgagta    89220
caggtacccc ttatatgtga gagtcctgga ggcacccaac caatctcact atggtcctca    89280
gtcaatgact gaaattgagc tgcatttctt catggagaag tgggaaaaat acctctttcc    89340
caatattagc atggctgtat tccacacaag cataagacat ttatgtttgt gtctccatca    89400
tttacaaagt ttatagtgaa gtagctcttt taggttataa cttacactgc ttactttccc    89460
```

```
caccacctat tagcaaaaga atgagcccat gggacatttg aataggagac caatctgagt    89520
gaagcttatc tacatgcaga taggtaacat ccaaaatgct tcttggtaaa gccaaatgct    89580
gatgaacagt gggccaaact cattagttta gctctattcc ccgctaccca gctttaatga    89640
ggtataactg acaagtaaaa cttacatata tttaagatgt acaacatgat aatttgatat    89700
atatacatgg taaaatggtg accacaatca agttaattaa catatccgtc acctcacata    89760
gttaccattt tttctttgtg gtacaaacac ttaagatcta ctctcttagc aaatataaag    89820
tatacaatac agtattaata actacagtct ctatgttgtc cattacatcc ccagaactta    89880
ttcatctaat aactgaaagt ttatactata tgatcttagc tctttctttt atggtaagtc    89940
tcagactagc cctactcctg ggggagacta gatgaaattc ctgagcagaa agttggagta    90000
gagcaggtag atctgaatag aaatttagca tgaaagaagt cataggggcc taagaagaag    90060
gagcattggg gaaggggaca tggtatgagg acagaagcag aattatcatc aagagactgc    90120
aaagcacata tcaatcataa ctgccaggaa gccatatgga tgccagaata aggctcgtag    90180
tcctattgtg gctatttaca taggcatttc tgcacataac ctctgtcaag ggtacatgtt    90240
ggctgttctc agcaccatcg gacagaacaa accattacca cttgcctctc catgtgtgag    90300
gacctcccag cagaaatact gcttacctgt gccatgagat ttgtttagta cccctgtgct    90360
gtctgggtac cttcctctaa gcttcccagg aaattcctaa ggtctggaaa cacaggatag    90420
tgtttcttga ccagtagtgg ttttcaaaga gaattttcat tccacttcca gcctctgcat    90480
ttgggtagaa caagaccaca ataaaatgaa ttccattaca caatattac ttacaaattc      90540 tgatccttcc tgaagtgact tggaatattg tatttctctt ttgatttgga aagagttgat    90600
atttcttctc accaacctgc actaagttct gtttgaactg agaatctttt acattggctt    90660 tcttttttt ttcccaaaat ctgaagtagt gtttctttg accttaccgt tactgaaagg       90720
agaacaatat ggctataaaa gtaagtgcag cgtctctaag aaatccaagt gtttagcaaa    90780
tcaaatacaa cataaggtac attaaggttt tattaaaatc tcatttattg gcaagagttg    90840
cttctttctg aagagttcta gtctgcctct caagaattaa tctgatgttt tccatttgtt    90900
ttatagtatg tttttaccc ttttcctcac acaggtctca tacctttatg aaacttttcc      90960
cttatgactc tacttcagtg tcgtcttccc agagaaccca accagtgaca tcctgaaagc    91020
atatgctgtg agctttgtga gagctgggac ttaacggcgg ttttgttcag ggctctgttt    91080
ccagtgtcgt gctccgcaga cgacataaag caggcactgg ataggaatgt tgaatgttaa    91140
atgaatgaac agcatccatg cttatggtca acaaacctag tggcctctga gtgtcatgat    91200
gaagagcact tgttctggaa tctgaccata tgagttcagg ttggctcagt gcttcccag     91260 tttgtaacat tggatgagtt cattaacttt tctactcttt tatttttttca tgtgtaaaat   91320 cagaaccata gttgtatcca caagatagtt tttcttaaat ttgtattgtt ttatcttgtt    91380
tttgaagatt aagtgaattg tgaagcactt aggataacac tgagcagata gatgttctca    91440
attaaagtca atgatactac acagtatgaa tgtttatggt ggcaaagtgc tcactatctg    91500
attaggtgat tcttactagt tttagaagtt ttcatctcta gaatgacttt tctgccctct    91560
ccatcaatat actttattat agaagtctgt tcattctctt taaaaaactt agtagtctct    91620
gaaataaact tgctttacaa aatctatacg gagggaaatt ttccatcctg tttagtgtta   91680
tatccccact tcaagaagaa taattaacat gtaatagttg tttaatacat atttatttaa    91740
agaatgcatt gagtaaattg tttaagtttt attttatgt tatggcaaat ttgacctcat      91800
aattgtatct atcagttcta tctcagctcc gtggagcaaa agataatggc tttaatgcct    91860
```

```
tttattttct ttttagctat tcacattttt atttgttatt tttaaaaatt attcttaatt    91920
ttttggtgta catagtagat gtatatatcc ttatggggta catgtgatat tttgatactg    91980
gctttaatgc cttttctata tgacaattta ttggacattt gaagaaacga tctttcctttt   92040
atttctctat tctttacgtt ttccttatga ttgtgtgtgt ggtgggtggg ggtaggtaat    92100
ggaagataat atgaatatag aagaagacat agagaattcc taagatgggg cgggcgtggt    92160
ggcccacgcc tgtaatccca gcaatttggg aggctgaggc aggcagatca catgaggcta    92220
ggaattcaag actagcctgg ccaacatggc ggaaacctgt cttgactaaa aatacaaaaa    92280
ttagctgggc atggtggcac acacctgtaa tcccagttac ctgggaggct gaggcacaag    92340
gatcacctga gctggggaag cagaagttgc agtgagctga gaccacacca ctgcactcca    92400
gcctgggtga cagagtgaga ctctttaaaa gagagagaga gagagagaga gagagagaga    92460
gaattcccaa gagtgaattt ccagctccaa gagctttaaa gtgtcatgtg aagtcactga    92520
aggaagaaga ctttggagag tggtgttcca gtaataatat ccggccgtta gaatagtctc    92580
ctaaaccaca gaaaaatata taccagaaga gtatctaatt caagaaagag gaagatatgt    92640
aacccagaaa atgcaatcag gtctgccata cggaagcaaa tagatggcat ctgtatggca    92700
gacctggaga ggacagaggg gctcagggg gaagatgtac tagtcattta cctatgggtc    92760
cttggctcca gatccatatt cctgtactca actttgtgat gcttaggtta ggactgtaca    92820
aattgtattt cagagaccta tttttcagca ctagagaaat attaggaggt aaaagaagag    92880
gagctgggtc ttcctattta ttgctatttc tgtcaatatc aatctacagt ggtaattcat    92940
ttccacattt ggcagctgaa taaacactat tgggaaaaaa tatacacctg cttttttaaaa   93000
gtcattatta tttaagttct ccctatccac ctgaatagca cactgttcaa agctcatatg    93060
ccattgcaaa ataattcta aaatttgttt ggaaccacaa aagcacctga atagccaaag     93120
caattttgag gaagaagaaa aaacatgaaa tcacacttct tgatttagaa ttatactaca    93180
aagctatagt gatcaaaaca gtatggtatg ggcataaaaa cagacacata gaccaatgaa    93240
acatactaga aagcctgaat ataaacccaa gcacaaacag ttaactaatt tttcccaaag    93300
tcacaagaaa aacaaaatga gacaaggata gtcacttcaa taaatggtgt taggaaaatt    93360
agatatccac tcgtaaaagg ataaaattga atccttatct aacactaaac ataaaagcta    93420
ctcaaagttg attaaaggct taaacataag acctgaaact ataaaattcc tagaagaaaa    93480
tataggaaaa aatactccgt gacattggcc ttgccagtga tttat                   93525
```